US006800469B1

(12) United States Patent
Conrad et al.

(10) Patent No.: US 6,800,469 B1
(45) Date of Patent: Oct. 5, 2004

(54) METHODS FOR DIAGNOSIS AND THERAPY OF AUTOIMMUNE DISEASE, SUCH AS INSULIN DEPENDENT DIABETES MELLITUS, INVOLVING RETROVIRAL SUPERANTIGENS

(75) Inventors: Bernard Conrad, Geneva (CH); Bernard Mach, Chambesy-Geneve (CH)

(73) Assignee: Novimmune S.A., Geneva (CH)

( * ) Notice: Subject to any disclaimer, the term of this patent is extended or adjusted under 35 U.S.C. 154(b) by 0 days.

(21) Appl. No.: 09/490,700

(22) Filed: Jan. 24, 2000

Related U.S. Application Data

(63) Continuation of application No. PCT/EP98/04926, filed on Jul. 22, 1998.

(30) Foreign Application Priority Data

Jul. 22, 1997 (EP) ........................................... 97112482
Jul. 23, 1997 (EP) ........................................... 97401773

(51) Int. Cl.[7] .............................. C12N 9/12; C12Q 1/68
(52) U.S. Cl. .................... 435/194; 435/320.1; 536/23.2
(58) Field of Search .............................. 435/194, 320.1; 536/23.2; 530/350, 845, 868

(56) References Cited

U.S. PATENT DOCUMENTS 5,508,166 A 4/1996 Tanno et al.

FOREIGN PATENT DOCUMENTS

WO 9323560 11/1993
WO 9511975 5/1995
WO 9623076 8/1996
WO 9635793 11/1996
WO 9722694 6/1997

OTHER PUBLICATIONS

Ono et al, J. Virol. Nov. 1986;60(2):589–98.*

Burgess et al., J of Cell Bio. 111:2129–2138, 1990.*

Lazar et al. Molecular and Cellular Biology 8:1247–1252, 1988.*

(List continued on next page.)

*Primary Examiner*—Larry R. Helms
*Assistant Examiner*—Misook Yu
(74) *Attorney, Agent, or Firm*—Mintz,Cohn,Ferris,Glovsky and Popeo, P.C.; Ivor R. Elrifi, Esq.

(57) ABSTRACT

The invention relates to a process for the diagnosis of a human autoimmune disease, including presymptomatic diagnosis, said human autoimmune disease being associated with human retrovirus (HERV) having Superantigen (SAg) activity, comprising specifically detecting in a biological sample of human origin at least one of the following: (I) the mRNA of an expressed human endogenous retrovirus having Superantigen (SAg) activity, or fragments of such expressed retroviral mRNA, said retrovirus being associated with a given autoimmune disease, or (II) protein or peptide expressed by said retrovirus, or (III) antibodies specific to the protein expressed by said endogenous, or (IV) SAg activity specifically associated with said endogenous retrovirus, detection of any of the species (I) to (IV) indicating presence of autoimmune disease or imminent onset of autoimmune disease.

4 Claims, 25 Drawing Sheets

OTHER PUBLICATIONS

Bowie et al. Science, 247:1306–1310, 1990.*

Figure 1A:
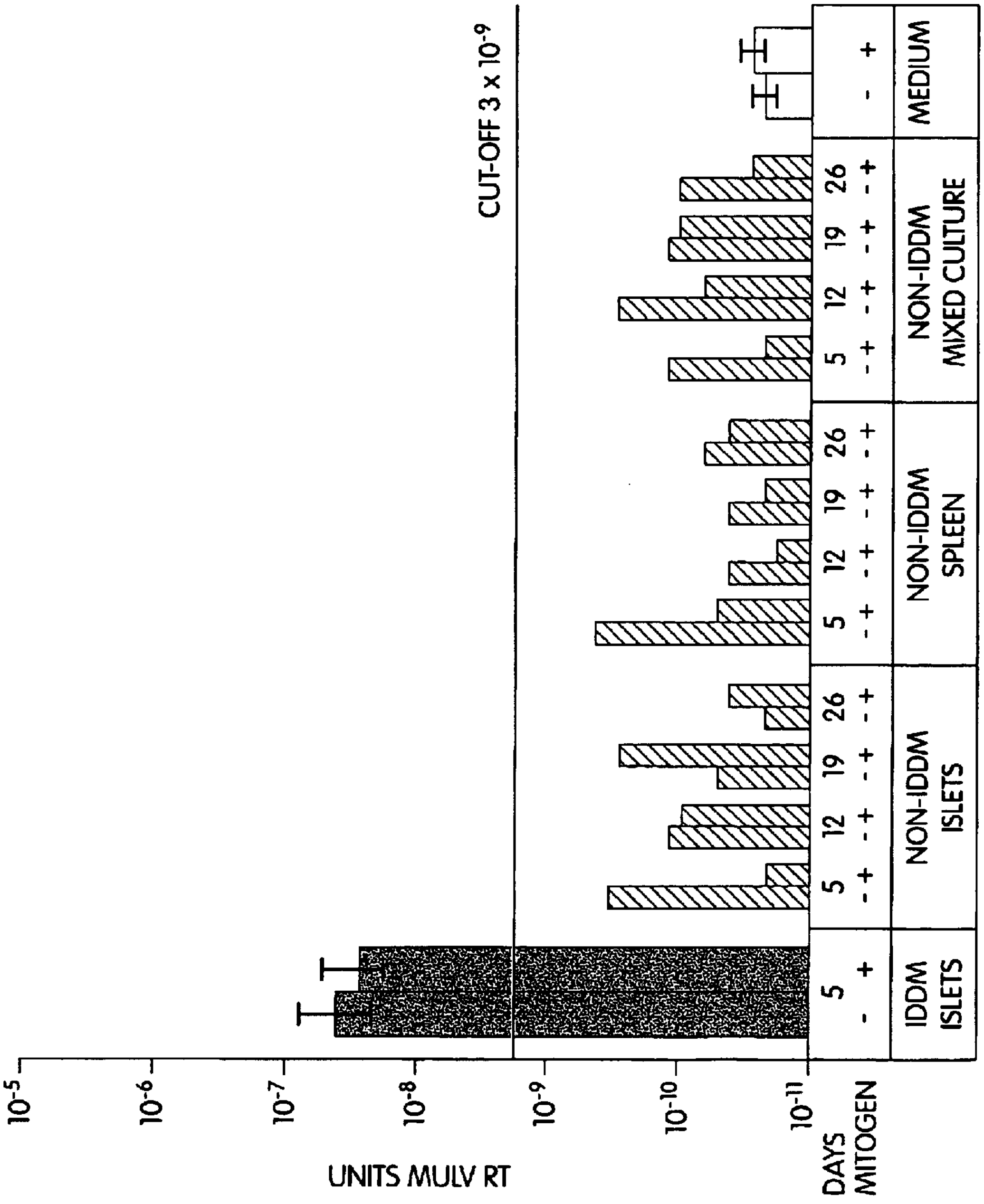

Conrad, et al., Superantigens as Etiopathogenetic Factors in the Development of Insulin–Dependent Diabetes Mellitus, Diabetes/Metabolism Reviews. (1994) 10 (4): 309–338.

Walchner, et al., Endogenous retroviral sequences as a pathogenic factor in systemic lupus erythematosus, Hautarzt (1996) 47: 502–509.

Ono, et al., Nucleotide Sequence of Human Endogenous Retrovirus Genome Related to the Mouse Mamary Tumor Virus Genome, Journal of Virology. (Nov. 1986) 589–598.

Löwer, et al., Identification of a Rev–Related Protein by Analysis of Spliced Transcripts of the Human Endogenous Retroviruses HTDV/HERV–K, Journal of Virology (Jan. 1995) 141–149.

Löwer, et al., A General Method for the Identification of Transcribed Retrovirus Sequences (R–U5 PCR) Reveals the Expression of the Human Endogenous Retrovirus Loci HERV–H and HERV–K in Teratocarcinoma Cells, Virology, (1993) 192: 501–511.

Conrad, et al., A Human Endogenous Retroviral Superantigen as Candidate Autoimmune Gene in Type I Diabetes, Cell, (Jul. 1997) 90: 303–313.

Benoist and Mathis, Retrovirus as trigger, precipitator of marker?, Nature (Aug. 1997) 388 833–834.

* cited by examiner

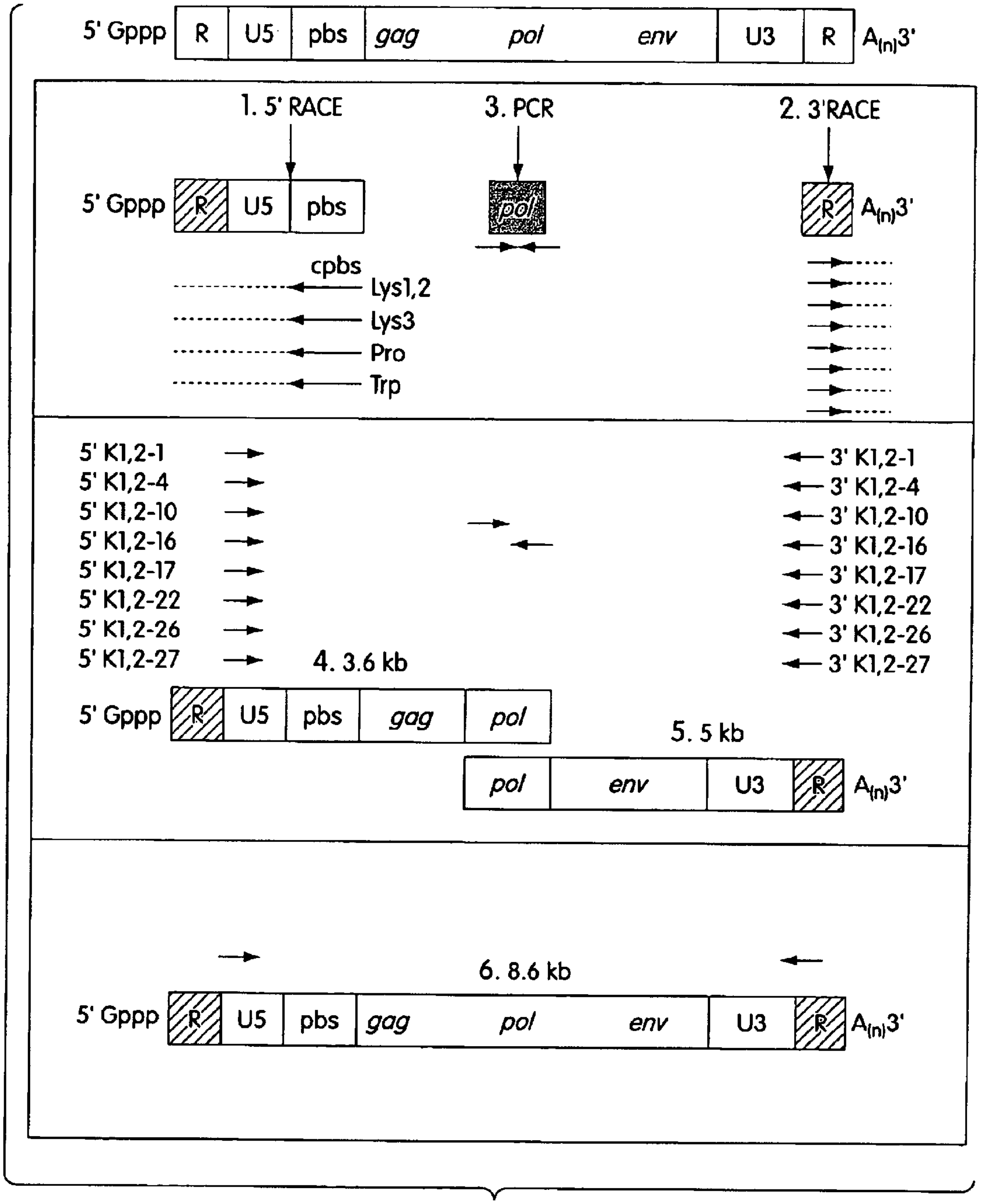
Fig. 2A
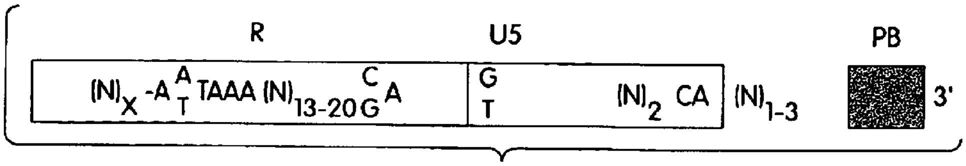
Fig. 2B
Sheet 3 of 25
Inventor: Conrad et al.
U.S.S.N.: 09/490,700
Docket No.: 23135-502
FIGS. 2A & 2B

| TEMPLATE | | SPECIFICITY | IDDM PATIENTS (n=10) | CONTROLS (n=10) |
|---|---|---|---|---|
| RNA | RT+ | U3-R | | |
| | RT+ | U3-R-POLY(A) | | |
| | RT− | U3-R | | |
| | RT− | U3-R-POLY(A) | | |
| DNA | | U3-R | | |

iddmk1,2 22-5'ltr

CATCTCCCTCAGGAGAAACACCCACGAATGATCAATAAATACTAAGGGGACTCAGAGGCTGGT
GGGATCCTCCATATGCTGAACGTTGGTTCCCGGGGCCCCCTTATTTCTTTCTCTATACTTTGT
CTCTGTGTCTTTTTCTTTTCCAAGTCTTCTTCATTTGCACCTTACGAGAAACATCTCCATCAT
GGTTGTTGGATGGGGGCAA

Fig. 7A iddmk1,2 22-3'ltr

CTGCAGGTGTACCCAACAGCTCCGAAGAGACAGTGACATCGAGAACGGGCCATGATGACGATG
GCGGTTTTGTCGAAAAGAAAAGGGGGAAATGTGGGGAAAAGCAAGAGAGATGAGATTGTTACT
GTGTCTGTATAGAAAGAAGTAGACATAGGAGACTCCATTTTGTTCTGTACTAAGAAAAAATTCT
TCTGCCTTGAGATGCTGTTAATCTATGACCTTACCCCCAACCCCGTGCTCTCTGAAACATGTG
CCGTGTCAAAcTCAGGGTTAAATGGATTAAGGGTGGTGCAAGATGTGCTTTGTTAAACAGATG
CTTGAAGGCAGCATGCTCATTAAGAGTCATCACCACTCCCTAATCTCAAGTACCCAGGGACAC
AAACACTGCGAAAGGCCGCAGGGACCTCTGCCTAGGAAAGCCAGGTATTGTCCAAGGTTTCTC
CCCATGTGATAGTCTGAAATATGGCCTCGTGGGAAGGGAAAGACCTGACCATCCCCCAGACCA
ACACCCGTAAAGGGTCTGTGCTGAGGAGGATTAGTATAAGAGGAAAGCATGCCTCTTGCAGTT
GAGAGAAGAGGAAGACATCTGTCTCCTGCCCATCCCcTGGGCAATGGAATGTCTCAGTATAAA
ACCCGATTGAACATTCCATCTACTGAGATAGGGAAAAACTGCCTTAGGGCTGGAGGTGGGACA
TGTGGGCAGCAATACTGCTTTGTAAAGCATTGAGATGTTTATGTGTATGTATATCTAAAAGCA
CAGCACTTGATCCTTTACCTTGTCTATGATGCAAACACCTTTGTTCACGTGTTTGTCTGCTGA
CCCTCTCCCCACTATTGTCTTGTGACCCTGACACATCTCCCTCAGGAGAAACACCCAcgaatg
atcaataaatactaaggggactcagaggctggtgggatcctccatatgctgaacgttggttcc
cggggcccccttatttctttctctatactttgtctctgtgtctttttcttttccaagtcttct
tcatttgcaccttacgagaaacatctccatcatggttgttggatgggggcaa

Fig. 7B iddmk1,2 22-env

```
ATGGTAACACCAGTCACATGGATGGATAATCCTATAGAAGTATATGTTAATGATAGTGTATGG
GTACCTGGCCCCACAGATGATCGCTGCCCTGCCAAACCTGAGGAAGAAGGGATGATGATAAAT
ATTTCCATTGGGTATCATTATCCTCCTATTTGCCTAGGGAGAGCACCAGGATGTTTAATGCCT
GCAGTCCAAAATTGGTTGGTAGAAGTACCTACTGTCAGTCCTAACAGTAGATTCACTTATCAC
ATGGTAAGCGGGATGTCACTCAGGCCACGGGTAAATTATTTACAAGACTTTTCTTATCAAAGA
TCATTAAAATTTAGACCTAAAGGGAAAACTTGCCCCAAGGAAATTCCTAAAGGATCAAAGAAT
ACAGAAGTTTTAGTTTGGGAAGAATGTGTGGCCAATAGTGTGGTGATATTACAAAACAATGAA
TTCGGAACTATTATAGATTAGGCACCTCGAGGTCAATTCTACCACAATTGCTCAGGACAAACT
CAGTCGTGTCCAAGTGCACAAGTGAGTCCAGCTGTCGATAGCGACTTAACAGAAAGTCTAGAC
AAACATAAGCATAAAAAATTACAGTCTTTCTACCTTTGGGAATGGGAAGAAAAAGGAATCTCT
ACCCCAAGACCAAAAATAATAAGTCCTGTTTCTGGTCCTGAACATCCAGAATTGTGGAGGCTT
ACTGTGGCCTCACACCACATTAGAATTTGGTCTGGAAATCAAACTTTAGAAACAAGATATCGT
AAGCCATTTTATACTATCGACCTAAATTCCATTCTAACGGTTCCTTTACAAAGTTGCCTAAAG
CCCCCTTATATGCTAGTTGTAGGAAATATAGTTATTAAACCAGCCTCCCAAACTATAACCTGT
GAAAATTGTAGATTGTTTACTTGCATTGATTCAACTTTTAATTGGCAGCACCGTATTCTGCTG
GTGAGAGCAAGAGAAGGCATGTGGATCCCTGTGTCCACGGACCGACCGTGGGAGGCCTCGCCA
TCCATCCATATTTTGACTGAAATATTAAAAGGCGTTTTAAATAGATCCAAAAGATTCATTTTT
ACTTTAATTGCAGTGATTATGGGATTAATTGCAGTCACAGCTACGGCTGCTGTGGCAGGGGTT
GCATTGCACTCTTCTGTTCAGTCAGTAAACTTTGTTAATTATTGGCAAAAGAATTCTACAAGA
TTGTGGAATTCACAATCTAGTATTGATCAAAAATTGGCAAGTCAAATTAATGATCTTAGACAA
ACTGTCATTTGGATGGGAGACAGGCTTGACTTAGAACATCATTTCCAGTTACAGTGTGACTGG
AATACGTCAGATTTTTGTATTACACCCCAAATTTATAATGAGTCTGAGCATCACTGGGACATG
GTTAGACGCCATCTACAGGGAAGAGAAGATAATCTCACTTTAGACATTTCCAAATTAAAAGAA
CAAATTTTCGAAGCATCAAAAGCCCATTTAAATTTGGTGCCAGGAACTGAGGCAATTGCAGGA
GTTGCTGATGGCCTCGCAAATCTTAACCCTGTCACTTGGATTAAGACCATCAGAAGTACTATG
ATTATAAATCTCATATTAATCGTTGTGTGCCTGTTTTGTCTGTTGTTAGTCTGCAGGTGTACC
CCAACAGCTCCGAAAAAAACAGTGACATCGAGAACGGGCCATGAATGACAAAGGCGGTTTTTG
TTCCAAAAAAAAAGGGGGAAATTTTGGGGAAAACCAAAAAAATGAAAATGTT
```

Fig. 7C

ACA TTT GAA GTT CTA CAA TGA ACC CAT CAG AGA TGC AAA GAA AAG CGC CTC CAC GGA 57

GAT GGT AAC ACC AGT CAC ATG GAT GGA TAA TCC TAT AGA AGT ATA TGT TAA TGA TAG 114
M V T P V T W M D N P I E V Y V N D S 19

TGT ATG GGT ACC TGG CCC CAC AGA TGA TCG CTG CCC TGC CAA ACC TGA GGA AGA AGG 171
V W V P G P T D D R C P A K P E E E G 38

GAT GAT GAT AAA TAT TTC CAT TGG GTA TCA TTA TCC TCC TAT TTG CCT AGG GAG AGC 228
M M I N I S I G Y H Y P P I C L G R A 57

ACC AGG ATG TTT AAT GCC TGC AGT CCA AAA TTG GTT GGT AGA AGT ACC TAC TGT CAG 285
P G C L M P A V Q N W L V E V P T V S 76

TCC TAA CAG TAG ATT CAC TTA TCA CAT GGT AAG CGG GAT GTC ACT CAG GCC ACG GGT 342
P N S R F T Y H M V S G M S L R P R V 95

AAA TTA TTT ACA AGA CTT TTC TTA TCA AAG ATC ATT AAA ATT TAG ACC TAA AGG GAA 399
N Y L Q D F S Y Q R S L K F R P K G K 114

AAC TTG CCC CAA GGA AAT TCC TAA AGG ATC AAA GAA TAC AGA AGT TTT AGT TTG GGA 456
T C P K E I P K G S K N T E V L V W E 133

AGA ATG TGT GGC CAA TAG TGT GGT GAT ATT ACA AAA CAA TGA ATT CGG AAC TAT TAT 513
E C V A N S V V I L Q N N E F G T I I 152

AGA TTA G 520
D * 153

Fig. 7D k1,2-22-env/fs

ACATTTGAAGTTCTACAATGAACCCATCAGAGATGCAAAGAAAAGCGCCTCCACGGAGATGGTA
ACACCAGTCACATGGATGGATAATCCTATAGAAGTATATGTTAATGATAGTGTATGGGTACCTG
GCCCCACAGATGATCGCTGCCCTGCCAAACCTGAGGAAGAAGGGATGATGATAAATATTTCCAT
TGGGTATCATTATCCTCCTATTTGCCTAGGGAGAGCACCAGGATGTTTAATGCCTGCAGTCCAA
AATTGGTTGGTAGAAGTACCTACTGTCAGTCCTAACAGTAGATTCACTTATCACATGGTAAGCG
GGATGTCACTCAGGCCACGGGTAAATTATTTACAAGACTTTTCTTATCAAAGATCATTAAAATT
TAGACCTAAAGGGAAAACTTGCCCCAAGGAAATTCCTAAAGGATCAAAGAATACAGAAGTTTTA
GTTTGGGAAGAATGTGTGGCCAATAGTGTGGTGATATTACAAAACAATGAATTCGGAACTATTA
TAGATTAGGCACCTCGAGGTCAATTCTACCACAATTGCTCAGGACAAACTCAGTCGTGTCCAAG
TGCACAAGTGAGTCCAGCTGTCGATAG

Fig. 7E iddmk1,2 22-ENV

MVTPVTWMDNPIEVYVNDSVWVPGPTDDRCPAKPEEEGMMINISIGYHYPPICLGRA
PGCLMPAVQNWLVEVPTVSPNSRFTYHMVSGMSLRPRVNYLQDFSYQRSLKFRPKG
KTCPKEIPKGSKNTEVLVWEECVANSVVILQNNEFGTIIDZAPRGQFYHNCSGQTQSC
PSAQVSPAVDSDLTESLDKHKHKKLQSFYLWEWEEKGISTPRPKIISPVSGPEHPEL
WRLTVASHHIRIWSGNQTLETRYRKPFYTIDLNSILTVPLQSCLKPPYMLVVGNIVIKP
ASQTITCENCRLFTCIDSTFNWQHRILLVRAREGMWIPVSTDRPWEASPSIHILTEILK
GVLNRSKRFIFTLIAVIMGLIAVTATAAVAGVALHSSVQSVNFVNYWQKNSTRLWNS
QSSIDQKLASQINDLRQTVIWMGDRLDLEHHFQLQCDWNTSDFCITPQIYNESEHH
WDMVRRHLQGREDNLTLDISKLKEQIFEASKAHLNLVPGTEAIAGVADGLANLNPVT
WIKTIRSTMIINLILIVVCLFCLLLVCRCTPTAPKKTVTSRTGHE

Fig. 7F

63
ACATTTGAAGTTCTACAATGAACCCATCAGAGATGCAAAGAAAAGCGCCTCCACGGAGATGGT
2
M V
126
AACACCAGTCACATGGATGGATAATCCTATAGAAGTATATGTTAATGATAGTGTATGGGTACC
23
T P V T W M D N P I E V Y V N D S V W V P
189
TGGCCCCACAGATGATCGCTGCCCTGCCAAACCTGAGGAAGAAGGGATGATGATAAATATTTC
44
G P T D D R C P A K P E E E G M M I N I S
252
CATTGGGTATCATTATCCTCCTATTTGCCTAGGGAGAGCACCAGGATGTTTAATGCCTGCAGT
65
I G Y H Y P P I C L G R A P G C L M P A V
315
CCAAAATTGGTTGGTAGAAGTACCTACTGTCAGTCCTAACAGTAGATTCACTTATCACATGGT
86
Q N W L V E V P T V S P N S R F T Y H M V
378
AAGCGGGATGTCACTCAGGCCACGGGTAAATTATTTACAAGACTTTTCTTATCAAAGATCATT
107
S G M S L R P R V N Y L Q D F S Y Q R S L
431
AAAATTTAGACCTAAAGGGAAAACTTGCCCCAAGGAAATTCCTAAAGGATCAAAGAATACAGA
128
K F R P K G K T C P K E I P K G S K N T E
504
AGTTTTAGTTTGGGAAGAATGTGTGGCCAATAGTGTGGTGATATTACAAAACAATGAATTCGG
149
V L V W E E C V A N S V V I L Q N N E F G
567
AACTATTATAGATTTAGGCACCTCGAGGTCAATTCTACCACAATTGCTCAGGACAAACTCAGT
170
T I I D L G T S R S I L P Q L L R T N S V
601
CGTGTCCAAGTGCACAAGTGAGTCCAGCTGTCGATAG
181
V S K C T S E S S C R *

Fig. 7G iddmk1,2 22-POL

FTIPLAEQDCEKFAFTIPAINNKEPATRFQWKVLPQGMLNSPTICQTFVGRALQPVRDKFSDC
YIIHYFDDILCAAETKDKLIDCYTFLPAEVANAGLAIASDKIQTSTPFHYLGMQIENRKIKPQ
KIEIRKDTLKTLNDFQKLLGDINWIRPTLGIPTYAMSNLFSILRGDSDLNSKRMLT

Fig. 7H k1,2-1 gtaaatgacacctatgatgcactgccaccctttcactgtttcaccctgaacatctgctttttac
atctaagtgattgtacccaataaatagtgtggagaccagagctctgagccttttgcagcctcca
ttttgcaactggtcccctggctcccacctttatgaactcttaacctgtcttttctcattccttt
gtcaccattggactttgggtaccctacgggtggtgttgaggctgtcaccgcacattaa

Fig. 8A k1,2-10 gtttagttaatctataatctatagagacaatgcttatcactggcttgctgtcaataaatatgtg
ggtaaatctctgttcaagactctcagctttgaagctgtgagacccctgatttcccactccacac
ctctatatttctgtgtgtgtgtctttaattcctccagtgttgctgggttagggtctcctcgacg
agctgtcgtgc

Fig. 8B k1,2-16 aactcagctgctgcacagtggtcgagcctccagagctcatgccattgcagtggtcagagcctg
gccctcctcttcctgcatagaacctggattcaatctgtaaggtgggaagtgcagcagcagaga
actctggccttgcagagagtccctgttcccacttcactttccttttcaccaaataaaaccctg
ctttcactcatgcatcaaattgtctgtgagcctacattttgtggccatgggacaagaacacc
atctttagctgagctagggaaaagtcctgca

Fig. 8C k1,2-17 gatgtgaccactgtgacctacctacactggagatggctcacacttccttacccttcccctgct
gtaccaataaataacagcacagcctgacattcggagccattaccggtctttgtgacttggtgg
tagtggtatcccctagggcccagctgtcttttcttttatctctttgtcttgtgtctttatttc
tatgagtctctcgtctccgcacatggggagaaaaacccatagaccctgtagggctg

Fig. 8D k1,2-26 ctcacaaaaataataaaagcttctgttggccattcttcagatcttcatctcttgtgaggatcc
ccctgtacatgtaaaaatgtaataaaacttgtatcctttctcctcttaatctgtcttgcatca
atatcattcctagacccagtcagagatgggtggaggtgagccgtacatttcccta

Fig. 8E k1,2-27 cagagaactccagccagctgtgatggagcctcaggaagttcacagttgcagcaggaaggagcctggc
tgctcctcttcctgtgtggaacctgggattagaacaggctggcaggaagtgctttagcagggactct
ggcctactcacactccttgtttccccccttttcttccttttcactcaataaagccctgtcttactcac
cattcaaattgtctgtgagcctgaattttcatggctgtgggacaaagaaccctatttttagctgaac
taaggaaaattcctgcaaa

Fig. 8F k1,2-4 gtgattgtctgctgaccctctccccacaattgtcttgtgaccctgacacatccccctcttcga
gaaacacccgcggatgatcaataaatattaagggaactcagaggctggcaggatcctccatat
gctgaacgctggttgccccgggtccccttctttctttctctatactttgtctctgtgtctttt
tcttttccaaatctctcgtcccaccttacgagaaacacccacaggtgtgtccgggcaacccaa
cgccacataaca

Fig. 8G

SEQUENCE LISTING

```
<160> NUMBER OF SEQ ID NOS: 49

<210> SEQ ID NO 1
<211> LENGTH: 25
```

-continued

```
<212> TYPE: DNA
<213> ORGANISM: Artificial Sequence
<220> FEATURE:
<223> OTHER INFORMATION: Description of Artificial Sequence: probe

<400> SEQUENCE: 1

tttttgagtc cccttagtat ttatt                                             25


<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 2

atccaacaac catgatggag                                                   20


<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 3

tctcgtaagg tgcaaatgaa g                                                 21


<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 4

gtaaaggatc aagtgctgtg c                                                 21


<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 5

ctttacaaag cagtattgct gc                                                22


<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 6

aacactgcga aaggccgcag g                                                 21


<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 7
```

-continued aggtattgtc caaggtttct cc 22

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 8
yaaatggmgw aygytaacag act 23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 9
yaaatggmgw aygytaactg act 23

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 10
cgtctagagc cytctccggc yatgatcccg 30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 11
cgtctagagc cytctccggc yatgatccca 30

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 12
tgcgccagca atgtatccat g 21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 13
gggtggcagt gcatcatagg t 21

<210> SEQ ID NO 14
<211> LENGTH: 22
<212> TYPE: DNA
<213> ORGANISM: Artificial Sequence -continued
<220> FEATURE:
<223> OTHER INFORMATION: Description of Artificial Sequence: primer

<400> SEQUENCE: 14
gggagagggt cagcagcaga ca 22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 15
gacagcaagc cagtgataag ca 22

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 16
ggaacaggga ctctctgca 19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 17
gggaagggta aggaagtgtg 20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 18
ggtgtttctc ctgagggag 19

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 19
gaagaatggc caacagaagc t 21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 20
gggaaacaag gagtgtgagt 20

-continued

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: primer'

<400> SEQUENCE: 21
catgtatatg cggccgctgc gccagcaatg tatccatgg 39

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: primer'

<400> SEQUENCE: 22
tatctttcgt ttctgcagca c 21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: primer'

<400> SEQUENCE: 23
taactggttg aagagctcga cc 22

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: primer'

<400> SEQUENCE: 24
atactaaggg gactcagagg c 21

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: primer'

<400> SEQUENCE: 25
cagaggctgg tgggatcctc catatgc 27

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 26
tttttgagtc cccttagtat ttatt 25

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: primer -continued

<400> SEQUENCE: 27
aggtattgtc caaggtttct cc 22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 28
ctttacaaag cagtattgct gc 22

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 29
gtaaaggatc aagtgctgtg c 21

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 30
gactaagctt aagaacccat cagagatgc 29

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 31
agactggatc cgttaagtcg ctatcgacag c 31

<210> SEQ ID NO 32
<211> LENGTH: 208
<212> TYPE: DNA
<213> ORGANISM: retroviral provirus

<400> SEQUENCE: 32
catctccctc aggagaaaca cccacgaatg atcaataaat actaagggga ctcagaggct 60
ggtgggatcc tccatatgct gaacgttggt tcccggggcc cccttatttc tttctctata 120
ctttgtctct gtgtcttttt cttttccaag tcttcttcat ttgcacctta cgagaaacat 180
ctccatcatg gttgttggat gggggcaa 208

<210> SEQ ID NO 33
<211> LENGTH: 1060
<212> TYPE: DNA
<213> ORGANISM: retroviral provirus

<400> SEQUENCE: 33
ctgcaggtgt acccaacagc tccgaagaga cagtgacatc gagaacgggc catgatgacg 60

-continued

```
atggcggttt tgtcgaaaag aaaaggggga aatgtgggga aaagcaagag agatgagatt    120

gttactgtgt ctgtatagaa agaagtagac ataggagact ccattttgtt ctgtactaag    180

aaaaattctt ctgccttgag atgctgttaa tctatgacct tacccccaac cccgtgctct    240

ctgaaacatg tgccgtgtca aactcagggt taaatggatt aagggtggtg caagatgtgc    300

tttgttaaac agatgcttga aggcagcatg ctcattaaga gtcatcacca ctccctaatc    360

tcaagtaccc agggacacaa acactgcgaa aggccgcagg gacctctgcc taggaaagcc    420

aggtattgtc caaggtttct ccccatgtga tagtctgaaa tatggcctcg tgggaaggga    480

aagacctgac catcccccag accaacaccc gtaaagggtc tgtgctgagg aggattagta    540

taagaggaaa gcatgcctct tgcagttgag agaagaggaa gacatctgtc tcctgcccat    600

cccctgggca atggaatgtc tcagtataaa acccgattga acattccatc tactgagata    660

gggaaaaact gccttagggc tggaggtggg acatgtgggc agcaatactg ctttgtaaag    720

cattgagatg tttatgtgta tgtatatcta aaagcacagc acttgatcct ttaccttgtc    780

tatgatgcaa acacctttgt tcacgtgttt gtctgctgac cctctcccca ctattgtctt    840

gtgaccctga cacatctccc tcaggagaaa cacccacgaa tgatcaataa atactaaggg    900

gactcagagg ctggtgggat cctccatatg ctgaacgttg gttcccgggg ccccccttatt    960

tctttctcta tactttgtct ctgtgtcttt ttcttttcca agtcttcttc atttgcacct   1020

tacgagaaac atctccatca tggttgttgg atgggggcaa                         1060
```

<210> SEQ ID NO 34
<211> LENGTH: 1754
<212> TYPE: DNA
<213> ORGANISM: Human endogenous retrovirus

<400> SEQUENCE: 34

```
atggtaacac cagtcacatg gatggataat cctatagaag tatatgttaa tgatagtgta     60

tgggtacctg gccccacaga tgatcgctgc cctgccaaac ctgaggaaga agggatgatg    120

ataaatattt ccattgggta tcattatcct cctatttgcc tagggagagc accaggatgt    180

ttaatgcctg cagtccaaaa ttggttggta gaagtaccta ctgtcagtcc taacagtaga    240

ttcacttatc acatggtaag cgggatgtca ctcaggccac gggtaaatta tttacaagac    300

ttttcttatc aaagatcatt aaaatttaga cctaaaggga aaacttgccc caaggaaatt    360

cctaaaggat caaagaatac agaagtttta gtttgggaag aatgtgtggc caatagtgtg    420

gtgatattac aaaacaatga attcggaact attatagatt aggcacctcg aggtcaattc    480

taccacaatt gctcaggaca aactcagtcg tgtccaagtg cacaagtgag tccagctgtc    540

gatagcgact taacagaaag tctagacaaa cataagcata aaaaattaca gtctttctac    600

ctttgggaat gggaagaaaa aggaatctct accccaagac caaaaaataat aagtcctgtt    660

tctggtcctg aacatccaga attgtggagg cttactgtgg cctcacacca cattagaatt    720

tggtctggaa atcaaacttt agaaacaaga tatcgtaagc cattttatac tatcgaccta    780

aattccattc taacggttcc tttacaaagt tgcctaaagc cccccttatat gctagttgta    840

ggaaatatag ttattaaacc agcctcccaa actataacct gtgaaaattg tagattgttt    900

acttgcattg attcaacttt taattggcag caccgtattc tgctggtgag agcaagagaa    960

ggcatgtgga tccctgtgtc cacggaccga ccgtgggagg cctcgccatc catccatatt   1020

ttgactgaaa tattaaaagg cgttttaaat agatccaaaa gattcatttt tactttaatt   1080

gcagtgatta tgggattaat tgcagtcaca gctacggctg ctgtggcagg ggttgcattg   1140
```

-continued cactcttctg ttcagtcagt aaactttgtt aattattggc aaaagaattc tacaagattg 1200
tggaattcac aatctagtat tgatcaaaaa ttggcaagtc aaattaatga tcttagacaa 1260
actgtcattt ggatgggaga caggcttgac ttagaacatc atttccagtt acagtgtgac 1320
tggaatacgt cagatttttg tattacaccc caaatttata atgagtctga gcatcactgg 1380
gacatggtta gacgccatct acagggaaga gaagataatc tcactttaga catttccaaa 1440
ttaaaagaac aaattttcga agcatcaaaa gcccatttaa atttggtgcc aggaactgag 1500
gcaattgcag gagttgctga tggcctcgca aatcttaacc ctgtcacttg gattaagacc 1560
atcagaagta ctatgattat aaatctcata ttaatcgttg tgtgcctgtt ttgtctgttg 1620
ttagtctgca ggtgtacccc aacagctccg aaaaaaacag tgacatcgag aacgggccat 1680
gaatgacaaa ggcggttttt gttccaaaaa aaaaaggggg aaattttggg gaaaaccaaa 1740
aaaatgaaaa tgtt 1754

<210> SEQ ID NO 35
<211> LENGTH: 520
<212> TYPE: DNA
<213> ORGANISM: Human endogenous retrovirus

<400> SEQUENCE: 35
acatttgaag ttctacaatg aacccatcag agatgcaaag aaaagcgcct ccacggagat 60
ggtaacacca gtcacatgga tggataatcc tatagaagta tatgttaatg atagtgtatg 120
ggtacctggc cccacagatg atcgctgccc tgccaaacct gaggaagaag ggatgatgat 180
aaatatttcc attgggtatc attatcctcc tatttgccta gggagagcac caggatgttt 240
aatgcctgca gtccaaaatt ggttggtaga agtacctact gtcagtccta acagtagatt 300
cacttatcac atggtaagcg ggatgtcact caggccacgg gtaaattatt tacaagactt 360
ttcttatcaa agatcattaa aatttagacc taaagggaaa acttgcccca aggaaattcc 420
taaaggatca aagaatacag aagttttagt ttgggaagaa tgtgtggcca atagtgtggt 480
gatattacaa aacaatgaat tcggaactat tatagattag 520

<210> SEQ ID NO 36
<211> LENGTH: 153
<212> TYPE: PRT
<213> ORGANISM: Human endogenous retrovirus

<400> SEQUENCE: 36

Met Val Thr Pro Val Thr Trp Met Asp Asn Pro Ile Glu Val Tyr Val
1 5 10 15

Asn Asp Ser Val Trp Val Pro Gly Pro Thr Asp Asp Arg Cys Pro Ala
20 25 30

Lys Pro Glu Glu Glu Gly Met Met Ile Asn Ile Ser Ile Gly Tyr His
35 40 45

Tyr Pro Pro Ile Cys Leu Gly Arg Ala Pro Gly Cys Leu Met Pro Ala
50 55 60

Val Gln Asn Trp Leu Val Glu Val Pro Thr Val Ser Pro Asn Ser Arg
65 70 75 80

Phe Thr Tyr His Met Val Ser Gly Met Ser Leu Arg Pro Arg Val Asn
85 90 95

Tyr Leu Gln Asp Phe Ser Tyr Gln Arg Ser Leu Lys Phe Arg Pro Lys
100 105 110

Gly Lys Thr Cys Pro Lys Glu Ile Pro Lys Gly Ser Lys Asn Thr Glu

-continued

```
        115                 120                 125

Val Leu Val Trp Glu Glu Cys Val Ala Asn Ser Val Val Ile Leu Gln
    130                 135                 140

Asn Asn Glu Phe Gly Thr Ile Ile Asp
145                 150


<210> SEQ ID NO 37
<211> LENGTH: 603
<212> TYPE: DNA
<213> ORGANISM: Human endogenous retrovirus

<400> SEQUENCE: 37

acatttgaag ttctacaatg aacccatcag agatgcaaag aaaagcgcct ccacggagat      60

ggtaacacca gtcacatgga tggataatcc tatagaagta tatgttaatg atagtgtatg     120

ggtacctggc cccacagatg atcgctgccc tgccaaacct gaggaagaag ggatgatgat     180

aaatatttcc attgggtatc attatcctcc tatttgccta gggagagcac caggatgttt     240

aatgcctgca gtccaaaatt ggttggtaga agtacctact gtcagtccta acagtagatt     300

cacttatcac atggtaagcg ggatgtcact caggccacgg gtaaattatt tacaagactt     360

ttcttatcaa agatcattaa aatttagacc taaagggaaa acttgcccca aggaaattcc     420

taaaggatca aagaatacag aagttttagt ttgggaagaa tgtgtggcca atagtgtggt     480

gatattacaa aacaatgaat tcggaactat tatagattag gcacctcgag gtcaattcta     540

ccacaattgc tcaggacaaa ctcagtcgtg tccaagtgca caagtgagtc cagctgtcga     600

tag                                                                   603


<210> SEQ ID NO 38
<211> LENGTH: 561
<212> TYPE: PRT
<213> ORGANISM: Human endogenous retrovirus
<220> FEATURE:
<221> NAME/KEY: VARIANT
<222> LOCATION: (154)
<223> OTHER INFORMATION: Wherein Xaa at position 154 is "Z" as
      described in the figure legend for FIG. 7F.

<400> SEQUENCE: 38

Met Val Thr Pro Val Thr Trp Met Asp Asn Pro Ile Glu Val Tyr Val
  1               5                  10                  15

Asn Asp Ser Val Trp Val Pro Gly Pro Thr Asp Asp Arg Cys Pro Ala
             20                  25                  30

Lys Pro Glu Glu Glu Gly Met Met Ile Asn Ile Ser Ile Gly Tyr His
         35                  40                  45

Tyr Pro Pro Ile Cys Leu Gly Arg Ala Pro Gly Cys Leu Met Pro Ala
     50                  55                  60

Val Gln Asn Trp Leu Val Glu Val Pro Thr Val Ser Pro Asn Ser Arg
 65                  70                  75                  80

Phe Thr Tyr His Met Val Ser Gly Met Ser Leu Arg Pro Arg Val Asn
                 85                  90                  95

Tyr Leu Gln Asp Phe Ser Tyr Gln Arg Ser Leu Lys Phe Arg Pro Lys
            100                 105                 110

Gly Lys Thr Cys Pro Lys Glu Ile Pro Lys Gly Ser Lys Asn Thr Glu
        115                 120                 125

Val Leu Val Trp Glu Glu Cys Val Ala Asn Ser Val Val Ile Leu Gln
    130                 135                 140

Asn Asn Glu Phe Gly Thr Ile Ile Asp Xaa Ala Pro Arg Gly Gln Phe
```

-continued

```
145                 150                 155                 160

Tyr His Asn Cys Ser Gly Gln Thr Gln Ser Cys Pro Ser Ala Gln Val
                165                 170                 175

Ser Pro Ala Val Asp Ser Asp Leu Thr Glu Ser Leu Asp Lys His Lys
            180                 185                 190

His Lys Lys Leu Gln Ser Phe Tyr Leu Trp Glu Trp Glu Glu Lys Gly
        195                 200                 205

Ile Ser Thr Pro Arg Pro Lys Ile Ile Ser Pro Val Ser Gly Pro Glu
    210                 215                 220

His Pro Glu Leu Trp Arg Leu Thr Val Ala Ser His His Ile Arg Ile
225                 230                 235                 240

Trp Ser Gly Asn Gln Thr Leu Glu Thr Arg Tyr Arg Lys Pro Phe Tyr
                245                 250                 255

Thr Ile Asp Leu Asn Ser Ile Leu Thr Val Pro Leu Gln Ser Cys Leu
            260                 265                 270

Lys Pro Pro Tyr Met Leu Val Val Gly Asn Ile Val Ile Lys Pro Ala
        275                 280                 285

Ser Gln Thr Ile Thr Cys Glu Asn Cys Arg Leu Phe Thr Cys Ile Asp
    290                 295                 300

Ser Thr Phe Asn Trp Gln His Arg Ile Leu Leu Val Arg Ala Arg Glu
305                 310                 315                 320

Gly Met Trp Ile Pro Val Ser Thr Asp Arg Pro Trp Glu Ala Ser Pro
                325                 330                 335

Ser Ile His Ile Leu Thr Glu Ile Leu Lys Gly Val Leu Asn Arg Ser
            340                 345                 350

Lys Arg Phe Ile Phe Thr Leu Ile Ala Val Ile Met Gly Leu Ile Ala
        355                 360                 365

Val Thr Ala Thr Ala Ala Val Ala Gly Val Ala Leu His Ser Ser Val
    370                 375                 380

Gln Ser Val Asn Phe Val Asn Tyr Trp Gln Lys Asn Ser Thr Arg Leu
385                 390                 395                 400

Trp Asn Ser Gln Ser Ser Ile Asp Gln Lys Leu Ala Ser Gln Ile Asn
                405                 410                 415

Asp Leu Arg Gln Thr Val Ile Trp Met Gly Asp Arg Leu Asp Leu Glu
            420                 425                 430

His His Phe Gln Leu Gln Cys Asp Trp Asn Thr Ser Asp Phe Cys Ile
        435                 440                 445

Thr Pro Gln Ile Tyr Asn Glu Ser Glu His His Trp Asp Met Val Arg
    450                 455                 460

Arg His Leu Gln Gly Arg Glu Asp Asn Leu Thr Leu Asp Ile Ser Lys
465                 470                 475                 480

Leu Lys Glu Gln Ile Phe Glu Ala Ser Lys Ala His Leu Asn Leu Val
                485                 490                 495

Pro Gly Thr Glu Ala Ile Ala Gly Val Ala Asp Gly Leu Ala Asn Leu
            500                 505                 510

Asn Pro Val Thr Trp Ile Lys Thr Ile Arg Ser Thr Met Ile Ile Asn
        515                 520                 525

Leu Ile Leu Ile Val Val Cys Leu Phe Cys Leu Leu Leu Val Cys Arg
    530                 535                 540

Cys Thr Pro Thr Ala Pro Lys Lys Thr Val Thr Ser Arg Thr Gly His
545                 550                 555                 560

Glu
```

-continued

<210> SEQ ID NO 39
<211> LENGTH: 604
<212> TYPE: DNA
<213> ORGANISM: Human endogenous retrovirus

<400> SEQUENCE: 39
acatttgaag ttctacaatg aacccatcag agatgcaaag aaaagcgcct ccacggagat 60
ggtaacacca gtcacatgga tggataatcc tatagaagta tatgttaatg atagtgtatg 120
ggtacctggc cccacagatg atcgctgccc tgccaaacct gaggaagaag ggatgatgat 180
aaatatttcc attgggtatc attatcctcc tatttgccta gggagagcac caggatgttt 240
aatgcctgca gtccaaaatt ggttggtaga agtacctact gtcagtccta acagtagatt 300
cacttatcac atggtaagcg ggatgtcact caggccacgg gtaaattatt tacaagactt 360
ttcttatcaa agatcattaa aatttagacc taaagggaaa acttgcccca aggaaattcc 420
taaaggatca aagaatacag aagttttagt ttgggaagaa tgtgtggcca atagtgtggt 480
gatattacaa aacaatgaat tcggaactat tatagattta ggcacctcga ggtcaattct 540
accacaattg ctcaggacaa actcagtcgt gtccaagtgc acaagtgagt ccagctgtcg 600
atag 604

<210> SEQ ID NO 40
<211> LENGTH: 181
<212> TYPE: PRT
<213> ORGANISM: Human endogenous retrovirus

<400> SEQUENCE: 40

Met Val Thr Pro Val Thr Trp Met Asp Asn Pro Ile Glu Val Tyr Val
1 5 10 15

Asn Asp Ser Val Trp Val Pro Gly Pro Thr Asp Asp Arg Cys Pro Ala
20 25 30

Lys Pro Glu Glu Glu Gly Met Met Ile Asn Ile Ser Ile Gly Tyr His
35 40 45

Tyr Pro Pro Ile Cys Leu Gly Arg Ala Pro Gly Cys Leu Met Pro Ala
50 55 60

Val Gln Asn Trp Leu Val Glu Val Pro Thr Val Ser Pro Asn Ser Arg
65 70 75 80

Phe Thr Tyr His Met Val Ser Gly Met Ser Leu Arg Pro Arg Val Asn
85 90 95

Tyr Leu Gln Asp Phe Ser Tyr Gln Arg Ser Leu Lys Phe Arg Pro Lys
100 105 110

Gly Lys Thr Cys Pro Lys Glu Ile Pro Lys Gly Ser Lys Asn Thr Glu
115 120 125

Val Leu Val Trp Glu Glu Cys Val Ala Asn Ser Val Val Ile Leu Gln
130 135 140

Asn Asn Glu Phe Gly Thr Ile Ile Asp Leu Gly Thr Ser Arg Ser Ile
145 150 155 160

Leu Pro Gln Leu Leu Arg Thr Asn Ser Val Val Ser Lys Cys Thr Ser
165 170 175

Glu Ser Ser Cys Arg
180

<210> SEQ ID NO 41
<211> LENGTH: 182
<212> TYPE: PRT
<213> ORGANISM: Human endogenous retrovirus -continued

<400> SEQUENCE: 41

```
Phe Thr Ile Pro Leu Ala Glu Gln Asp Cys Glu Lys Phe Ala Phe Thr
  1               5                  10                  15

Ile Pro Ala Ile Asn Asn Lys Glu Pro Ala Thr Arg Phe Gln Trp Lys
             20                  25                  30

Val Leu Pro Gln Gly Met Leu Asn Ser Pro Thr Ile Cys Gln Thr Phe
         35                  40                  45

Val Gly Arg Ala Leu Gln Pro Val Arg Asp Lys Phe Ser Asp Cys Tyr
     50                  55                  60

Ile Ile His Tyr Phe Asp Asp Ile Leu Cys Ala Ala Glu Thr Lys Asp
 65                  70                  75                  80

Lys Leu Ile Asp Cys Tyr Thr Phe Leu Pro Ala Glu Val Ala Asn Ala
                 85                  90                  95

Gly Leu Ala Ile Ala Ser Asp Lys Ile Gln Thr Ser Thr Pro Phe His
            100                 105                 110

Tyr Leu Gly Met Gln Ile Glu Asn Arg Lys Ile Lys Pro Gln Lys Ile
        115                 120                 125

Glu Ile Arg Lys Asp Thr Leu Lys Thr Leu Asn Asp Phe Gln Lys Leu
    130                 135                 140

Leu Gly Asp Ile Asn Trp Ile Arg Pro Thr Leu Gly Ile Pro Thr Tyr
145                 150                 155                 160

Ala Met Ser Asn Leu Phe Ser Ile Leu Arg Gly Asp Ser Asp Leu Asn
                165                 170                 175

Ser Lys Arg Met Leu Thr
            180
```

<210> SEQ ID NO 42
<211> LENGTH: 250
<212> TYPE: DNA
<213> ORGANISM: Human endogenous retrovirus

<400> SEQUENCE: 42

```
gtaaatgaca cctatgatgc actgccaccc tttcactgtt tcaccctgaa catctgcttt     60

ttacatctaa gtgattgtac ccaataaata gtgtggagac cagagctctg agccttttgc    120

agcctccatt ttgcaactgg tcccctggct cccaccttta tgaactctta acctgtcttt    180

tctcattcct ttgtcaccat tggactttgg gtaccctacg ggtggtgttg aggctgtcac    240

cgcacattaa                                                           250
```

<210> SEQ ID NO 43
<211> LENGTH: 203
<212> TYPE: DNA
<213> ORGANISM: Human endogenous retrovirus

<400> SEQUENCE: 43

```
gtttagttaa tctataatct atagagacaa tgcttatcac tggcttgctg tcaataaata     60

tgtgggtaaa tctctgttca agactctcag ctttgaagct gtgagacccc tgatttccca    120

ctccacacct ctatatttct gtgtgtgtgt ctttaattcc tccagtgttg ctgggttagg    180

gtctcctcga cgagctgtcg tgc                                            203
```

<210> SEQ ID NO 44
<211> LENGTH: 283
<212> TYPE: DNA
<213> ORGANISM: Human endogenous retrovirus -continued

<400> SEQUENCE: 44
aactcagctg ctgcacagtg gtcgagcctc cagagctcat gccattgcag tggtcagagc 60
ctggccctcc tcttcctgca tagaacctgg attcaatctg taaggtggga agtgcagcag 120
cagagaactc tggccttgca gagagtccct gttcccactt cactttcctt ttcaccaaat 180
aaaaccctgc tttcactcat gcatcaaatt gtctgtgagc ctacattttt gtggccatgg 240
gacaagaaca ccatctttag ctgagctagg gaaaagtcct gca 283

<210> SEQ ID NO 45
<211> LENGTH: 245
<212> TYPE: DNA
<213> ORGANISM: Human endogenous retrovirus

<400> SEQUENCE: 45
gatgtgacca ctgtgaccta cctacactgg agatggctca cacttcctta cccttcccct 60
gctgtaccaa taaataacag cacagcctga cattcggagc cattaccggt ctttgtgact 120
tggtggtagt ggtatcccct agggcccagc tgtcttttct tttatctctt tgtcttgtgt 180
ctttatttct atgagtctct cgtctccgca catggggaga aaaacccata gaccctgtag 240
ggctg 245

<210> SEQ ID NO 46
<211> LENGTH: 181
<212> TYPE: DNA
<213> ORGANISM: Human endogenous retrovirus

<400> SEQUENCE: 46
ctcacaaaaa taataaaagc ttctgttggc cattcttcag atcttcatct cttgtgagga 60
tccccctgta catgtaaaaa tgtaataaaa cttgtatcct ttctcctctt aatctgtctt 120
gcatcaatat cattcctaga cccagtcaga gatgggtgga ggtgagccgt acatttccct 180
a 181

<210> SEQ ID NO 47
<211> LENGTH: 287
<212> TYPE: DNA
<213> ORGANISM: Human endogenous retrovirus

<400> SEQUENCE: 47
cagagaactc cagccagctg tgatggagcc tcaggaagtt cacagttgca gcaggaagga 60
gcctggctgc tcctcttcct gtgtggaacc tgggattaga acaggctggc aggaagtgct 120
ttagcaggga ctctggccta ctcacactcc ttgtttcccc cctttcttcc ttttcactca 180
ataaagccct gtcttactca ccattcaaat tgtctgtgag cctgaatttt catggctgtg 240
ggacaaagaa ccctattttt agctgaacta aggaaaattc ctgcaaa 287

<210> SEQ ID NO 48
<211> LENGTH: 264
<212> TYPE: DNA
<213> ORGANISM: Human endogenous retrovirus

<400> SEQUENCE: 48
gtgattgtct gctgaccctc tccccacaat tgtcttgtga ccctgacaca tccccctctt 60
cgagaaacac ccgcggatga tcaataaata ttaagggaac tcagaggctg gcaggatcct 120
ccatatgctg aacgctggtt gccccgggtc cccttctttc tttctctata ctttgtctct 180
gtgtcttttt cttttccaaa tctctcgtcc caccttacga gaaacaccca caggtgtgtc 240

-continued

```
cgggcaaccc aacgccacat aaca                                          264


<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 49

tttttttttt tttttttttt gagtcccctt agtatttatt                          40
```

METHODS FOR DIAGNOSIS AND THERAPY OF AUTOIMMUNE DISEASE, SUCH AS INSULIN DEPENDENT DIABETES MELLITUS, INVOLVING RETROVIRAL SUPERANTIGENS

This application is a continuation of PCT International Application No. PCT/EP98/04926, filed 22 Jul. 1998, designating the United States of America and claiming priority of European Application Nos. 97112482.1, filed Jul. 22, 1997 and 97401773.3, filed Jul. 23, 1997.

The present invention relates to methods for the diagnosis of human autoimmune disease, for example Insulin Dependent Diabetes Mellitus (IDDM), and to methods for identifying substances which can be used in the therapy and prevention of such diseases. The invention further relates to novel human retroviruses involved in autoimmune disease and having superantigen activity, as well as to their expression products.

For some autoimmune diseases such as IDDM, Multiple Sclerosis, arthritis and others, it is known that a combination of genetic, environmental and possibly exogenous infectious factors may be important in precipitating disease. However, the precise roles of each these factors remains incompletely elucidated. For example, for IDDM, the Major Histocompatibility Complex (MHC) Class II genotype is one of the strongest genetic factors determining disease susceptibility (Vyse, T. J. and Todd J. A., 1996) although the respective roles of the different MHC Class $II^+$ cell types in promoting disease has not yet been clarified. Furthermore, IDDM shows temporal, epidemic-like variations and the clinical disease exhibits preferential seasonal onset (Karvonen et al., 1993). Recently, Conrad et al. (1994) provided evidence for superantigen involvement in IDDM aetiology and postulated that viruses may be the modifying agent responsible for the presence of superantigen on diabetic islets.

Genetic background also has an important influence in multiple sclerosis. In addition, Perron et al (Perron et al, 1997) have recently identified a retrovirus which can be isolated from cells of multiple sclerosis patients. Whether the retrovirus contributes as a causative agent of multiple sclerosis or as a link in the pathogenic process, or whether it is merely an epiphenomenon, has not been identified. No superantigen activity of the retrovirus has been identified.

It is an aim of the present invention to identify agents implicated in the pathogenesis of human autoimmune diseases, such as IDDM, and on the basis of these agents to provide reliable diagnostic procedures and therapeutic or prophylactic substances and compositions.

These objectives are met by the provision, according to the invention, of diagnostic procedures involving the detection of expressed retroviruses having superantigen (SAg) function, these retroviruses being directly involved in the pathogenesis of human autoimmune disease by activation of autoreactive T-cells. Compounds and compositions capable of blocking SAg function or production are also provided as therapeutic and prophylactic agents in the treatment of autoimmune disease.

The present invention is based on the discovery, by the present inventors that superantigens (SAgs) encoded by retroviruses, particularly endogenous retroviruses, play a major role in the pathogenesis of autoimmune disease, very likely by activating autoreactive T-cells.

Superantigens (SAgs) (Choi et al, 1989; White et al, 1989) are microbial proteins able to mediate Interactions between MHC Class $II^+$—and polyclonal T-cells resulting in reciprocal activation (Acha-Orbea et al, 1991; Choi et al, 1991; Fleischer and Schrezenmeier, 1988). Their function is restricted by only two absolute requirements: the presence of MHC Class II on the surface of the presenting cells and the expression of one or more defined Variable (V)-β T cell receptor (TCR) chain(s) on T cells.

The potential role of SAgs in human diseases is ill-defined. Bacterial SAgs have been proposed to be associated with the pathogenesis of autoimmune disease (White et al, 1989). However, although pathogen disease associations have been described, none of these have as yet implicated a pathogen-encoded SAg (Howell et al, 1991; Paliard et al, 1991). A SAg-like activity resembling the one encoded by MMTV has been reported to be associated with herpesvirus infections (Dobrescu et al, 1995; Sutkowski et al, 1996). However, in none of these two systems has it been demonstrated that the SAg activity is actually encoded by the infectious agent. SAg activity has been reported in patients having Type I diabetes (Conrad et al 1994). However, the origin of the Sag activity is not identified.

In the framework of the present invention, the inventors have identified the source of SAg activity in IDDM patients as being a novel endogenous retrovirus, (HERV) designated $IDDKK_{1,2}$-22. This retrovirus is related to, but distinct from mouse mammary tumor virus (MMTV). It is ubiquitous in the human genome but is only expressed in diabetic individuals, possibly in response to a particular environmental stimulus. The HERV encodes superantigen (SAg) activity within the env gene. Expression of the SAg gives rise to preferential expansion of Vβ-7 T-cell receptor positive T-cells, some of which are very likely to be autoreactive. Thus the expression of self-SAg leads to systemic activation of a sub-set of T-lymphocytes, among which autoreactive T-cells, will in turn give rise to organ-specific autoimmune disease.

The involvement of retroviral SAg, particularly endogenous retroviral SAg in autoimmune disease is unexpected. Indeed, endogenous retroviruses (HERV) form an integral part of the human genome. If expressed from birth, any autoreactive T-cells activated by expression of a retroviral SAg should be deleted as part of the normal development of the immune system (thymic deletion). However, in the case of autoimmune diseases such as diabetes, the expression of the retrovirus, and hence of the encoded SAg, occurs only later in life, leading to the proliferation of autoreactive T-cells.

To identify the microbial agent responsible for SAg activity in diabetes, the present inventors have developed a novel primer-extension technique. This method can be used to isolate and identify, in a sample polyadenylated RNA, any expressed, previously unidentified retroviral RNA, particularly retroviruses having SAg activity and being involved in human autoimmune disease. This strategy relies on the following three characteristic features of functional retroviruses. First, retroviral genomes contain a primer binding site (PBS) near their 5' end. Cellular tRNAs anneal to the PBS and serve as primers for Reverse Transcriptase (reviewed by Whitcomb and Hughes, 1992). Second, the R (repeat) sequence is repeated at the 5' and 3' ends of the viral RNA (Temin, 19B1). Third, the RT-RNAse H region of the pol gene is the most conserved sequence among different retroelements (McClure et al., 1988; Xiong and Eickbusch, 1990). The method comprises the following steps:

i) isolation of the 5' R-U5 ends of expressed putative retroviral genomes using nucleic acid amplification, the 3' primer being complementary to known <primer binding sites> (pbs).

ii) isolation of the 3' R-poly(A) ends corresponding to the 5' R-U5 ends, by use of primers specific for the R regions isolated in step i).

iii) amplification of the conserved RT-RNase H region within the pol gene by using degenerate primers corresponding to the conserved region.

iv) amplification of the 5' moiety of the putative retroviral genome by using primers specific for the different U5 regions isolated in step i) in conjunction with a primer specific for the 3' end of the central pol region isolated in step iii).

v) amplification of the 3' moiety of the putative retroviral genome using primers specific for the central pol region isolated in step iii) in conjunction with primers specific for the poly(A) signals present in the 3' R-poly(A) sequences isolated in step ii).

vi) confirmation of the presence of an intact retroviral genome by amplification using primers specific for its predicted U5 and U3 regions.

Once an expressed retrovirus has been identified, its SAg activity can be tested by contacting a biological sample containing MHC Class $II^+$ cells expressing the putative Sag activity, with cells bearing one or more variable (V)-β T-cell receptor (TCR) chains and detecting preferential proliferation of a Vβ subset.

The techniques developed by the inventors to elucidate Sag involvement in IDDM, can be used to identify the possible involvement of expressed retrovirus and encoded SAg activity in other autoimmune diseases. The characterisation of the retrovirus and its SAg can then be made, and the particular Vβ-T cell receptor chain activation associated with the SAg can be identified. A given autoimmune disease can thus be defined by reference to a characterised retroviral Sag specifically associated with the disease, and to the Vβ-specificity or specificities. In certain autoimmune diseases, such as multiple sclerosis, it is known that T-cells with different Vβ specificities can be involved in the recognition of the same immunodominant autoantigen, M.B.P. (Wucherpfennig K. W. et al, *Science* 1990, 25, 1016–1019). Once this <profile> has been determined, specific diagnostic, therapeutic and prophylactic tools can be elaborated for each autoimmune disease involving retroviral SAg-stimulation of autoreactive T-cells.

The present invention involves, in a first embodiment, methods of diagnosis of autoimmune disease based on the specific expression, in autoimmune patients, of retroviruses having Sag activity.

The methods of diagnosis of the present invention are advantageous in so far as they are highly specific, distinguishing between expressed and non-expressed viral nucleic acid, and can thus be reliably used even when the pathological agent is a ubiquitous endogenous retrovirus. They can be carried out on easily accessible biological samples, such as blood or plasma, without extensive pre-treatment. The diagnostic methods of the invention detect disease-specific expression of the retrovirus and can thus be applied before appearance of clinical symptoms, for example on genetically predisposed individuals. This allows suitable therapy to be initiated before autoimmune destruction of a particular target tissue occurs.

In the context of the present invention the following terms encompass the following meanings:

- a <human autoimmune disease> is defined as a polygenic disease characterised by the selective destruction of defined tissues mediated by the immune system. Epidemiological and genetic evidence also suggests the involvement of environmental factors.
- a <human endogenous retrovirus> (HERV) is a retrovirus which is present in the form of proviral DNA integrated into the genome of all normal cells and is transmitted by Mendelian inhertance patterns. Such proviruses are products of rare infection and integration events of the retrovirus under consideration into germ cells of the ancestors of the host. Most endogenous retroviruses are transcriptionally silent or defective, but may be activated under certain conditions. Expression of the HERV may range from transcription of selected viral genes to production of complete viral particles, which may be infectious or non-infectious. Indeed, variants of HERV viruses may arise which are capable of an exogenous viral replication cycle, although direct experimental evidence for an exogenous life cycle is still missing. Thus, in some cases, endogenous retroviruses may also be present as exogenous retroviruses. These variants are included in the term <HERV> for the purposes of the invention. In the context of the invention, <human endogenous retrovirus> includes proviral DNA corresponding to a full retrovirus as represented schematically in FIG. 2A, comprising two LTR's, gag, pol and env, and further includes remnants or <scars > of such a full retrovirus which have arisen as a results of deletions in the retroviral DNA. Such remnants include fragments of the structure depicted in FIG. 2A, and have a minimal size of one LTR. Typically, the HERVs have at least one LTR, preferably two, and all or part of gag, pol or env.
- a Superantigen is a substance, normally a protein, of microbial origin that binds to major histocompatibility complex (MHC) Class II molecules and stimulates T-cell, via interaction with the Vβ domain of the T-cell receptor (TCR). SAgs have the particular characteristic of being able to interact with a large proportion of the T-cell repertoire, i.e. all the members of a given Vβ subset or <family>, or even with more than one Vβ subset, rather than with single, molecular clones from distinct Vβ families as is the case with a conventional (MHC-restricted) antigen. The superantigen is said to have a mitogenic effect that is MHC Class II dependent but MHC-unrestricted. SAgs require cells that express MHC Class II for stimulation of T-cells to occur.
- <SAg activity> signifies a capacity to stimulate T-cells in an MHC-dependent but MHC-unrestricted manner. In the context of the invention, SAg activity can be detected in a functional assay by measuring either IL-2 release by activated T-cells, or proliferation of activated T-cells.
- a retrovirus having SAg activity is said to be <associated with> a given autoimmune disease when expressed retroviral RNA can be found specifically in biological samples of autoimmune patients (ie the expressed retroviral RNA is not found in individuals free of autoimmune disease). Preferably <associated with> further signifies in this context that retroviral SAg activation of a Vβ subset gives rise directly or indirectly to proliferation of autoreactive T-cells targeting tissue characteristic of the autoimmune disease. Blockage of SAg activity thus normally prevents generation of autoreactive T-cells. Disease <association> with Sag can also be defined immunologically or genetically: immunological association means that a particular disease-associated HLA haplotype is permissive for Sag, whereas resistant haplotypes are permissive for Sag inhibition. Genetic association implies a polymorphism in either the expression pattern of Sag or in the amino acid sequence of Sag, with Sag alleles exhibiting different degree of susceptibility to the disease.
- cells which <functionally express> Sag are cells which express Sag in a manner suitable for giving rise to MHC-dependent, MHC-unrestricted T-cell stimulation in vitro or in vivo. This requires that the cell be MHC $II^+$ or that it has been made MHC $II^+$ by induction by agents such as IFN-γ.

More particularly, in a first embodiment, the present invention relates to a process for the diagnosis of a human autoimmune disease, including pre-symptomatic diagnosis, said human autoimmune disease being associated with human retrovirus having Superantigen (SAg) activity, comprising specifically detecting in a biological sample of human origin at least one of the following:

I: the mRNA of an expressed human retrovirus known to have Superantigen (SAg) activity, or fragments of such expressed retroviral mRNA, said retrovirus being associated with a given autoimmune disease, or II: protein expressed by said retrovirus, or III: antibodies specific to the proteins expressed by said retrovirus, or IV: SAg activity specifically associated with the autoimmune disease.

Thus, the diagnosis of a given autoimmune disease can be made, according to the invention, by one or more of four methods (I to IV), each involving the detection of a specific aspect of the expression of a SAg-encoding retrovirus known to be associated with the autoimmune disease, particularly an endogenous retrovirus. Detection of any of the species (I) to (IV) as listed above is indicative of the presence of the autoimmune disease specifically associated with the endogenous retrovirus under consideration or of imminent onset of the disease.

Each of the four possible methods I to IV of diagnosis of human autoimmune disease will be described in detail below.

According to method I, the autoimmune disease is diagnosed by specifically detecting in a biological sample the mRNA of an expressed human retrovirus known to have SAg activity.

Specific detection of retroviral expressed mRNA is preferably carried out using nucleic acid amplification with viral specific primers which discriminate between proviral DNA and expressed RNA template. This is of particular importance when the retrovirus associated with the autoimmune disease is an endogenous retrovirus. Indeed in such cases, the proviral DNA is present in all human cells, whether or not the autoimmune disease is present. False positives would be obtained if a detection method were used which does not distinguish between proviral DNA and transcribe mRNA.

The biological sample to be used for specific mRNA detection according to the invention may be any body fluid or tissue but is preferably plasma or blood. Normally, total RNA is extracted from the sample using conventional techniques. DNAse treatment may be carried out to reduce contaminating cellular DNA.

By performing the amplification on total RNA samples, the effects of contaminating DNA are reduced but not eliminated, even after treatment by DNAse. The method of the present invention allows selective amplification of expressed viral RNA transcripts using at least one m-RNA specific primer, for example a poly-A specific primer, even in the presence of contaminating viral DNA in the sample. The poly-A specific primer is specific for the poly-A signaals present in the R-poly(A) sequences and the 3' extremity of the retrovirus (see for example FIG. 2A step 5 and FIG. 2C).

It has surprisingly been found that a poly-A-specific primer having from four to 25 t's for example 5 or 20 T's is optimal for the purposes of the present invention.

The mRNA specific amplification requires a reverse transcriptase (RT) step, for which the poly A-specific primer is also be used.

The second primer in the PCR step is generally complementary to the U3 region. When the amplification product has a size of about 300 to 500 nucleotides, the conditions applied for the amplification (PCR) step are normally the following:

| | | |
|---|---|---|
| i) reverse transcriptase: | 50° C. | 30 minutes |
| ii) amplification (for a total of 10 | 94° C. | 2 minutes |
| cycles): | 94° C. | 30 secondes |
| | 68° C. | 30 secondes |
| | −1.3° C. | each cycle |
| | 68° C. | 45 secondes |
| iii) amplification (for a total 25 cycles): | 94° C. | 30 secondes |
| | 55° C. | 30 secondes |
| | 68° C. | 45 secondes |

The amplified material is subjected to gel electrophoresis and hybridised with suitable probes, for example generated from the U3 region.

By performing the mRNA specific detection of the invention, the presence of a given expressed retrovirus can be reliably determined in a biological sample. For endogenous retroviruses expression generally indicates onset of the disease process. This can be detected well before the apparition of any clinical symptoms. The diagnosis of the invention can thus be used to detect onset of the disease process, enabling treatment to be administered before irreversible autoimmune attack occurs.

The invention also encompasses pro-viral specific detection of retroviral DNA, and simultaneous detection of both expressed retroviral m-RNA and proviral DNA. Details of these methods are given in FIG. 2D and 2E, and associated legends. Specific proviral DNA detection can be used on healthy biological samples to confirm the endogenous nature of the retrovirus, the assay detecting both retroviral mRNA and proviral DNA can be used as an internal standard.

According to a preferred embodiment of the invention, the autoimmune disease detected is IDDM. The present inventors have identified, a human endogenous retrovirus associated with IDDM. This novel retrovirus (called $IDDMK_{1,2}$-22) has SAg activity encoded in the $NH_2$ terminal portion of the env gene, causing preferential proliferation of Vβ7—TCR chain bearing T-cells.

$IDDMK_{1,2}$-22 comprises the 5' LTR, 3' LTR and env-encoding sequences shown in FIGS. 7A, 7B and 7C respectively, and further comprises gag-encoding sequences. The SAg portion of the env protein occurs within the sequences shown in FIG. 7D or 7G, particularly 7G.

Diagnosis of IDDM by specific detection of expressed retroviral RNA is carried out using a polyA specific probe of the type:

5' TTTTTGAGTCCCCTTAGTATTTATT 3' (SEQ ID NO:1)

or similar sequence specifically hybridising to the polyA region of $IDDMK_{1,2}$-22 type retroviruses, having at least 90% sequence identity with the $IDDMK_{1,2}$-22 and having SAg activity.

According to a second embodiment (II) of the invention, the human autoimmune disease associated with a retroviral SAg is diagnosed by specifically detecting protein expressed by the retrovirus, particularly gag, pol or env. In the case of endogenous retroviruses, the expressed proteins may be slightly different from the expected products as a result of read-through phenomena and possibly reading-frame shifts. Preferably, the expressed protein is detected in the biological sample, such as blood or plasma, using antibodies, particularly monoclonal antibodies, specific for the said protein. A Western-like procedure is particularly preferred, but other antibody-based recognition assays may be used.

In the case of IDDM, a preferred diagnostic method comprises the detection of a protein encoded by the env gene, as shown in FIG. 7C, 7D or 7G, or the pol protein shown in FIG. 7H, or the IDDMK$_{1,2}$-22 GAG protein. Alternatively, proteins having at least approximately 90% homology with these proteins, or proteins arising from read-through of internal stop codons, possibly with frameshift, particularly a −1 frame shift, occurring immediately after the internal stop codon. Fragments of any of these proteins having at least 6, and preferably at least 10 amino acids, for example 6–20, or 10–15 amino acids, may also be detected. Preferred proteins for this type of diagnostic assay are those having SAg activity. It is also possible to detect retroviral particles when produced.

According to a third embodiment (III) of the invention, the autoimmune disease is diagnosed by detecting in a biological sample, antibodies specific for the protein expressed by the associated retrovirus.

Detection of antibodies specific for these proteins is normally carried out by use of the corresponding retroviral protein or fragments thereof having at least 6 amino-acids, preferably at least 10, for example 6–25 amino acids. The proteins are typically Gag, Pol or Env or fragments thereof and may or may not have superantigen activity. The retroviral proteins used in the detection of the specific antibodies may be recombinant proteins obtained by introducing viral DNA encoding the appropriate part of the retrovirus into eukaryotic cell and the conditions allowing the DNA to be expressed and recovering the said protein.

In the context of the present invention, the terms "antibodies specific for retroviral proteins" signifies that the antibodies show no significant cross reaction with any other proteins likely to occur in the biological sample. Generally, such antibodies specifically bind to an epitope which occurs exclusively on the retroviral protein in question. The antibodies may recognize the retroviral protein having SAg activity as presented by the M.H.C class II molecule.

Detection of specific antibodies may be carried out using conventional techniques such as sandwich assays, etc. Western blotting or other antibody-based recognition system may be used.

According to the fourth embodiment of the invention, the autoimmune disease is diagnosed by detecting, in a biological sample, SAg activity specifically associated with the autoimmune disease. This is done by carrying out a functional assay in which a biological fluid sample containing MHC class II+ cells, for example Antigen Presenting Cells (APC) such as dendritic cells is contacted with cells bearing one or more variable β-T-receptor chains and detecting preferential proliferation of the Vβ subset characteristic of said autoimmune disease. Typically, this method of diagnosis is combined with one or more of the methods (I), (II), (III) as described earlier to maximise specificity.

The biological sample according to this variant of the invention is typically blood and necessarily contains MHC class II+ cells such as B-lymphocytes, monocytes, macrophages or dendritic cells which have the capacity to bind the superantigen and enable it to elicit its superantigen activity. MHC class II content of the biological sample may be boosted by addition of agents such as IFN-gamma.

The biological fluid sample is contacted with cells bearing the Vβ-T receptors belonging to a variety of different families or subsets in order to detect which of the Vβ subsets is stimulated by the putative SAg, for example V-β2, 3, 7, 8, 9 13 and 17. Within any one V-β family it is advantageous to use V-β chains having junctional diversity in order to confirm superantigen activity rather than nominal antigen activity.

The cells bearing the V-β receptor chains may be either an unselected population of T-cells or T-cell hybridoma. If unselected T-cells are used, the diagnostic process is normally carried out in the following manner : the biological sample containing MHC Class II+ cells is contacted with the T-cells for approximately 3 days. A growth factor such as Interleukin 2 (IL-2) which selectively amplifies activated T-cells is then added. Enrichment of, a particular V-β family or families is measured using monoclonal antibodies against the TCR-β-chain. Only amplified cells are thus detected. The monoclonal antibodies are generally conjugated with a detectable marker such as a fluorochrome. The assay can be made T-cell specific by use of a second antibody, anti CD3, specifically recognizing the CD3-receptor.

Figure 9:
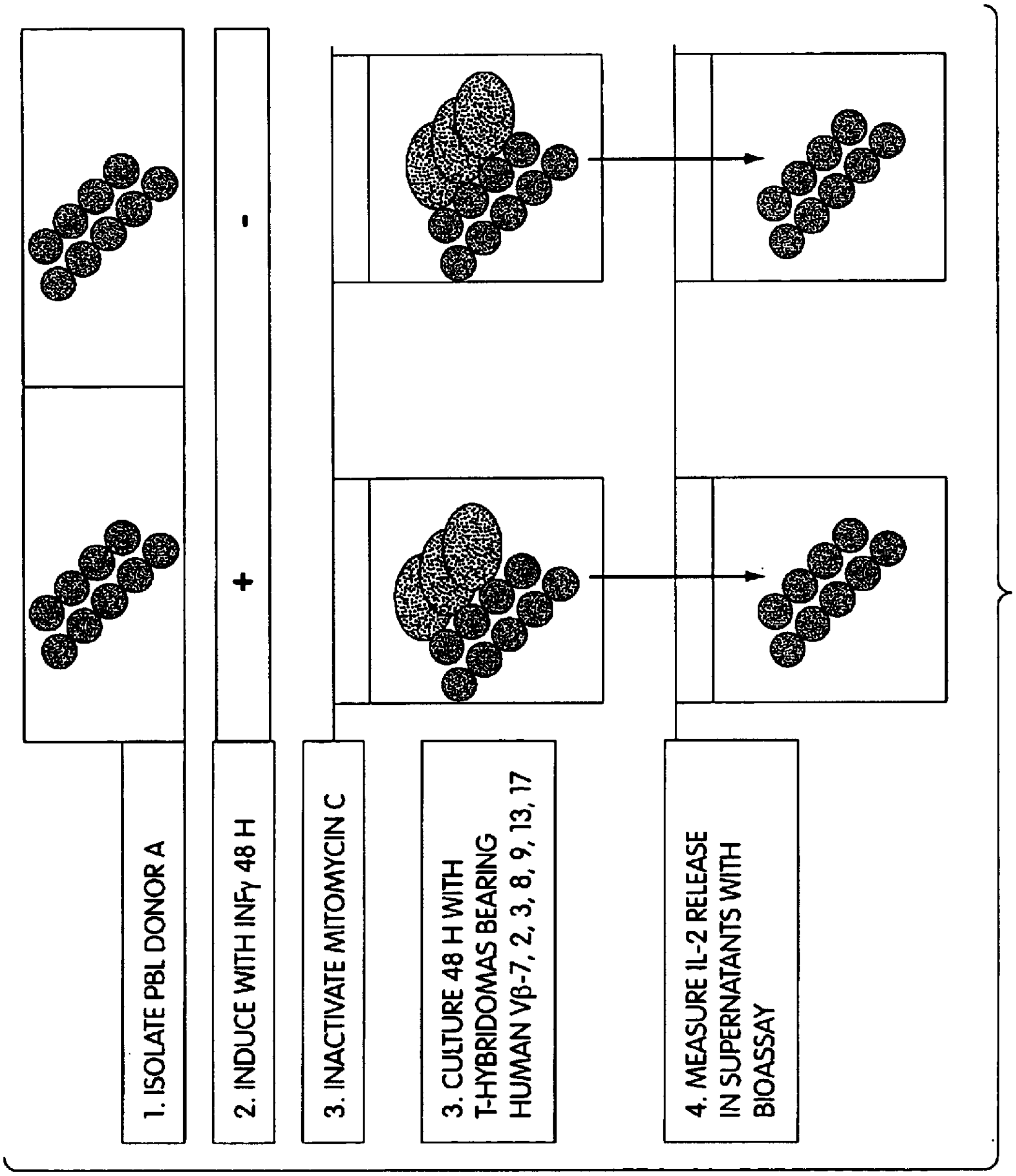

T-cell hybridoma bearing defined T-cell receptor may also be used in the functional or cell-based assay for SAg activity. An example of commercially available cells of this type are given in B. Fleischer et al. *Infect. Immun.* 64, 987–994, 1996. Such cell-lines are available from Immunotech, Marseille, France. According to this variant, activation of a particular family of V-β hybridoma leads to release of IL-2. IL2 release is therefore measured as read-out using conventional techniques. A specific example of this procedure for diabetes is illustrated in FIG. 9. The basic methodology is adapted for other autoimmune diseases by employing T-cell receptor cells of the appropriate type for that disease.

For diabetes, detection of SAg activity will normally lead to preferential proliferation of the V-β7 subset. For other autoimmune diseases, other V-β subsets may be proliferated.

According to another aspect of the present invention, there is provided human endogenous retroviruses having superantigen activity and being associated with human auto immune disease Such retroviruses which may be of the HERV-K family, or otherwise, are obtainable from RNA prepared from a biological sample of human origin, by carrying out the following steps:

i) isolation of the 5' R-U5 ends of expressed putative retroviral genomes using nucleic acid amplification, the 3' primer being complementary to known <primer binding sites> (pb);

ii) isolation of the 3' R-poly(A) ends corresponding to the 5' R-U5 ends, by use of primers specific for the R regions isolated in step i);

iii) amplification of the conserved RT-RNase H region within the pol gene by using degenerate primers corresponding to the conserved region;

iv) amplification of the 5' moiety of the putative retroviral genome by using primers specific for the different U5 regions isolated in step i) in conjunction with a primer specific for the 3' end of the central pol region isolated in step iii);

v) amplification of the 3' moiety of the putative retroviral genome using primers specific for the central pol region isolated in step iii) in conjunction with primers specific for the poly(A) signals present in the 3' R-poly(A) sequences isolated in step ii);

vi) confirmation of the presence of an intact retroviral genome by amplification using primers specific for its predicted U5 and U3 regions.

A preferred human endogenous retrovirus of the invention is IDDMK 1,2 22 comprising each of the sequences illustrated in FIGS. 7A, 7B, 7C or sequences having at least 90% identity with these sequences, and further comprising GAG-encoding sequences, and sequences encoding POL as shown in FIG. 7H. This retrovirus has a size of approximately of 8.5 kb, has SAg activity encoded within the Env region as shown in FIG. 7C and 7E and gives rise to V-β7 specific proliferation.

The invention also relates to proviral DNA of a retrovirus having superantigen activity and being associated with an autoimmune disease. Such proviral DNA is naturally found integrated into the human genome. The proviral DNA may be obtained from a biological sample of human origin by:

i) obtaining retroviral RNA according to the method of claim 13, and further, ii) generating a series of DNA probes from the retroviral RNA obtained in i);

iii) hybridising under stringent conditions, the probes on a genomic human DNA library;

iv) isolation of the genomic sequences hybridising with the probes.

The invention also relates to nucleic acid molecules (RNA, DNA or cDNA) comprising fragments of the retroviral RNA or DNA described above, having at least 20 nucleotides and preferably at least 40. The fragments may be specific for a given retrovirus, specific signifying a homology of less than 20% with other human or non-human retroviruses.

Preferred nucleic acid molecules of the invention encode SAg activity particularly SAg activity, responsible for the proliferation of autoreactive T-cells. If the region of the viral genome encoding the SAg activity is unknown, the particular region may be identified by:

i) transfecting expressed retroviral DNA or portions thereof into MHC Class $II^+$ antigen presenting cells under conditions in which the viral DNA is expressed, ii) contacting the MHC class $II^+$ transfectants with cells bearing one or more defined (V)-β T-cell receptor chains, and iii) determining whether the transfectant is capable of inducing preferential proliferation of a Vβ subset, the capacity to induce preferential proliferation being indicative of SAg activity within the transfected DNA or portion thereof. Proliferation may be measured by determination of 3H-thymidine incorporation (see Examples methods and materials).

The nucleic acid molecule encoding SAg activity may be derived from an endogenous human retrovirus. It typically corresponds to an open reading frame of the retrovirus and may contain at least one internal stop codon or may be a synthetic mutant in which 1 or 2 nucleotides have been added or deleted to remove the stop codon and modify the reading frame.

Preferably, the nucleic acid of the invention comprises or consists of all or part of the env gene (encoding the envelope glycoprotein) of an endogenous human retrovirus associated with autoimmune disease. The env—encoded protein is particularly likely to have SAg activity, as exemplified by the IDDM HERV. Synthetic or recombinant nucleic acids corresponding to the env genes or fragments thereof are also within the scope of the invention.

The nucleic acid molecules of the invention may comprise ribozymes or antisense molecules to the retrovirus involved in autoimmune disease.

The invention also relates to nucleic acid molecules capable of hybridizing in stringent conditions with retroviral DNA or RNA. Typical stringent conditions are those where the combination of temperature and salt concentration chosen to be approximately 12–20° C. below the Tm (melting temperature) of the hybrid under study.

Such nucleic acid molecules may be labelled with conventional labelling means to act as probes or, alternatively, may be used as primers in nucleic acid amplification reactions.

Preferred nucleic acid molecules of the invention are illustrated in FIGS. 7A, 7B, 7C, 7D, 7E, 7G and also encompass nucleic acid sequences encoding the POL protein shown in FIG. 7H, and the GAG protein. Sequences exhibiting at least 90% homology with any of the afore-mentioned sequences are also comprised within the invention or fragments of any of these sequences having at least 20 and preferably at least 30 nucleotides.

The Env encoding sequence shown in FIG. 7C is particularly preferred, as well as the nucleic acid encoding the Env/F-S SAg protein shown in FIGS. 7G and 7E. A preferred nucleic acid molecule is a molecule encoding the Env/F-S Sag protein wherein the first internal stop codon (shown underlined in FIG. 7C), is mutated by insertion of an extra T (at position 517 in FIG. 7G underlined) to eliminate premature translational stop, the resulting sequence being then in the correct reading frame to encode the COOH terminal extension (shown underlined in FIG. 7G). This protein arises naturally from read-through together with a −1 frame shift, but this process is inefficient. The synthetic T'-inserted cDNA provides an efficient way of producing the SAg molecule shown in FIG. 7G. The single reading frame in this <synthetic> molecule thus corresponds to two different reading frames separated by a stop codon in the natural molecule. Nucleic acid molecules encoding an HERV env and including minus 1, plus 1 frameshifts and termination suppression (0 frames are thus particularly preferred embodiments of the invention.

The invention further relates to proteins expressed by human endogenous retroviruses having SAg activity and being associated with human autoimmune Fez disease. Peptides or fragments of these proteins having at least 6 and preferably at least 10 aminoacids, for example 6–50 or 10–30 amino acids, are also included within the scope of the invention. Such proteins may be Gag, Pol or Env proteins or may be encoded by any Open Reading Frame situated elsewhere in the viral genome. These proteins may or may not present SAg activity. Particularly preferred proteins of the invention have SAg activity. Examples of SAg proteins of the invention are proteins encoded by the env gene of HERV, for example that shown in FIG. 7G.

The proteins having SAg activity may naturally result from a premature translational stop and possibly also from a translational frameshift. Endogenous retroviral ORFs typically contain a number of internal stop codons, which often render the HERV defective. It has been discovered by the present inventors that, in some cases, retroviral expression products having SAg activity result from read-through transcription of the ORF, possibly also accompanied by a reading frame shift. Consequently, the proteins exhibiting SAg activity are not, in these cases, the expected expression products of the retrovirus.

It may therefore be deduced that open reading frames of retroviruses associated with human autoimmune disease which contain at least one internal translational stop codon are among potential candidates for SAg activity. The proteins produced by premature translational stop may have an additional carboxy-terminal extension resulting from translational frame shift, for example −1 or −2 or +1 or +2 translational frame shift. Such a protein is illustrated in FIG. 7G. Further preferred proteins of the invention are the proteins encoded by synthetic cDNA, corresponding to the in-frame fusion of two normally different reading frames, together with mutation of the internal stop codon. These artificial open-reading frames are made by inserting or deleting one or two nucleotides in the coding sequence at the site where frame-shift occurs naturally, thus <correcting> the reading frame and enabling efficient production of a protein which is naturally only produced very inefficiently.

Other proteins of the invention are those comprising the aminoacid sequences shown in FIG. 7D, 7F, 7H or an aminoacid sequence having at least 80% and preferably at least 90% homology with the illustrated sequences or fragments of these sequences having at least 6 and preferably at least 10 aminoacids. The proteins of the invention may be made by synthetic or recombinant techniques.

The invention also relates to antibodies capable of specifically recognizing a protein according to the invention. These antibodies are preferably monoclonal. Preferred antibodies are those which specifically recognize a retroviral protein having SAg activity and which have the capacity to block SAg activity. The capacity of the antibody to block SAg activity may be tested by introducing the antibody under test into an assay system comprising:

i) MHC Class II$^+$ cells expressing retroviral protein having SAg activity and ii) cells bearing Vβ-T cell receptor chains of the family or families specifically stimulated by the HERV SAg expressed by the MHC Class II$^+$ cells, and determining the capacity of the substance under test to diminish or block Vβ-specific stimulation by the HERV Sag.

The steps described below involve the use of Sag-expressing transfectant cells such as those described in the examples, to inhibit the effect of Sag in vitro and in vivo. The example applies to the Sag expressed by the IDDM-associated HERV, as well as to other Sags, encoded by HERV associated with other autoimmune diseases, such as multiple sclerosis, and previously identified as Sag by a functional T cell activation assay as described earlier.

Mabs directed against the Sag protein (or portion of it) are generated by standard procedures used to generate antibodies against cell surface antigens. Mice are immunised with mouse cells expressing both Sag and MHC class II (such as a. Sag-transfected mouse B cell line described in the examples below). After fusion with hybridoma cell lines, supernatants are screened for the presence of anti-Sag antibodies on microtiter plates for reactivity to Sag transfectants cells, with non-transfected cells as negative controls. Only Mabs with reactivity specific for Sag expressing cells are selected.

All such Mabs, either as culture supernatants or as ascites fluid, are then tested for their ability to block the Sag activity, as assayed by the T cell assay in the presence of Sag-expressing human MHC class II positive transfectants, as described in Example 4 below. A preferred version of this assay makes use of Vβ-specific hybridomas as T cell targets for read out. Controls are blocking of the same assay by anti-HLA-DR Mabs, which is known to inhibit the Sag effect on T cell activation. Mabs capable of efficiently blocking the Vβ-specific Sag effect, when tested at several dilutions, are selected as anti-Sag blocking Mabs.

As well as monoclonal antibodies capable of inhibiting IDDM Sag, this generation and selection of anti-Sag blocking Mabs can be achieved in the case of any HERV-encoded Sag associated with other autoimmune diseases, once such a HERV-encoded Sag has been demonstrated.

Sufficient numbers of anti-Sag Mabs are screened in the functional assay to identify anti-Sag Mabs with optimal Sag blocking activity, in terms of T cell activation (see for example FIG. 9). Selected Sag blocking Mabs are then converted into their <humanised> counterpart by standard CDR grafting methodology (a procedure performed for a fee under contract by numerous companies). A humanised anti-Sag blocking Mab, directed against the IDDM associated Sag or against any Sag encoded by another HERV associated with autoimmunity, can then be tested clinically in patients. In the case of IDDM, early diagnosed patients are selected and protection against progressive requirement for insulin therapy is followed as an index of efficacy. In the case of other autoimmune diseases, efficacy of the anti-Sag Mab is followed with reference to the relevant clinical parameters.

The invention also relates to cells transfected with and expressing human endogenous retrovirus having SAg activity and being associated with a human autoimmune disease. The cells may be preferably human cells other than the naturally occurring cells from auto-immune patients and may also include other type of eukaryotic cells such as monkey, mouse or other higher eukaryotes. The cells may be established cell-lines and are preferably MHC class II$^+$, or MHC II$^+$-inducible, such as β-lymphocytes and monocytes. Non-human higher eukaryotic cell-lines (e.g. mouse) stably transfected with the HERV Sags of the invention (as exemplified in Example 6 below) have been found to specifically stimulate in vitro human vβ-T cells of the specificity normally associated with the HERV Sag in vivo. The stimulation is coreceptor independent (CD4 and CD8). This specific T-cell stimulation can also be observed in vivo upon injection of the transfectants into non-human animals. A transgenic animal model for the human autoimmune disease is therefore technically feasible. The transgenic animal is made according to conventional techniques and includes in its genome, nucleic acid encoding the HERV Sags of the invention.

A further important aspect of the invention relates to the identification of substances capable of blocking or inhibiting SAg activity. These substances are used in prophylactic and therapeutic treatment of autoimmune diseases, involving retroviral SAg activity. The invention thus concerns methods for treating or preventing autoimmune disease, for example IDDM, by administering effective amounts of substances capable of blocking Sag activity associated with expression of a human endogenous retrovirus. The substances may be antibodies, proteins, peptides, derivatives of the HERV, derivatives of the Sag or small chemical molecules. The invention also relates to pharmaceutical compositions comprising these substances in association with physiological acceptable carriers, and to methods for the preparation of medicaments for use in therapy or prevention of autoimmune disease using these substances.

Further, this aspect of the invention includes a process for identifying substances capable of blocking or inhibiting SAg activity of an endogenous retrovirus associated with autoimmune disease, comprising introducing the substance under test into an assay system comprising:

i) MHC Class II$^+$ cells functionally expressing retroviral protein having SAg activity and;

ii) cells bearing Vβ-T cell receptor chains of the family or families specifically stimulated by the HERV SAg expressed by the MHC Class II$^+$ cells, and determining the capacity of the substance under test to diminish or block Vβ-specific stimulation by the HERV SAg, The cells bearing the β-T cell receptors and the MHC Class II+ cells may be those described earlier. Read-out is IL-2 release.

The substances tested for inhibition or blockage of Sag activity in such screening procedures may be proteins, peptides, antibodies, small molecules, synthetic or naturally occurring, derivatives of the retroviruses themselves, etc. Small molecules may be tested in large amounts using combinatorial chemistry libraries.

The screening procedure may include an additional preliminary step for selecting substances capable of binding to retroviral protein having SAg activity. This additional screening step comprises contacting the substances under test, optionally labelled with detectable marker with the retroviral protein having SAg activity and detecting binding.

The Sags of the invention or a portion thereof may be used for the identification of low molecular weight inhibitor molecules as drug candidates.

The rational is that because HERV encoded Sags are the product of ancient infectious agents, they are not indispensable to humans and can thus be inhibited without adverse side effects Inhibitors of Sag, as potential drug candidates, are preferably identified by a two step process:

In the first step, compatible with large scale, high throughput, screening of collections (<libraries>) of small molecular weight molecules, the recombinant Sag protein (or portion of it) is used in a screening assay for molecules capable of simply binding to the Sag protein (=<ligands>). Such high throughput screening assays are routinely performed by companies such as Novalon Inc or Scriptgen Inc, and are based either on competition for binding of peptides to the target protein or on changes in protein conformation induced by binding of a ligand to the target protein. Such primary high throughput screening for high affinity ligands capable of binding to a target recombinant protein are available commercially, under contract, from such companies .as Novalon or Scriptgen. This screening method requires that a HERV protein with Sag activity, and knowledge of such an activity, be available.

In the second step, any low molecular weight molecule identified as described above as capable of binding to the Sag protein, is tested in the functional Sag assay consisting of human MHC class II positive Sag transfectants and responding Vβ-specific T cells (preferably hybridomas), as described herein. Positive control for Sag inhibition is an anti-HLA-DR Mab, known to inhibit the Sag effect. All candidate molecules are thus tested, at different concentrations, for a quantitative assessment their anti-Sag inhibitory efficacy.

This example can apply to the Sag encoded by the IDDM-associated HERV described herein, as well as to any other Sag discovered to be encoded by another HERV associated with another autoimmune disease.

This screening procedure relies upon the availability of a Sag and of a Sag functional assay according to the invention, but it otherwise relies on commercially available steps. Compounds exhibiting anti-Sag inhibitory effects are then tested for obvious toxicity and pharmacokinetcs assays, in order to determine if they represent valuable drug candidates.

Once a substance or a composition of substances has been identified which is capable of blocking or inhibiting SAg activity, its mode of action may be identified particularly its capacity to block transcription or translation of SAg encoding sequences. This capacity can be tested by carrying out a process comprising the following steps:

i) contacting the substance under test with cells expressing retroviral protein having SAg activity, as previously defined, and ii) detecting loss of SAg protein expression using SAg protein markers such as specific, labelled anti-SAg antibodies.

The antibodies used in such a detection process are of the type described earlier.

The invention also relates to a kit for screening substances capable of blocking SAg activity of an endogenous retrovirus associated with an autoimmune disease, or of blocking transcription or translation of the retroviral SAg protein. The kit comprises:

MHC Class $II^+$ cells transformed with and expressing retroviral SAg according to the invention;

cells bearing Vβ T-cell receptor chains of the family or families specifically stimulated by the HERV SAg;

means to detect specific Vβ stimulation by HERV SAg;

optionally, labelled antibodies specifically binding to the retroviral SAg.

According to a further important aspect of the invention, there is provided a protein or peptide derived from an autoimmune related retroviral SAg as previously defined wherein the protein is modified so as to be essentially devoid of SAg activity, thereby no longer being capable of significantly activating auto-reactive T-cells. Such modified proteins are however capable of generating an immune response against SAg, the immune response involving either antibodies and/or T-cells responses. The immunogenic properties of the modified proteins are thus conserved with respect with the authentic SAg.

Such modified immunogenic proteins may be obtained by a number of conventional treatments of the SAg protein, for example by denaturation, by truncation or by mutation involving deletion, insertion or replacement of aminoacids. Modified SAg proteins being essentially devoid of SAg activity but capable of generating an immune response against SAg include the truncations of the SAg protein, either at the amino or carboxyterminal, and may involve truncations of about 5–30 aminoacids at either terminal. A preferred example with respect to the IDDMK 1.2-22 SAg encoded by the Env gene illustrated in FIG. 7, particularly in FIG. 7E and FIG. 7G, are amino and carboxy terminal truncations of the protein shown in FIG. 7G, for example truncations of 5, 10, 15, 20, 25 or 30 amino acids. An example of a C-terminal truncation of the IDDMK 1.2-22 SAg protein is the protein shown in FIG. 7D, involving a truncation of 28 amino acids. The modified protein may be obtained by recombinant or synthetic techniques, or by modifying naturally occuring SAg proteins, for example by physical or chemical treatment.

These proteins are used in the framework of the invention as vaccines, both prophylactic and therapeutic, against autoimmune disease associated with retroviral SAg. The vaccines of the invention comprise an immunogenically effective amount of the immunogenic protein in association with a pharmaceutically acceptable carried and optionally an adjuvant. The use of these vaccine compositions is particularly advantageous in association with the early diagnosis of the autoimmune disease using the method of the invention. The invention also includes the use of the immunogenic proteins in the preparation of a medicament for prophylactic or therapeutic vaccination against autoimmune diseases.

The rational behind this prospective immunisation technique is that because HERV encoded Sags are the product of ancient infectious agents, they are not indispensable to humans and can thus be inhibited without adverse side effects.

Identification of suitable anti-sag vaccine proteins or peptides can be made in the following way. Modified forms of the original active Sag protein, including truncated or mutated forms, or even specific peptides derived from the Sag protein, are first tested in the functional Sag assays described above to confirm that they have lost all Sag activity (in terms of T cell activation). These modified forms of Sag are then used to immunise mice (or humans) by standard procedures and with appropriate adjuvants. Extent and efficacy of immunisation, is measured, including circulating anti-Sag antibodies. In a preferred example, eliciting a B cell immune response, by selecting B cell epitopes from the Sag protein as immunogen, is deliberately aimed at.

Successfully immunised animals are then tested for the effect of Sag in vivo by a standard assay, namely the injection of MHC class II positive Sag transfectants (such as the transfectants described in the examples below), known to induce in vivo a Vβ-specific T cell activation. Successful immunisation against a Sag protein is expected to result in a reduction or in a block of the in vivo Sag-induced T cell activation and proliferation in effectively immunised individuals. This procedure is referred to as anti-Sag vaccination. Immunisation against Sag can be performed in humans, for diabetes, preferably initially in the case of early diagnosed IDDM patients. Efficacy of this novel a <vaccination> procedure is monitored by clinical outcome and by reduction of the expected requirements for insulin therapy. In the case of other. Sags, encoded by HERV associated with autoimmune diseases other than diabetes, the clinical outcome is monitored accordingly.

The vaccines of the invention can be prepared as injectables, e.g. liquid solutions or suspensions. Solid forms for solution in, or suspension in, a liquid prior to injection also can be prepared. Optionally, the preparation also can be emulsified. The active antigenic ingredient or ingredients can be mixed with excipients which are pharmaceutically acceptable and compatible with the active ingredient. Examples of suitable excipients are water, saline, dextrose, glycerol, ethanol, or the like, and combinations thereof. In addition, if desired, the vaccine can contain minor amounts of auxiliary substances such as wetting or emulsifying agents, pH buffering agents, or adjuvants such as aluminium hydroxide or muramyl dipeptide or variations thereof. In the case of peptides, coupling to larger molecules (e.g. KLH or tetanus toxoid) sometimes enhances immunogenicity. The vaccines are conventionally administered parenterally, by injection, for example, either subcutaneously or intramuscularly. Additional formulations which are suitable for other modes of administration includes suppositories and, in some cases, oral formulations.

The vaccines of the invention also include nucleic acid vaccines comprising nucleic acid molecules encoding the human retroviral Sag or modified forms of the SAg known to be immunogenic but no longer active as SAgs. The nucleic acid vaccines, particularly DNA vaccines, are usually administered in association with a pharmaceutically acceptable carrier as an intra-muscular injection.

The invention also relates to use of substances inhibiting either the retroviral function or the SAg function of the associated retroviruses, or Sag synthesis, in therapy for autoimmune diseases. These substances may be identified by the screening procedures described herein.

The invention further relates to methods for treatment or prevention of autoimmune, diseases comprising administering an effective amount of a substance capable of inhibiting retroviral function or a substance capable of inhibiting SAg activity or synthesis.

An examples of compounds inhibiting retroviral function is AZT. Examples of compounds or substances capable of inhibiting SAg activity are antibodies to Sag, or ribozymes or antisense molecules to the SAg-encoding nucleic acid, or small molecules identifiedby virtue of their ability to inhibit SAg.

The invention also relates to a an exploratory process for detecting human autoimmune disease associated with expression of unidentified human retrovirus Superantigen (SAg), said process comprising at least one of the following steps:

i) detecting the presence of any expressed retrovirus in a biological sample of human origin;

ii) detecting the presence of SAg activity in a biological sample of human origin containing MHC Class $II^+$ cells.

This process can be used as a preliminary indication of the involvement of retroviral superantigens in autoimmune disease.

Different aspects of the invention are illustrated in the figures.

FIG. 1. Leukocytes from IDDM-patients release Reverse Transcriptase (RT) activity.

(A) Supernatants derived from cultured islets isolated from two patients (Conrad et al., 1994) were assayed for RT-activity, using a half-logarithmic dilution series of purified murine leukemia virus (MLV) RT as a standard (Pyra et al., 1994). Results are expressed as mean +/−1 SD. Islets and spleen cells from non-diabetic organ donors were cultured either alone, in the presence or absence of mitogen (−/+), or together in mixed allogeneic cultures (time as days in culture prior to collection of the supernatant is indicated below the bars).

(B) Islets and spleen cells from three non diabetic organ donors, from the two patients with acute-onset IDDM, and two patients with chronic IDDM (Conrad et al., 1994) were cultured for 1 week and supernatants were analyzed for the presence of RT-activity. Results are expressed as mean +/−1 SD for at least three individual measurements.

FIG. 2A. Isolation of a single full length retroviral genome, $IDDMK_{1,2}22$, with a six step procedure.

1) cPBS primers ($Lys_{1,2}$, $Lys_3$, Pro, Trp) were used to perform a 5' RACE 2) the eight 5' R-U5 sequences obtained in 1) were used to perform a 3' RACE with primers annealing in the R 3) the conserved RT-RNAse H region was amplified with degenerate primers 4) the 5' moiety (the predicted size for full length HERV-K-retroviruses is 3.6 kb was amplified by PCR using primers specific for the eight 5' R-U5 sequences in conjunction with a primer specific for the 3' of the central pol region obtained in step 3. The primer specific for the $K_{1,2}22$ 5' consistently yielded a fragment of this size, 5) the 3' the predicted size for HERV-K-retroviruses is 5 kb) was amplified by PCR using a primer specific for the 5' of the central pol region isolated in step 3 and primers specific for the coly(A) signals present in the 3' R-poly(A) sequences obtained in step 2. The PCR reaction using a primer specific for the 3' clone $K_{1,2}22$ (amplified in step 4) consistently yielded a fragment potentially presenting an intact 3' HERV-K moiety of 5 kb, 6) the presence of an intact 8.6 kb retroviral genome containing the overlapping 5' and 3' moieties isolated in steps 4 and 5 was confirmed by using primers specific for its predicted U5 and U3 regions.

FIG. 2B. Consensus features of retroviral 5' end sequences (termed STRs). These consensus features are valid for retroviruses with a polyadenylation signal in the R (repeat) region. The R region is characterized by the AATAAA or ATTAAA polyadenylation signal (bold) followed by 13 to 20 nucleotides and the dinucleotide CA or GA (bold) at the 3' end of the R region. The beginning of U5 region is defined by a GT- or T-rich sequence (underlined). The 3' end of the U5 region is in all known retroviruses defined by the dinucleotide CA, followed by one, two or three nucleotides and the primer-binding site (PB)—(N) stands for nucleotide, the suffixes x, y, and z for an undefined number.

Figure 2C:
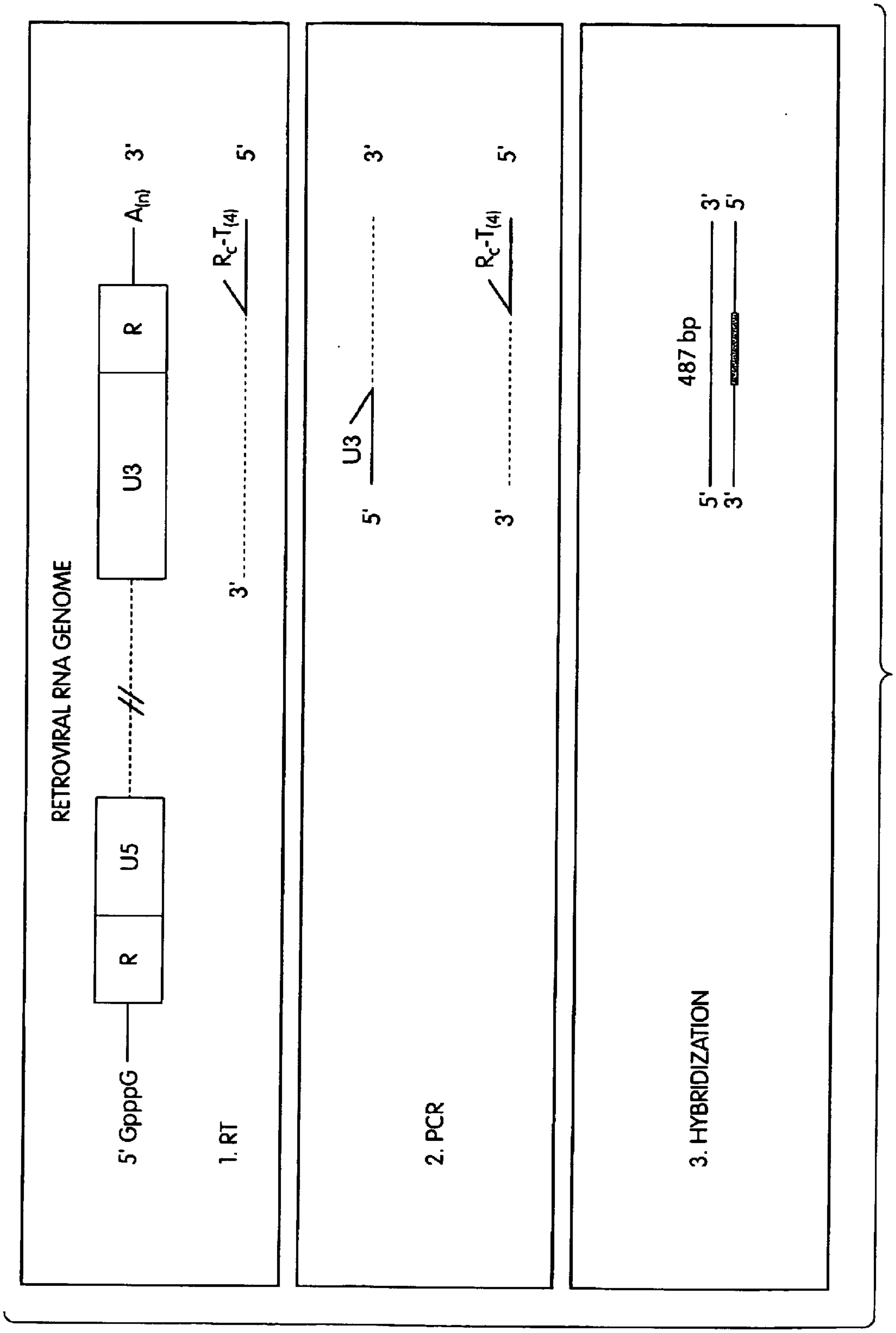

FIG. 2C. Schematic representation of mRNA-specific PCR of IDDMK$_{1,2}$-22 using a poly (A)-specific probe (Rc-T$_{(4)}$). Details of this technique are given in the <Experimental Procedure> Section of the Examples. This procedure results in a Reverse-Transcriptase-dependent amplification of retroviral genomes. The products generated can be diminished below background by RNAse treatment.

Figure 2D:
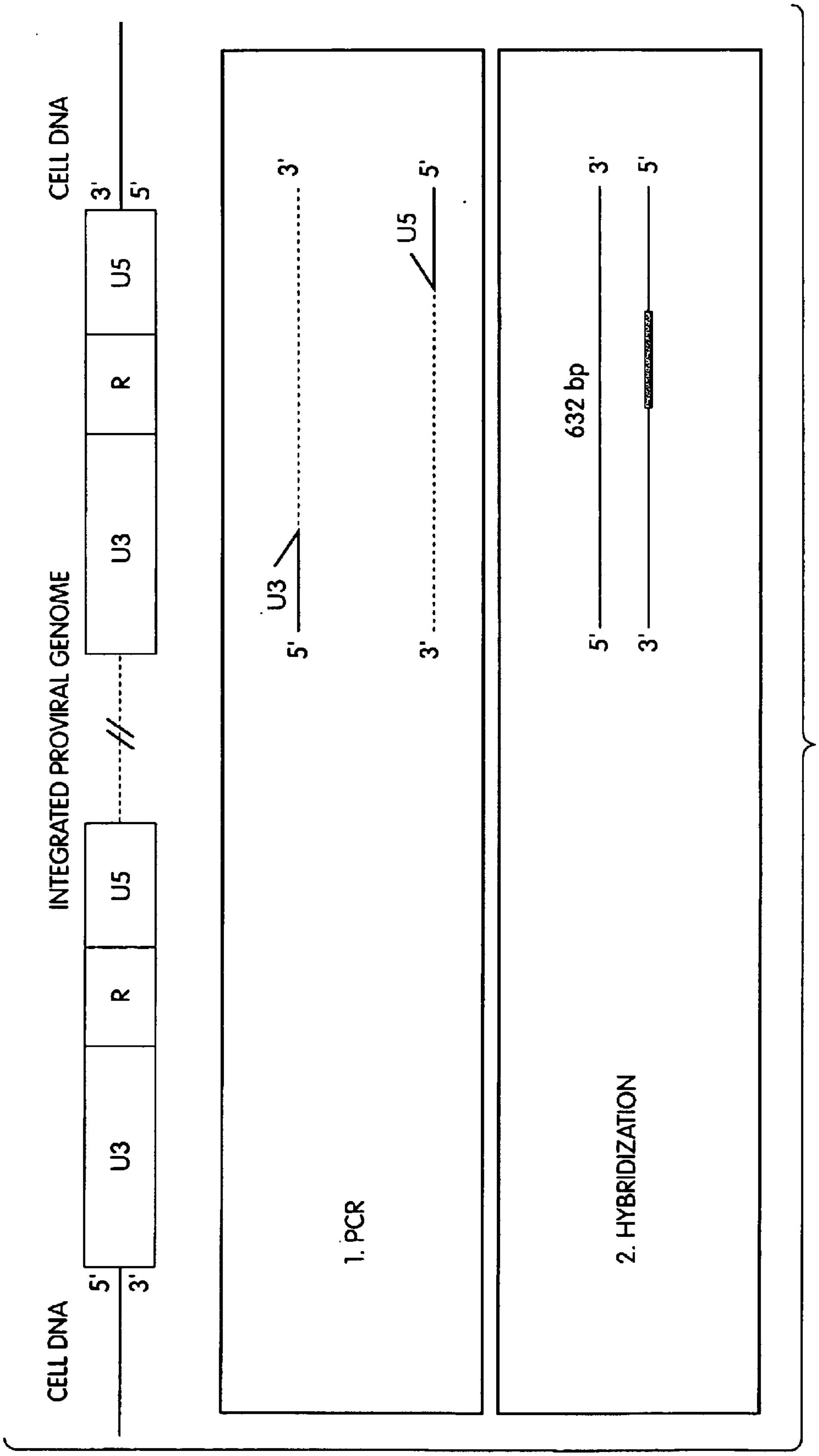

FIG. 2D. Schematic representation of IDDMK$_{1,2}$-22 Provirus-specific PCR. The procedure specifically amplifies proviral 5' and 3' LTRs (long terminal repeats).

The primers used in an RT- control are substituted with either U5-primers 1) 5' ATC CAA CCA Tga Ag 3' (SEQ ID NO:2) 2) 5' TCT Cgt Aag gTg CAA Atg Aag 3' (SEQ ID NO:3) at 0.3 $\mu$M final concentration in conjunction with the U3-primers using either 3) gTA Aag gAT CAA gTg Ctg TgC 3' (SEQ ID NO:4) or 4) 5' CTT TAC AAA gCA gTA Ttg Ctg C 3' (SEQ ID NO:5) at 0.3 $\mu$M final concentration. 0.5 $\mu$l of Taq- Pwo- polymerase mix (Boehriner Mannheim, Expand™ High Fidelity. PCR System) are used with a thermocycler profile corresponding to the one described for mRNA-specific RT-PCR and omitting the RT step.

Hybridization is performed with the probe and the methods corresponding those used for mRNA-specific RT-PCR.

Sequence identity is confirmed by sequencing according to standard procedures.

Figure 2E:
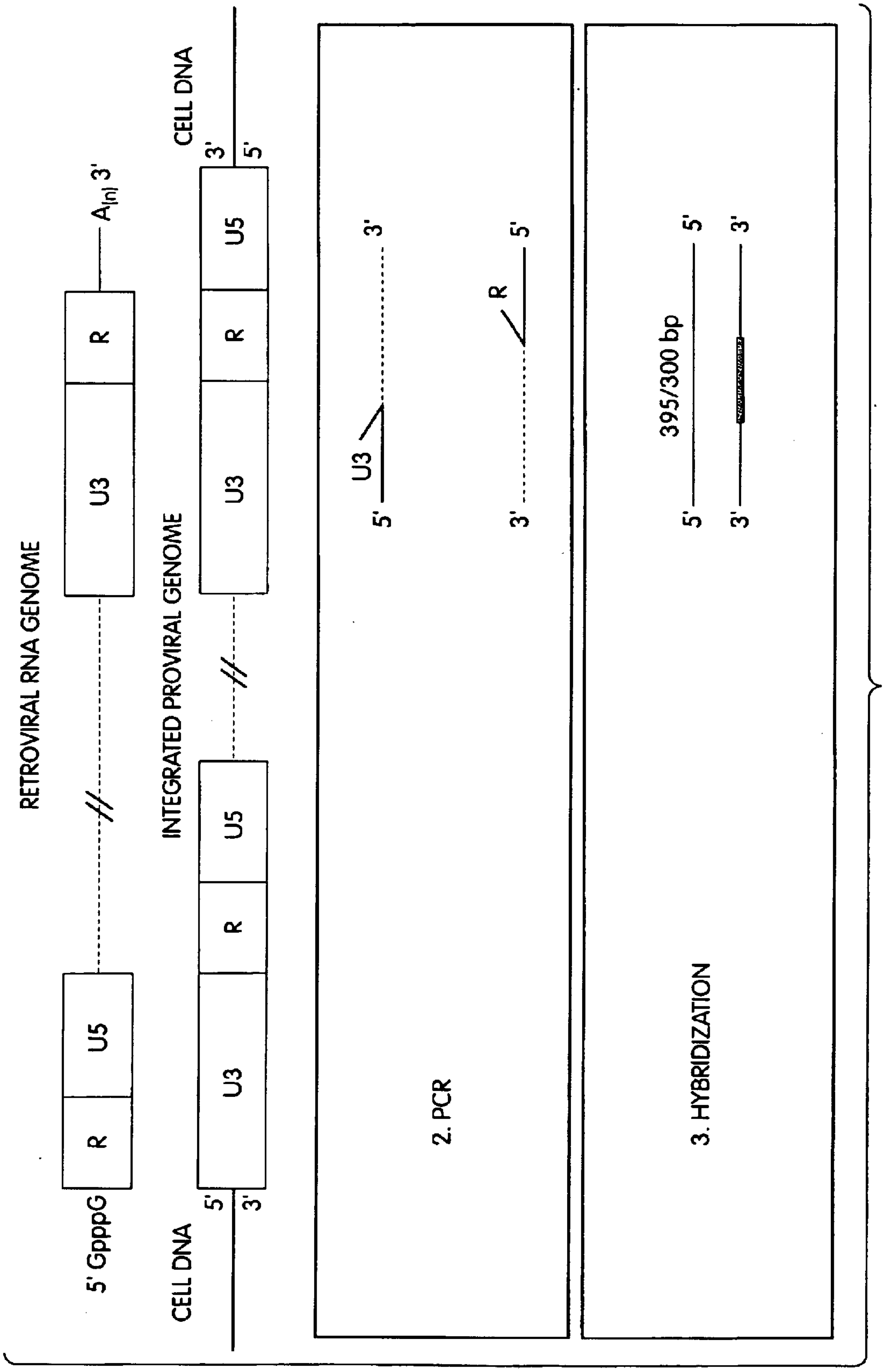

FIG. 2E. IDDMK$_{1,2}$-22 RNA- and Provirus-specific PCR. This procedure will result in amplification products independentely of the presence or absence of RT-reactions and reflects the total retroviral RNA- and DNA- templates present in a given sample.

The same conditions as in the proviral specific PCR are used with U3 primers 1) 5' AAC ACT gCg AAA ggC CgC Agg 3' (SEQ ID NO:6) or 2) 5' Agg TAT TgT CCA Agg TTT CTC C 3' (SEQ ID NO:7) in conjunction with R (repeat) primers 3) 5' CTT TAC AAA gCA gTA T Ctg C 3' (SEQ ID NO:5) or 4)5' gTA Aag gAT CAA gTg Ctg TgC 3' (SEQ ID NO:4). Cycling conditions and primer concentrations are identical to those described For proviral specific PCR.

Figure 2F:
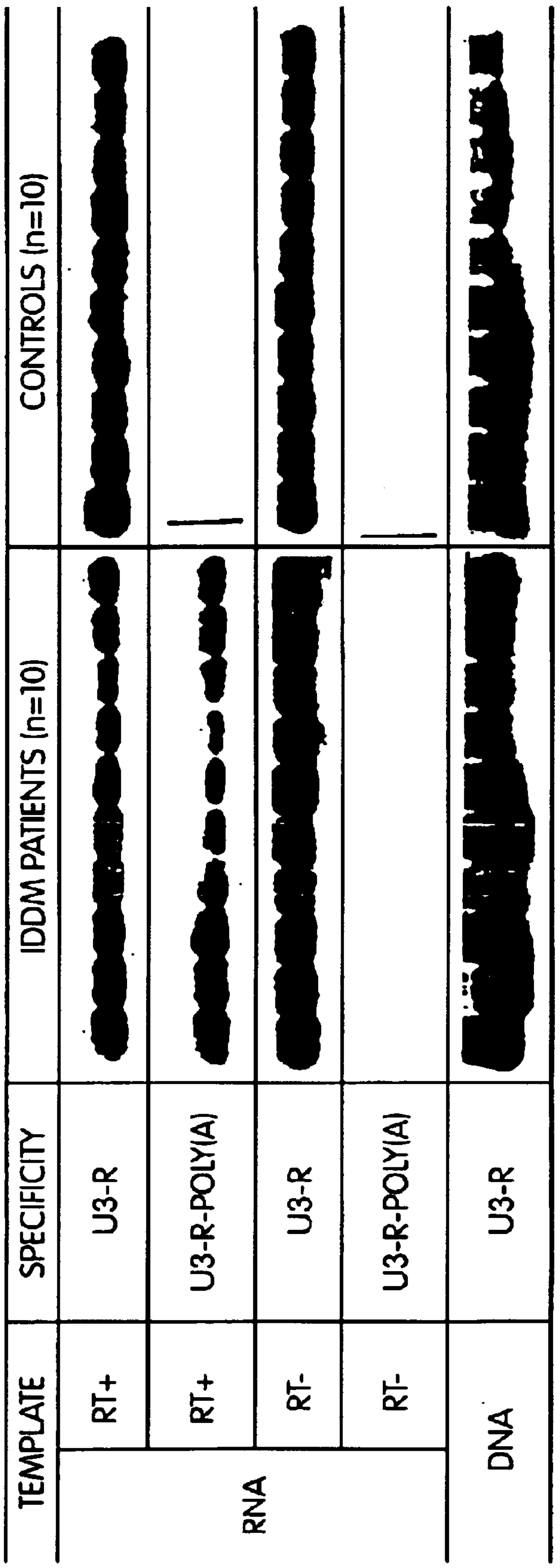

FIG. 2F. IDDMK$_{1,2}$22 is an endogenous retrovirus found in the plasma of IDDM patients at disease onset but not in the plasma of healthy controls.

PCR primers pairs were designed that are either specific for the U3-R- or for the U3-R-poly(A)-region of IDDMK$_{1,2}$22 (see Experimental Procedures). The U3-R primer pair amplified both viral RNA and DNA, whereas the U3-R-poly (A) primer pair amplified selectively viral RNA. The amplified material was hybridized with probes generated with the molecularly cloned U3-R region of IDDMK$_{1,2}$22. Signals in the first and third rows correspond to amplification of contaminating DNA present in the plasma of IDDM patients (left hand columns, 1–10) and controls (right hand columns, 1–10) and were as expected RT-independent. In contrast, signals in the second row resulted from the amplification of viral RNA present only in IDDM patients (left hand columns, 1–10) but not in the non diabetic controls (right hand columns, 1–10). This was supported by he absence of amplification products in reactions lacking RT (fourth row, right and left hand clumns, 1–10). In addition the signal could be diminished below background by RNAse treatment (data not shown). In the fifth row the genomic DNA from IDDM patients and controls was amplified with the U3-R-specific primers. The primer pair specific for the U3-R-poly (A), in turn, did not result in amplification of genomic DNA (data not shown).

FIG. 3. Phylogenetic trees of coding and non-coding regions place IDDMK$_{1,2}$22 in the HERV-K10 family of HERVs.

(A) IDDMK$_{1,2}$22 SU-ENV is most closely related to HERV-K10, and is also related to the B-type retroviruses MMTV and JSRV.

(B) The phylogenetic analysis of the RT region shows that IDDMK$_{1,2}$22 belongs to the HERV-K10 family and is more closely related to B-type retroviruses such as MMTV than to D-type retroviruses such as Simian Mason Pfizer (SMP) or Spumaviridae (SFV). Abbreviations used: SRV-2, Simian retrovirus; JSRV, Jaagsiekte Sheep retrovirus; SFV; Simian foamy virus).

(C) The non-coding LTR region was used to construct a phylogenetic tree of the HERV-K family. K$_{1,2}$1 and K$_{1,2}$4 (see above) were isolated only as subgenomic or truncated transcripts. K$_{1,2}$1 is related to KC4, while K$_{1,2}$4 and IDDMK$_{1,2}$22 are related to the K10/K18 subfamily. Within this family, K$_{1,2}$4 is closely related to K10, whereas IDDMK$_{1,2}$22 appears to be more distant.

FIG. 4. The pol-env-U3-R region of IDDMK$_{1,2}$22 exerts an MHC class II dependent but not MHC restricted mitogenic effect upon transfection in monocytes.

(A). IDDMK$_{1,2}$22 is expected to generate two singly spliced subgenomic RNAs, one encoding ENV, and one comprising the U3-R region. The episomal expression vector was engineered to carry a proximal SD downstream of the promoter (pPOL-ENV-U3). Thus, the two naturally expected subgenomic RNAs can also be generated.

(B) Monocytic cell lines do not express MHC class II surface proteins in the absence of induction by Interferon-g (INE-g), (reviewed by Mach et al., 1996). The monocyte cell line THP1 was transiently transfected with pPOL-ENV-U3 or with the expression vector alone (pVECTOR). Mitomycin C treated transfectants, either induced with INF-g for 48 h or non-induced (+/− INF-g, indicated below the x-axis) were cultured with MHC-compatible T cells at different responder: stimulator ratios as indicated below the graphs (T: APC). $^3$H-Thymidine incorporation was measured during the last 18 h of a 72 h culture and is given on the y-axis as n×10$^3$ cpm. Results are presented as mean +/−1 SD.

(C) The MHC class II transactivator CIITA mediates INF-g inducible MHC class II expression (reviewed by Mach et al., 1996). An integrative and stable THP1-CIITA transfectant (THP1-CIITA) was transfected with pVECTOR or pPOL-ENV-UR and was used in functional assays identical to those described in FIG. 4B.

(D) Peripheral blood lymphocytes (PEL) from healthy, MHC-unrelated donors (donors I, II and III indicated below the x-axis) were cultured with retroviral (PPOL-ENV-U3) and control transfectants (pVECTOR) at T: non-T ratios as indicated below the graphs (T: APC).

Figure 5A:
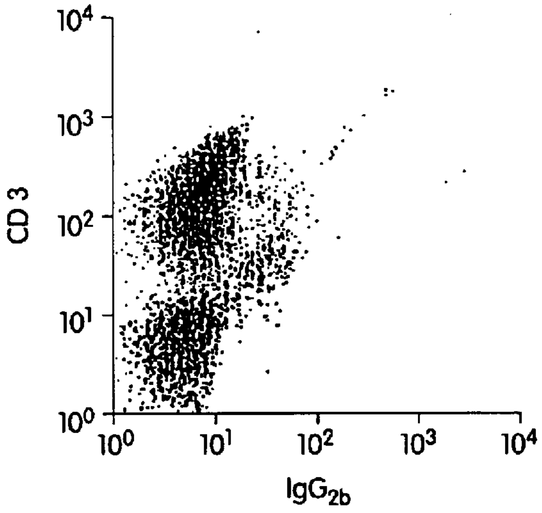
Figure 5B:
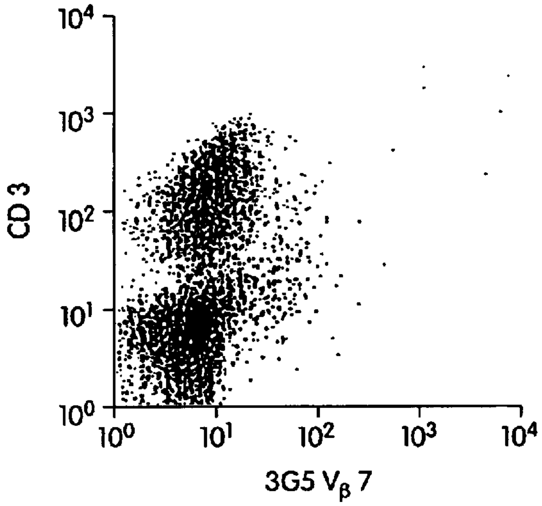
Figure 5C:
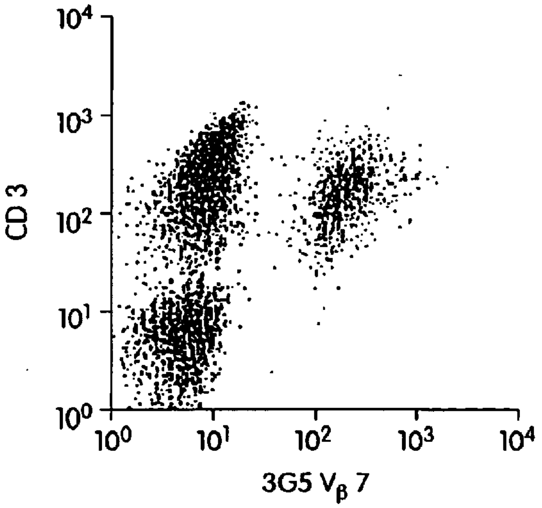

FIG. 5. TDDMK$_{1,2}$22 mediates a Vb 7-specific SAG-effect.

10$^6$ T cell/ml were cultured for 3 days with Mitomycin-treated pPOL-ENV-U3 and pVECTOR transfectants at T: non-T ratios as indicated. Twenty U/ml of recombinant IL-2 were then added to the cultures and FACS analysis performed after 3 to 4 days of expansion (Conrad et al., 1994).

(A) THP1 cells were transfected with pPOL-ENV-U3, the stimulated and expanded T cells were stained with anti-CD3 monoclonal antibodies and an isotype control after 7 days of coculture.

(B) T cells stimulated by THP1 transfected with the vector (pVECTOR) alone were stained with anti-CD3 monoclonal antibodies and the anti Vb 7-specific antibody 3G5.

(C) THP1 cells were transfected with pPOL-ENV-U3, the stimulated T cells were stained with anti-CD3 monoclonal antibodies and the anti Vb 7-antibody 3G5.

Table 1. IDDMK$_{1,2}$22 mediates a Vb 7-specific SAG-effect. The B lymphoblastoid cell line Raji was stably transfected with either pPOL-ENV-U3 or pVECTOR, and used in functional assays (equivalent to FIG. 5) 2 weeds after selection. The monocytic cell line HP1 was cultured for 48 flours after transfection with the same constructs. The percentages of double positive (CD3 and Vb-7, Vb-8, -12) T cells are indicated that were obtained after 1 week of coculture with the respective transfectants (pPOL-ENV-U3 or pVECTOR).

FIG. 6. The N-terminal env moiety of IDDMK$_{1,2}$22 mediates the SAG-effect.

(A). Based on the construct pPOL-ENV-U3 different deletional mutants were generated that comprised 1) pPOL: the pol gene; 2) pPOL-ENV/TR: the pol- and the N-terminal moiety of the env-gene; 3) pCI-ENV/TR: the N-terminal moiety of env-gene alone.

(B) PBL from MHC unrelated donors were cocultured with Mitomycin C treated THP1 cells as described in FIG. 4. The individual transfectants are indicated with the names of the constructs above the bars. (1) pVECTOR, 2) pPOL, 3) pPOL-ENV-U3, 4) pPOL-ENV/TR, 5) pCI-neo, 6) pCI-ENV/TR). One of at least three independent $^3$H-Thymidine incorporation experiments with allogeneic T cells stimulated by the individual transfectants is shown. The ratio between T cells and transfectants is indicated below the bars (T: APC).

FIG. 7A. IDDMK$_{1,2}$22-5' LTR.

This figure shows the sequence of the 5' LTR (U3 RU5) or the IDDMK$_{1,2}$22-provirus (SEQ ID NO:32).

FIG. 7B. IDDMK$_{1,2}$22-3' LTR.

This figure shows the sequence of the 3' LTR (U3 RU5) of the IDDMK$_{1,2}$22 provirus (SEQ ID NO:33).

FIG. 7C. IDDMK$_{1,2}$22-env.

This figure shows the full nucleotide sequence (SEQ ID NO:34) of the env coding region, starting with the ATG initiation codon at position. 59 (as shown in FIG. 7D).

The first internal stop codon TAG at position 518 is underlined corresponding to the codon where, following a −1 frame shift, translation stops to give rise to the protein illustrated in FIG. 7D.

The second internal stop codon TAG at position 601 (in frame with the earlier TAG) is also underlined. Translational stop at this codon gives rise to the IDDMK$_{1,2}$22-ENV/S (SAG) protein illustrated in FIG. 7G. The nucleic acid coding for the IDDMK$_{1,2}$22-env/'s (SAG) protein is also shown in FIG. 7E.

FIG. 7D. The nucleotide (SEQ ID NO:35) and deduced amino acid (SEQ ID NO:36) sequence of IDDMK$_{1,2}$22-SAG.

Figure 3A:
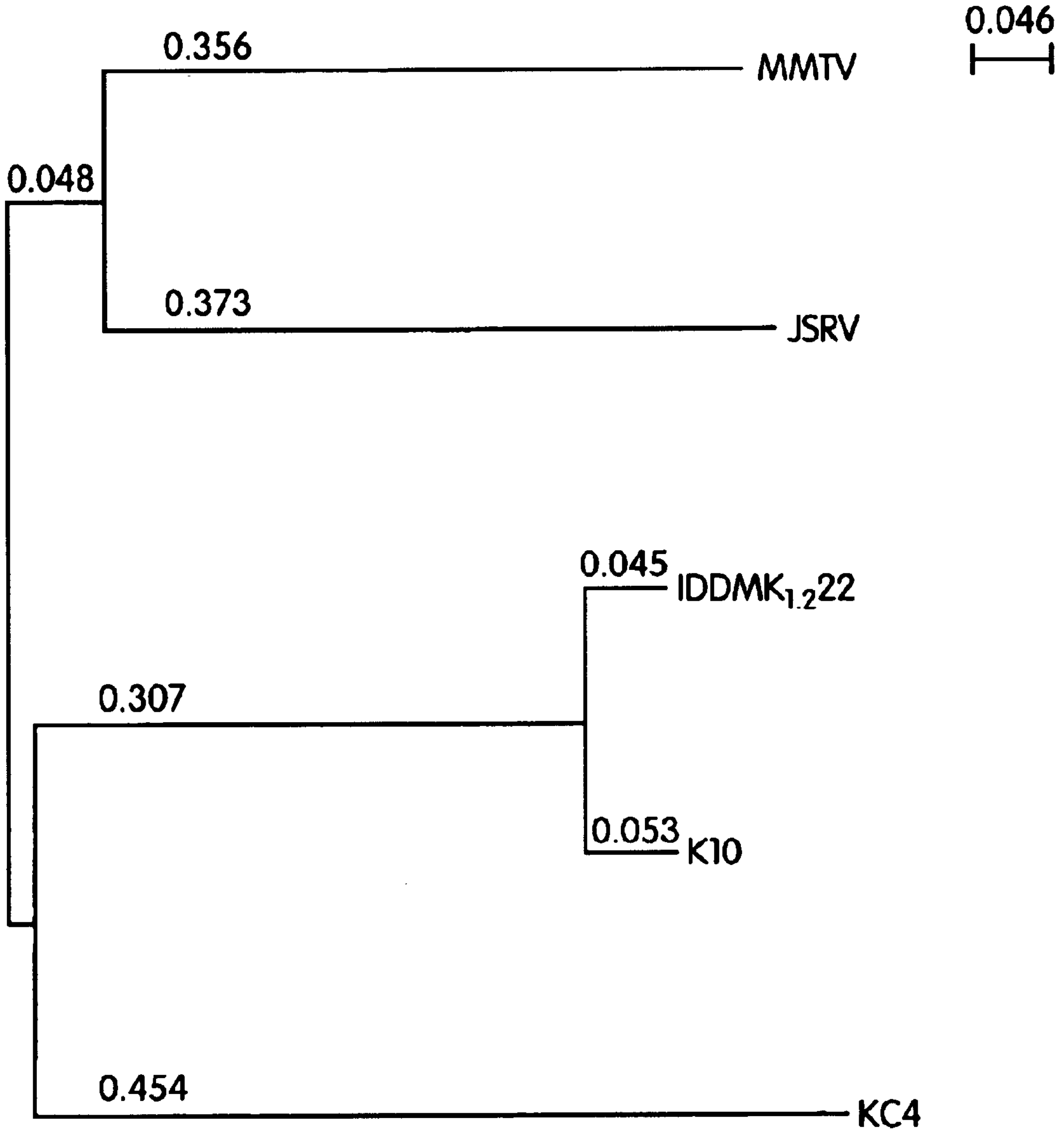

The minimal stimulatory sequence corresponding to the insert of pCI-ENV/TR comprises a C-terminally truncated protein of 153 amino acids. There is only one ORF with a stop codon at position 518. The first potential start codon in a favorable context is at position 59. Two potential N-linked glycosilation sites are present at positions 106, and 182 respectively. The degree of homology with other retroviral ENV proteins is shown in FIG. 3A. No significant homology was detected with the SAG of MMTV or with autoantigens known to be important in IDDM.

FIG. 7E. IDDMK$_{1,2}$22-env/fs-sag.

Wild-type Nucleotide sequences (SEQ ID NO:37) coding for the 181 amino acid IDDMK$_{1,2}$22-ENV/FS-SAG protein shown in FIG. 7G. To give rise to the SAg protein shown in FIG. 7G, translation of this nucleotide sequence involves a read-through of the first stop codon at position 518 followed immediately by a −1 frame shift.

FIG. 7F. IDDMK$_{1,2}$22-ENV.

Deduced amino acid sequence (SEQ ID NO:38) encoded by the full env coding region (as shown in FIG. 7B), without frame shift.

The underlined <Z> is the stop site for the 153 amino acid protein shown in FIG. 7D.

FIG. 7G. Recombinant IDDMK$_{1,2}$22 ENV/FS (SAG).

With respect to wild-type IDDMK$_{1,2}$22 (SEQ ID NO:3) env an insertion of a T at position 517 (underlined) results in a predicted protein (SEQ ID NO:40) corresponding to the one expected to be generated by IDDMK$_{1,2}$22 ENV/FS. The additional predicted C terminal amino acids that characterize ENV-FS are underlined. This protein has marked SAg activity.

FIG. 7H. IDDMK$_{1,2}$22 POL.

Deduced amino acid sequence (SEQ ID NO:41) of the POL protein of IDDMK$_{1,2}$22.

FIGS. 8A to 8G illustrate candidate 5' STRs (SEQ ID NO:42–48 respectively) isolated in the first step of the six-step procedure (illustrated in FIG. 2A) to isolate putative retroviral genomes from IDDM patients.

FIG. 9. Functional assay for the presence of Vβ-IDDM-SAG in PBL.

PBL (peripheral blood lymphocytes) are isolated from 10 ml of Heparine-blood (Vacutainer) from IDDM patients or controls with Ficoll-Hypaque (Pharmacia). 5×10$^6$ PBL are incubated with or without 10$^3$ U/ml recombinant human INF-γ (Gibco-BRL) for 48 hours.

100 μg/ml Mitomycin C (Calbiochem) are added to inactivate for 10$^7$ cells for 1 hour at 37° C., and extensive washing is performed.

Culture with T cell hybridomas bearing human vβ-2, -3, -7, -8, -9, -13 and -17 at stimulator: responder ratios of 1:1 and 1:3 in 96 round bottom wells. TCR-crosslinking with anti-CO3 antibodies (OKT3) is used as a positive control for each individual T hybridoma.

IL-2 release into the supernatant is measured with the indicator cell line CTLL2 according to standard procedures.

Results are expressed as percentage of maximal stimulation obtained with TCR crosslinking in the same experiments.

A selectively induced TCR-crosslinking and IL-release of Vβ7 is interpreted as being compatible with the presence of IDDM-SAG in PBL from the individual analysed.

EXAMPLES

In two patients with type I diabetes, a dominant pancreatic enrichment of one Vb-family, Vb 7, has been observed (Conrad et al., 1994). The same dominant enrichment of Vb 7 could be mimicked by stimulating T cells of diverse haplotypes with surface membrane preparations derived from the pancreatic inflammatory lesions but not with membranes from MHC-matched healthy control islets. This was taken as evidence for the presence of a surface membrane-associated SAG (Conrad et al., 1994).

In the framework of the present invention, the hypothesis that this SAG is of endogenous retroviral origin has been tested. Below it is shown that the SAG identified in these two patients is encoded by a human endogenous retrovirus related to MMTV. Expression of this endogenous SAG in IDDM suggests a general model according to which self SAG-driven and systemic activation of autoreactive T cells leads to organ-specific autoimmune disease.

Example 1

Cultured Leukocytes from Inflammatory B-cell Lesions of IDDM-patients Release Reverse Transcriptase Activity Expression of cellular retroelements may be associated with measurable Reverse Transcriptase-activity (RT)

Figure 1B:
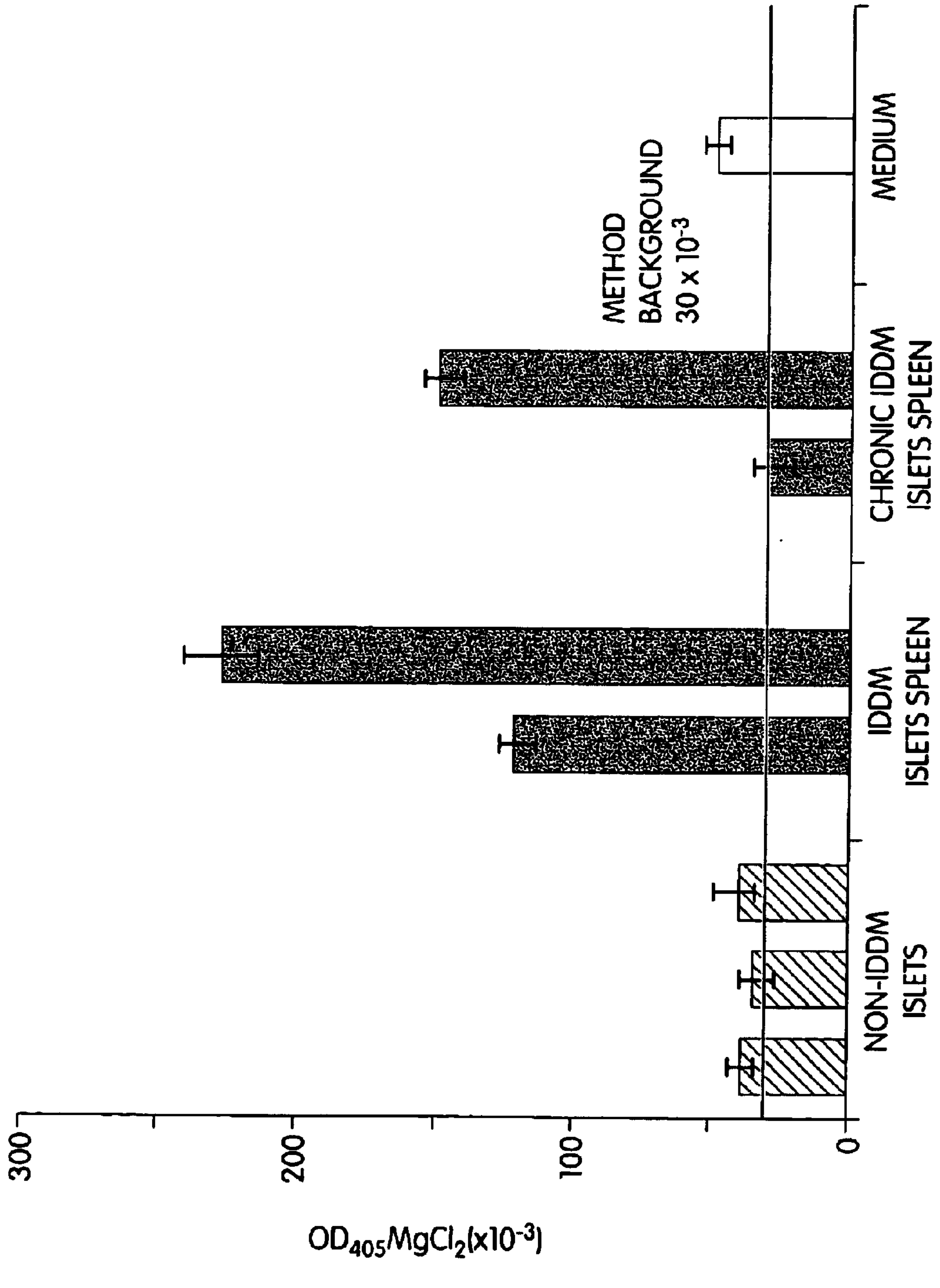

(Heidmann et al., 1991). An RT-assay detected up to a hundredfold increase in RT-activity in supernatants from short-term cultures of freshly isolated pancreatic islets derived from two patients (FIG. 1A), (Conrad et al., 1994; Pyra et al., 1994). No RT-activity above background levels was detected in medium controls, indicating that the RT-activity could not be accounted for by a contamination of the synthetic media and sera with animal retroviruses. We can also exclude the possibility that the RT-activity represents cellular polymerases released into the supernatant by dying cells. Indeed, no RT-activity can be detected in cultures from non-diabetic controls under conditions in which cell death is strongly enhanced, namely mitogen treated peripheral blood lymphocytes (PBL), splenocytes and cocultures of islets with allogeneic T cells. Moreover, the IDDM-derived islets were cultured for 5 days, whereas control cultures were sequentially analysed for up to 4 weeks. Finally the absence of RT-activity in the supernatants of the mitogen-treated control PBL also excluded the possibility that the RT-activity detected with the IDDM islets was simply due to non-specific cell activation. Both, the islets and the inflammatory infiltration represented potential sources for the enzymatic activity. As shown in FIG. 1B, supernatants from cultured spleen cells from the patients contained more RT-activity than, the inflammatory b-cell lesions. Moreover, the RT-activity disappeared together with the local inflammatory lesion in two patients with chronic and long-standing disease, but it persisted in cultured spleen cells from the same patient FIG. 1B). This was interpreted as being compatible with the leukocytes as the most likely source of this RT-activity.

Example 2

Isolation of a Full Length Retroviral Genome, $IDDM_{1,2}22$, from Surpernatants of IDDM Islets A strategy to isolate putative retroviral genomes from polyadenylated RNA extracted from the supernatants of IDDM islets was developed (FIG. 2A). This strategy relies on the following three characteristic features of functional retroviruses. First, retroviral genomes contain a primer binding site (PBS) near their 5' end. Cellular tRNAs anneal to the PBS and serve as primers for Reverse Transcriptase (reviewed by Whitcomb and Hughes, 1992). Second, the R (repeat) sequence is repeated at the 5' and 3' ends of the viral RNA (Temin, 1981). Third, the RT-RNAse H region of the pol gene is the most conserved sequence among different retroelements (McClure et al., 1988; Xiong and Eickbusch, 1990). These three features were exploited in a six step procedure as follows.

1) To isolate the 5' ends (5'R-U5) of putative retroviral RNA genomes, a 5' RACE procedure was performed with primers complementary to known PBS sequences (cPBS primers) (Weissmahr et al., 1997). Most retroviruses known have a primer binding site (PBS) complementary to one of only four individual 3' ends of tRNAs: $tRNA^{Pro}$, $tRNA^{Lys3}$, $tRNA^{Lys1.2}$ and $tRNA^{Trp}$. Accordingly, sequence-specific primers complementary to the four PBSs were used to derive cDNA (Weissmahr, 1995). The amplification products resulting from anchored PCR and of 100–700 bp in size were sequenced and analyzed for the presence of consensus sequences typically found in retroviral 5' R-U5s (Weissmahr, 1995).

Eight different candidate 5'R-U5 sequences ($5'K_{1,2}$-1, -4, -10, -16, -17, -22, -26 and -27) were obtained with the cPBS-$Lysine_{1,2}$ primer. All eight sequences contained features typical of the 5' ends of retroviral genomes (Temin, 1981). These include the presence at the expected positions of i) a PBS region, ii) conserved and correctly spaced upstream regulatory sequences, such as a poly(A) addition signal and site, and the downstream GT- or T-rich elements (Wahle and Keller, 1996), iii) a putative 5' end specific. U5 region and iv) a putative R region. Of the eight 5' R-U5 sequences isolated, three ($5'K_{1,2}$-1, -4, and -22) were identified on the basis of sequence homology as belonging to previously identified families of human endogenous retroviruses (HERVs) that are closely related to mouse mammary tumour viruses (MMTV), namely HERV-K(C4) (Tassabehji et al., 1994), HERV-K10 and HERV-K18 (Ono, 1986a; Ono et al., 1986b). The remaining five sequences exhibited only a distant relationship with HERV-K retroviruses.

2) A repeat (R) region conserved in the 5' R-U5 and the 3' U3-R-poly(A) is essential for retroviral first strand DNA synthesis to proceed to completion (Whitcomb and Hughes, 1992). Primers specific for the R region-sequence obtained for individual 5' R-U5s were used to prime the cDNA synthesized with oligo(dT), (Weissmahr, 1995). Products resulting from anchored PCR were sequenced and analyzed for the presence of a conserved R region followed by a poly(A)-tail. The eight 3'R-poly(A) ends ($3'K_{1,2}$-1, -4, -10, -16, -17, -22, -26 and -27) corresponding to the eight different 5'R-U5 regions identified in step 1 were isolated by means of a 3' RACE procedure using primers specific for the R regions. In each case, the isolated sequences contained the expected R region followed by a poly(A) tail.

3) The conserved RT-RNase H region within the pol gene was next amplified by PCR using degenerate primers (Medstrand and Blomberg, 1993). 15 individual subclones were sequenced and all exhibited approximately 95% similarity at the protein level to the RT-RNase H region of the HERV-K family.

4) The 5' moiety (from the U5 region at the 5' end to the pol gene) of the putative retroviral genome was amplified by PCR using primers specific for the eight different U5 regions present in the 5'R-U5 sequences (isolate in step 1) in conjunction with a primer specific for the 3' end of the central pol region (isolated in step 3). The expected size of the PCR product corresponding to the 5' moiety of full length HERV-K retroviruses is 3.6 kb (Ono et al., 1986b). Only the PCR reaction using the primer specific for the $K_{1,2}22$ 5' end clone consistently yielded a fragment of this size. Sequence analysis of several independent clones confirmed that this 3.6 kb fragment contains the R-U5-PBS region followed by coding regions corresponding to the gag and pol genes, and thus indeed represents the 5' moiety of an intact retroviral genome.

5) The 3' moiety (from the pol gene to the 3' end) of the putative retroviral genome was amplified by PCR using a primer specific for the 5' end of the central pol region (isolated in step 3) and primers specific for the poly(A) signals present in the 3'R-poly(A) sequences (isolated in step 2). The expected size of the PCR product corresponding to the 3' moiety of full length HERV-K-retroviruses is S kb (Ono et al., 1986b). The PCR reaction using a primer specific for the 3' end clone $K_{1,2}22$, which is the one that should correspond to the 3' end of the retrovirus from which the 3.6 kb 5' moiety was amplified in step 4, consistently yielded a fragment potentially representing an intact 3' moiety of 5 kb. Sequence analysis of several independent clones confirmed that this 5 kb fragment indeed contains coding regions corresponding to the pol and env genes followed by the expected U3-R-poly(A) region.

6) Finally, the presence of an intact 8.6 kb retroviral genome containing the overlapping 5' and 3' moieties isolated in steps 4 and 5 was confirmed by PCR using primers specific for its predicted U5 and U3 regions.

The full length retroviral genome that was isolated was called IDDMK$_{1,2}$22, where IDDM refers to the tissue source, K$_{1,2}$ refers to Lysine$_{1,2}$ cPBS primer and 22 represents the serial number of the clone. IDDMK$_{1,2}$22 was determined to be novel retrovirus on the basis of two criteria first, it has a unique pattern of restriction enzyme cleavage sites that is distinct from that of other known viruses. Second, its nucleotide and amino acid sequences in non-coding and coding regions diverge from other known retroviruses by at least 5–10%

IDDMK$_{1,2}$22 was the only full length virus identified in these experiments, suggesting that it is the only functional retrovirus specifically associated with the supernatants of the cultured IDDM islets. PCR reactions using primers specific for the other 5DR-U5-PBS and 3'U3-R-poly(A) clones isolated in steps 1 and 2 did not yield fragments of the size expected for intact retroviral genomes in steps 4 and 5. In particular, primers specific for the 5' and 3' ends corresponding to the ubiquitous HERV-K10 virus did not amplify fragments corresponding to complete genomes, although this virus is known to be released as full length genome associated with viral particles from several cell lines and tissues (Tönjes et al., 1996). Our inability to detect full length HERV-K10 genomes in the IDDM islet supernatant is unlikely to be due to a technical problem because it could be amplified very efficiently from both genomic DNA and a size selected cDNA library prepared from a B-lymphoblastoid cell line (data not shown). It is more likely that HERV-K10 is not released in significant amounts by the cultured IDDM islets.

Finally, i) we confirmed by RNA-specific PCR that sequences identical, or highly similar, to the 3' U3-R-poly (A) of IDDMK$_{1,2}$ were present in RT-positive but not in RT-negative samples analysed; ii) in a preliminary epidemiological study we detected by PCR sequences identical, or highly similar, to the 3' U3-R-poly(A) of IDDMK$_{1,2}$ only in the plasma of 10 recent onset IDDM patients but not in the plasma of 10 age-matched non diabetic controls (FIG. 2F); and iii) we confirmed by PCR the presence of sequences identical, or highly similar to the U3-R region of IDDMK$_{1,2}$ in genomic DNA of IDDM patients (n=10) and non diabetic controls (n=10) (FIG. 2F). In summary, these data indicate that IDDMK$_{1,2}$ is an endogenous retrovirus that is released from leukocytes in IDDM patients but not in non diabetic controls.

Example 3

IDDMK$_{1,2}$22 is a Novel Member of the MMTV-related Family of HERV-K, and is Related to HERV-X10

Figure 3B:
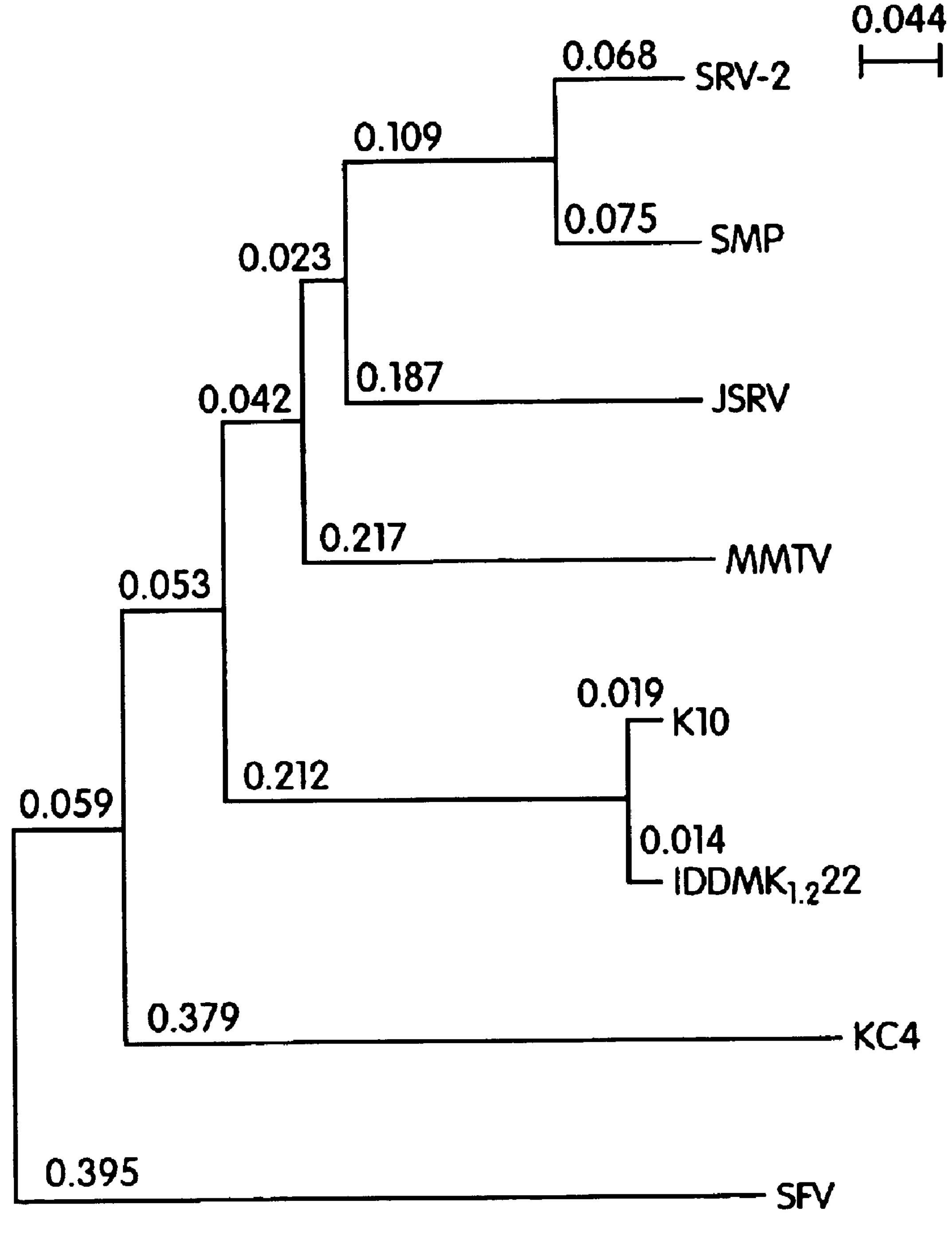
Figure 3C:
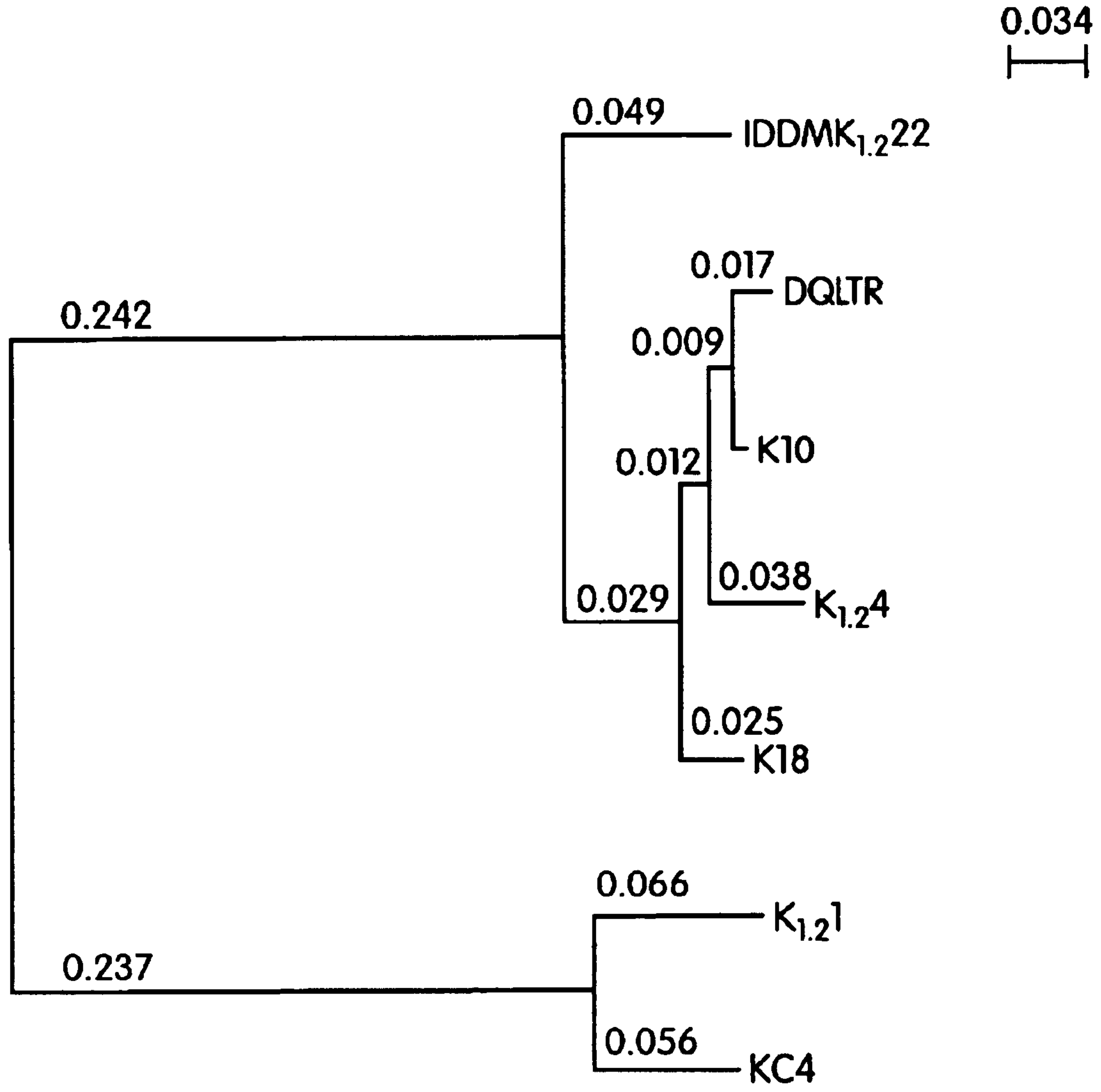

To evaluate the relationship between IDDMK$_{1,2}$22 and other known retroviruses we derived phylogenetic trees for subregions exhibiting different degrees of conservation (Galtier et al., 1996; Saitou and Nei, 1987; Thompson et al., 1994). The three regions chosen for this analysis were the RT region of the pol gene (FIG. 3B), the outer region (SU, surface) of the env gene (FIG. 3A) and the U3 region of the LTR (FIG. 3C). The RT and SU regions were selected to construct interspecies phylogenetic trees because they represent, respectively, the most highly conserved and the most variable of the protein coding regions (McClure et al., 1988). The U3 region of the LTR was chosen to construct an intraspecies tree of the family to which IDDMK$_{1,2}$22 belongs because LTR sequences are conserved in size and sequence only within a given species, and the U3 region-accounts for most of the intraspecies differences (Temin, 1981). As shown in FIG. 3A, the ENV polyprotein of IDDMK$_{1,2}$22 is most closely related to that of HERV-K10. Both proteins are related to those of MMTV and Jaagsiekte sheep retrovirus (JSRV). The same is essentially true for the RT-subregion of the POL polyprotein, where IDDMK$_{1,2}$22 and HERVK10 are most closely related to the B-type retrovirus MMTV (FIG. 3B). FIG. 3C illustrates, that K$_{1,2}$1 is related to HERV-K(C4), while K$_{1,2}$4 and IDDMK$_{1,2}$22 are related to the K10/K18 subfamily. Within this family, K$_{1,2}$4 is closely related to K10, whereas IDDMK$_{1,2}$22 appears to be more distant.

Example 4

IDDMK$_{1,2}$22 Encodes a Vβ7-specific SAG

Figure 4A:
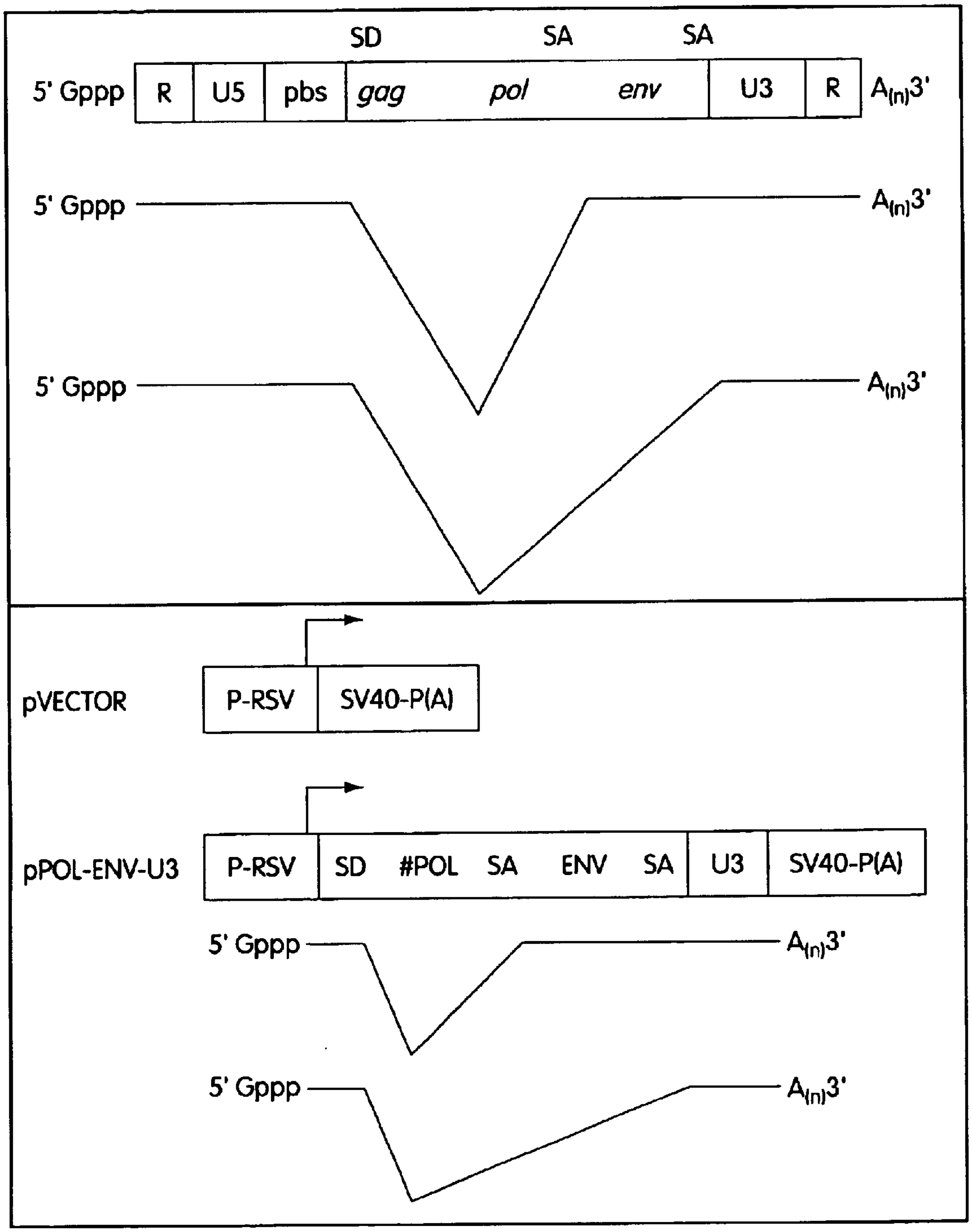

The strategy used to identify a putative SAG-function encoded by IDDMK$_{1,2}$22 was dictated by 1) predictions based on the biology of the MMTV-SAG, 2) general requirements for a protein-protein interaction between a SAG and MHC class II molecules and 3) intracellular trafficking mechanisms used by proteins encoded by retroviruses. The prototypical retroviral SAG of MMTV is a type II transmembrane protein that is encoded within the U3 of the 3' LTR (reviewed by Acha-Orbea and McDonald, 1995). It is targeted into the MHC class II peptide loading compartment and exported to the cell surface. On the basis of potential splice donor (SD) and acceptor sites (SA) present in its sequence, IDDMK$_{1,2}$22 is expected to generate two subgenomic mRNAs, one encoding ENV and a second transcript comprising the U3-R region (FIG. 4A). Based on these criteria we produced an episomal expression construct (pPOL-ENV-U3) with a 5' SD positioned upstream of the truncated pol, env and U3-regions (FIG. 4A). It is expected that both of the putative subgenomic mRNAs can be generated from this construct (FIG. 4A).

Figure 4B:
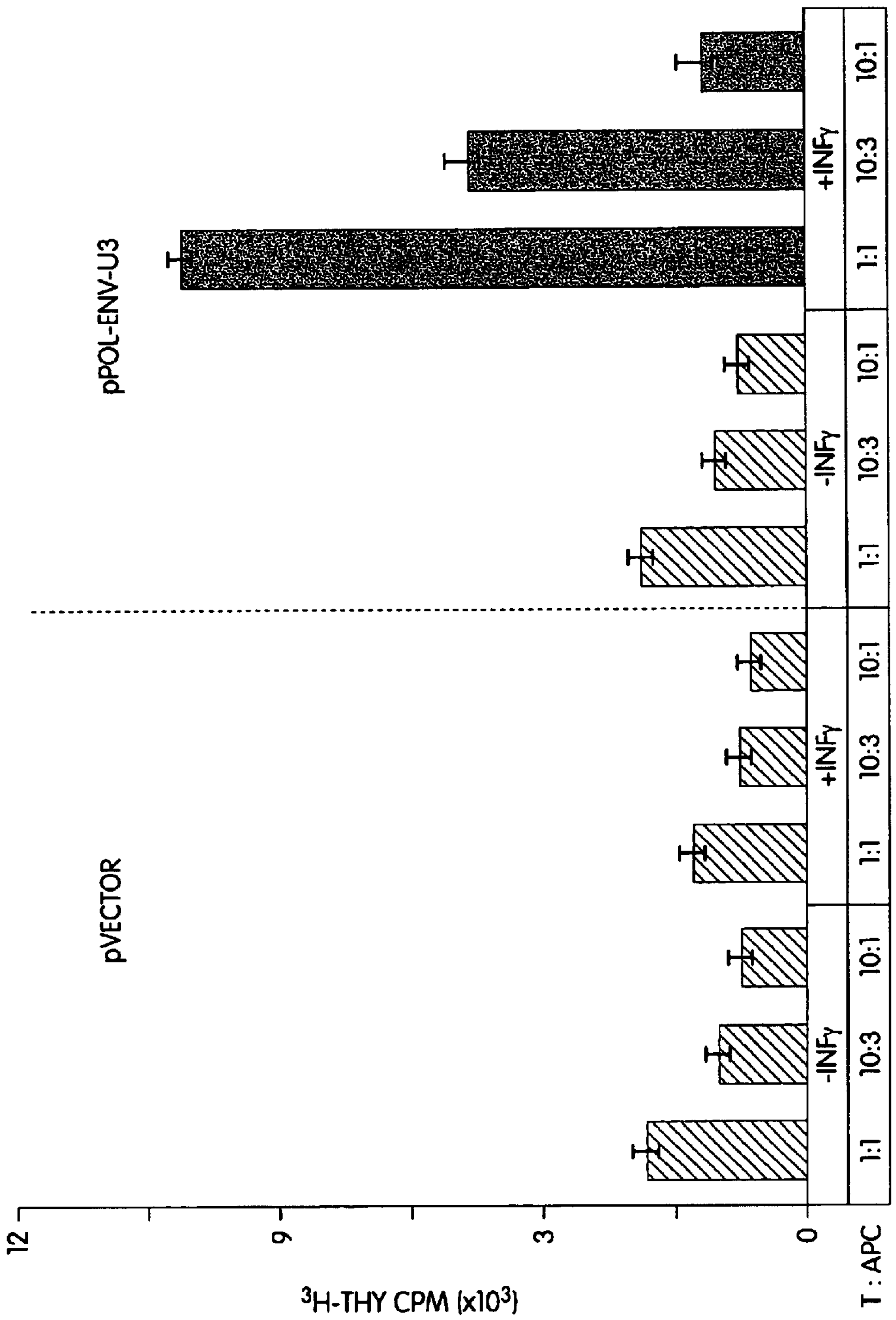
Figure 4C:
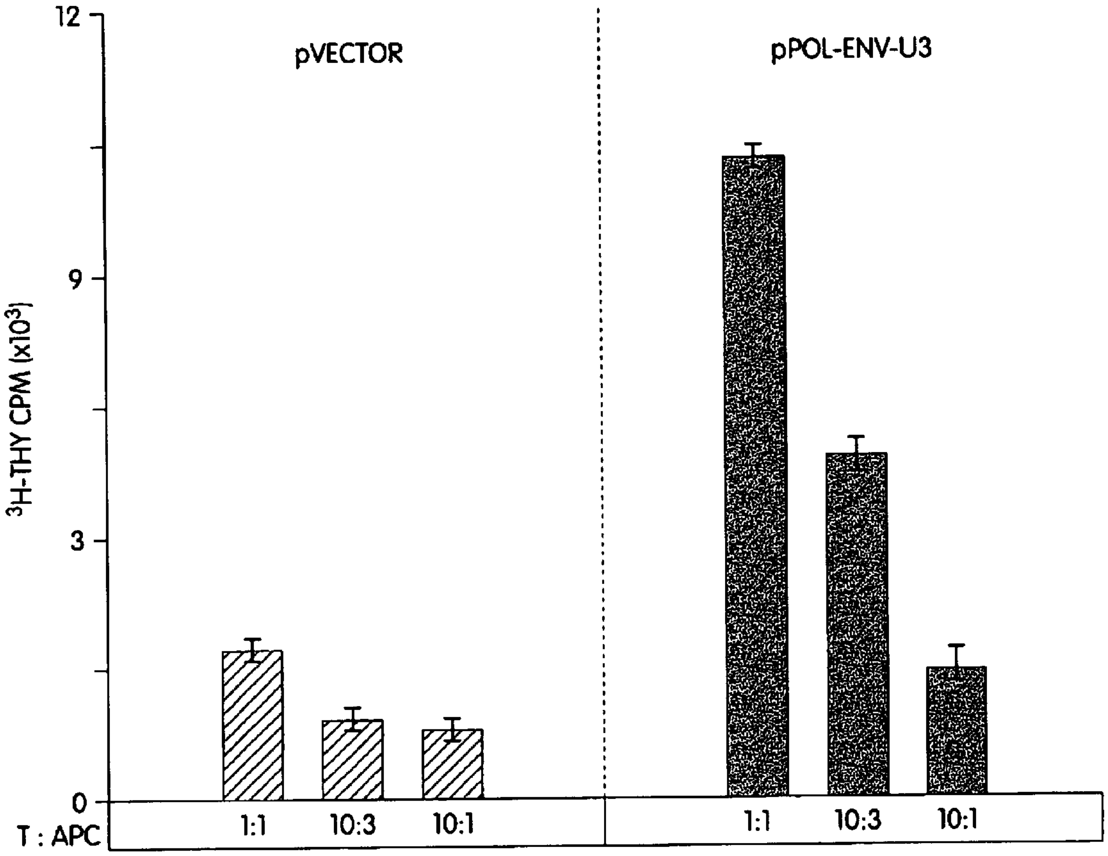
Figure 4D:
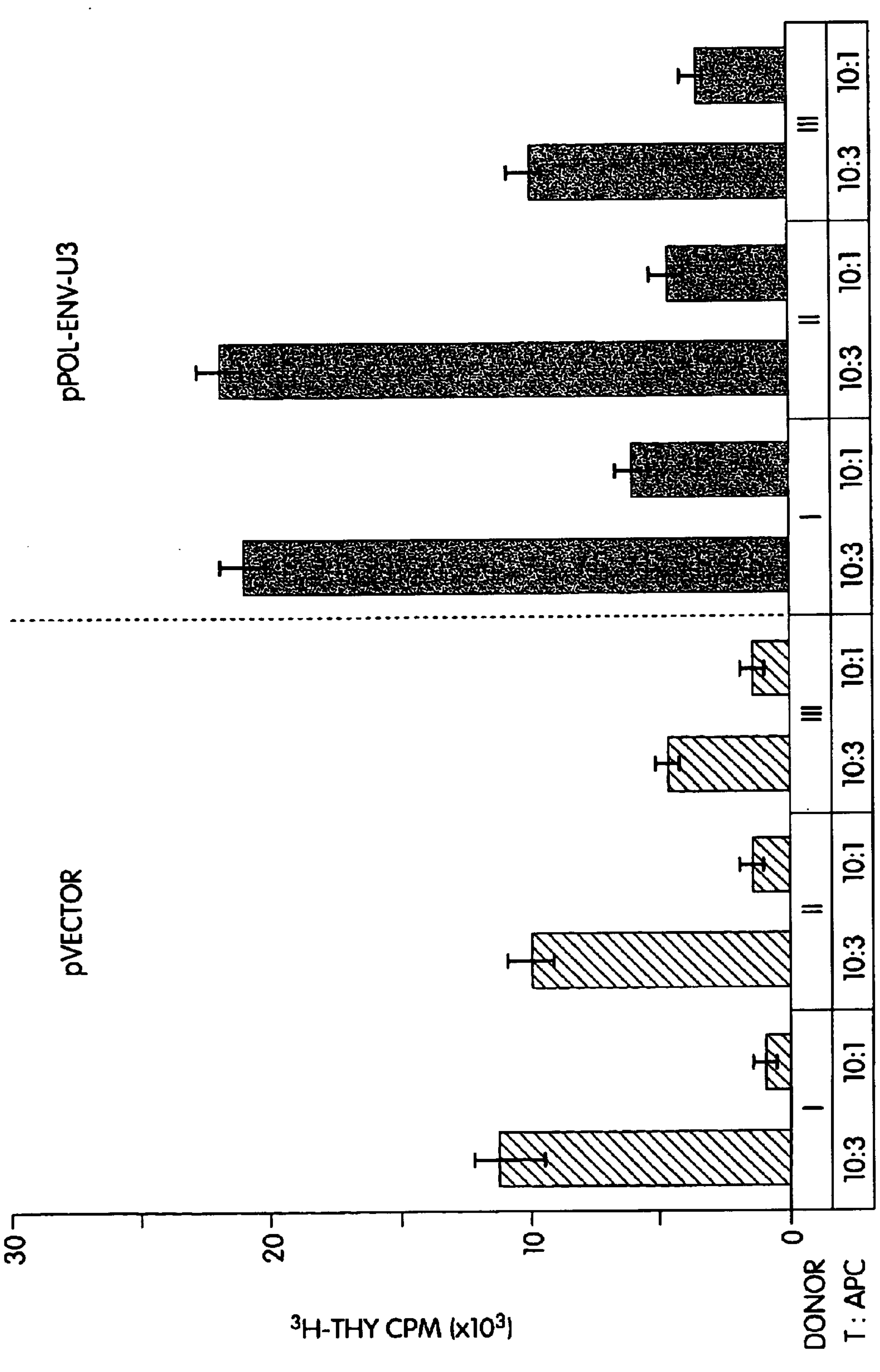

Retroviral—and control-transfectants of monocyte—and B lymphocyte-cell lines were generated and tested for their ability to stimulate MHC compatible and allogeneic T cell lines in a Vβ-specific manner. Monocytes do not express measurable MHC class II surface proteins in the absence of induction by Interferon-γ (INF-γ); the MHC class II trans-activator CIITA mediates INF-γ-inducible MHC class II expression (reviewed by Mach et al., 1996). As shown in FIG. 4A, transient monocyte (THP1, U937) transfectants induced with INF-g and expressing the truncated IDDMK$_{1,2}$22 genome (pPOL-ENV-U3) stimulated in a dose-dependent fashion T cell lines from MHC-compatible donors essentially to the same extent. The mitogenic effect was dependent on the presence of MHC class II, since INF-g-mediated MHC class II expression specifically induced the stimulatory capacity of retroviral- as compared to control-transfectants (FIG. 4B). The use of THP1 cells rendered constitutively MHC class II positive by transfection with CIITA resulted in a stimulation comparable to INF-g-induction, suggesting that the INF-g-induced and CIITA-dependent MHC class II expression was indeed responsible for this functional difference (FIG. 4C). The mitogenic effect is not MHC-restricted, since a response exceeding allostimulation was observed when PBL from several different MHC-disparate donors were tested for proliferative responses to monocytes transfected with pPOL-ENV-U3 (FIG. 4D). In essence, these functional data suggest that the truncated IDDMK$_{1,2}$22 (pPOL-ENV-U3) genome is responsible for a mitogenic effect that is MHC class II-dependent but not MHC-restricted.

Experiments were performed in bulk-cultures using TCR-Vβ-specific stimulation and expansion as a readout. Retroviral THP1 transfectants induce a more than 15 fold increase in the number of the Vβ-7 family but not of the two control families tested (Vβ8, Vb12) after specific stimulation and subsequent amplification (FIG. 5, Table 1). This was verified by using two different Vβ-7-specific monoclonal antibodies, 3G5 and 20E. A comparable effect was also observed when PBL from MHC-disparate donors were tested. This was interpreted as evidence for the presence a Vβ-7-specific SAG.

The monocytic cell lines were at least 3 times more efficient in terms of specific TCR Vb-7 amplification as compared to the most efficient B lymphoblastoid cell line (Table 1). This difference could not be explained by variations in the level of MHC class II expression or by the individual MHC haplotypes present. On the other hand, it may be due to differential expression of costimulatory molecules or secretion of cytokines. In conclusion, by all criteria known to date, $IDDMK_{1,2}22$ encodes a mitogenic activity having all features of a Vb-7-specific SAG.

TABLE 1

$IDDMK_{1,2}22$ mediates a Vβ7-specific SAG-effect

| | Vβ-FAMILY | | |
|---|---|---|---|
| TRANSFECTANT | Vβ-7 | Vβ-8 | Vβ-12 |
| Raji-pPOL-ENV-U3 | 7% | 5% | 2.5% |
| Raji-pVECTOR | 1.5% | 5.5% | 2% |
| THP1-pPOL-ENV-U3 | 16% | 5.3% | 2.8% |
| THP1-pVECTOR | 1% | 5.8% | 3% |

Example 5

The SAG Function is Mediated by the N-terminal Moiety of the env Protein

Figure 6A:
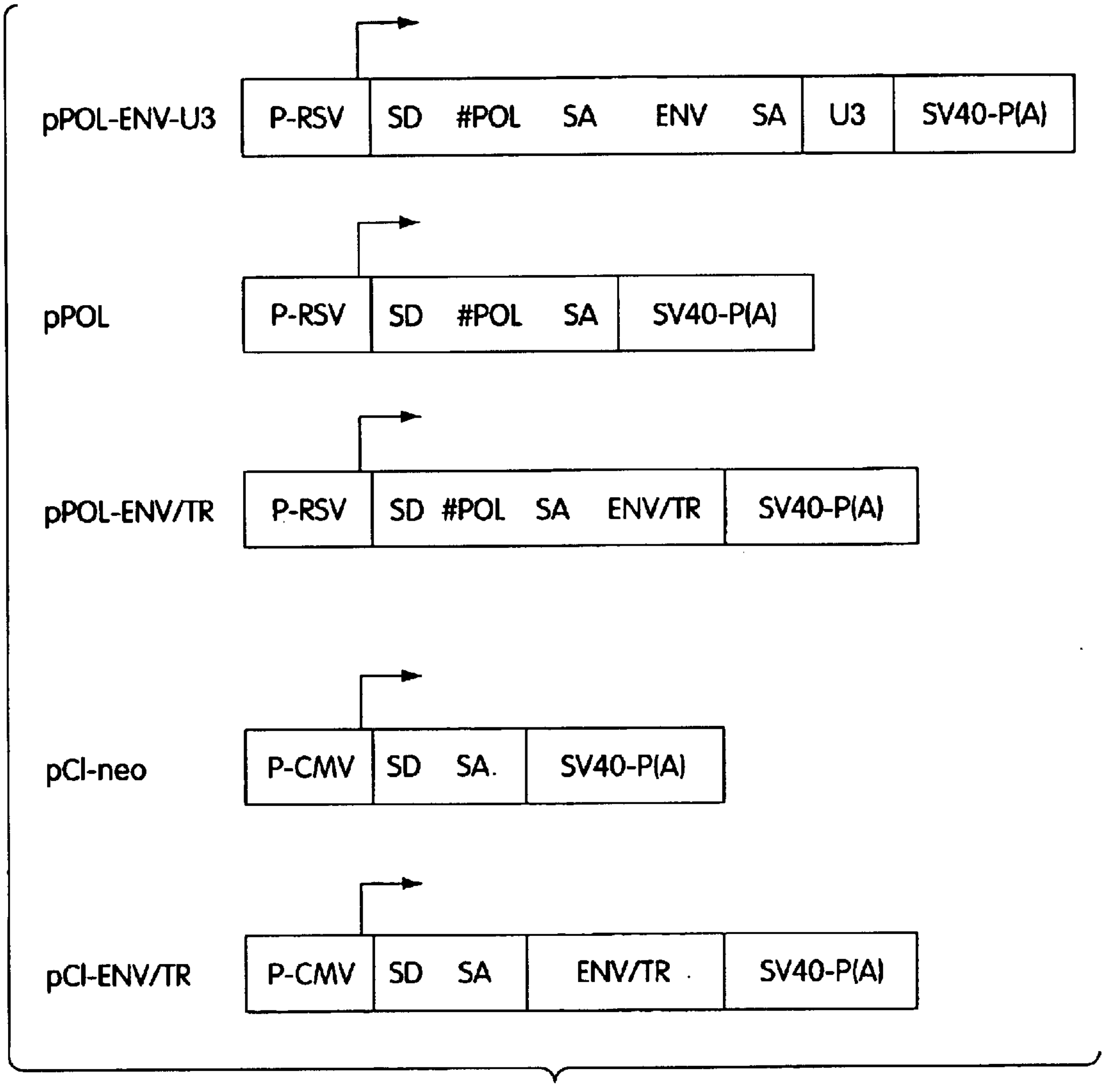
Figure 6B:
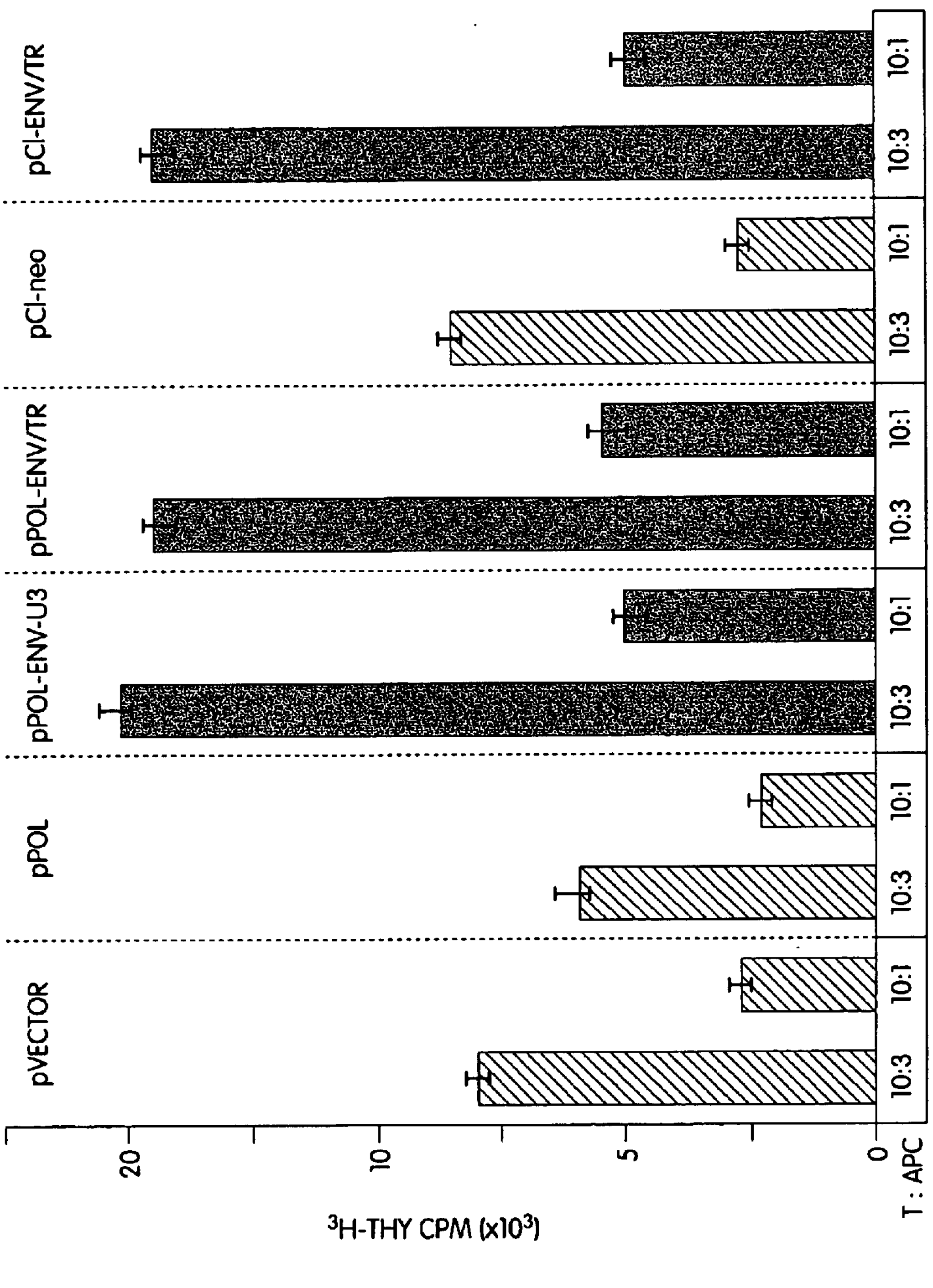

A series of deletional mutants were generated that contained either the truncated pol-env-U3 region (pPOL-ENV-U3), the truncated pol gene alone (pPOL), or the truncated pol gene followed by the env gene truncated downstream of the -premature stop codon found in all clones (pPOL-ENV/TR), (FIG. 6A). In addition, a C-terminally truncated env gene was generated as an individual expression unit (pCI-ENV/TR). As shown in FIG. 6B, by excluding the env-coding region the SAG-function is selectively lost (pPOL). If, however, the truncated env gene is included (pPOL-ENV/TR), the stimulatory capacity is restored to levels comparable to pPOL-ENV-U3. In addition, expression of the truncated env gene alone (pCI-ENV/TR) is sufficient for function. These findings demonstrate that the SAG function is mediated by the N-terminal moiety of the env gene comprising 153 amino acids. The nucleotide and predicted amino acid sequences of the minimal stimulatory region are shown in FIG. 7. As shown in FIG. 3A, this predicted protein resembles the N-terminal ENV proteins of related HERVs (HERV-K10), and those of the B-type retroviruses (MMTV, JSRV). However, there is no significant sequence homology with either MMTV-SAG, other SAGs, or autoantigens known to be important in IDDM.

Here, evidence is provided showing that a human endogenous retrovirus, $IDDMK_{1,2}22$, is released from leukocytes in patients with acute onset type I diabetes. In preliminary experiments $IDDMK_{1,2}22$ RNA sequences were detectable in the plasma of IDDM patients at disease onset but not in the plasma of age-matched healthy controls. This novel human retrovirus is related to MMTV and encodes a SAG with functional characteristics similar to the one encoded by MMTV. In contrast to MMTV, however the IDDM-associated SAG is encoded within the retroviral env gene rather than within the 3' LTR. It has the same TCR Vβ-specificity with the SAG originally identified in the IDDM patients. This SAG is thus likely to be the cause of the Vb7-enriched repertoire of islet-infiltrating T lymphocytes.

$IDDMK_{1,2}22$ as a Member of the HERV-K Class of Endogenous Retroviruses

HERV-K genomes exist in two different forms, type I genomes which are largely splice deficient and type II genomes which generate three subgenomic mRNAs (Tönjes et al., 1996; Ono, 1986). A 292 bp insert at the pol-env boundary with clustered nucleotide changes downstream of the splice acceptor site are present in type II but not in type I genomes (Tönjes et al., 1996). The insert affects both, the env and pol gene: i) type II genomes have a stop codon between env and pol which is missing in type I genomes and ii) have a considerably longer N terminal env region. The 292 bp insert and the clustered nucleotide changes have been proposed to be responsible for the efficient splicing of type II genomes (Tönjes et al., 1996). $IDDMK_{1,2}22$ is missing the 292 bp insert but has two in frame stop codons between env and pol and the clustered nucleotide changes downstream of the SA typical of those found in type II genomes. In terms of splice efficiency, $IDDMK_{1,2}22$ may be in an intermediate position between type I and II genomes. This and the altered N terminal sequences in $IDDMK_{1,2}22$ with respect to type II genomes may affect SAG expression in vivo. However, as shown in FIG. 4, the 3' terminal moiety (POL-ENV-U3) of the $IDDMK_{1,2}22$ genome mediates the SAG function in vitro. Moreover, it is known from MMTV that the SAG function in vivo may be present at levels where the respective protein remains undetectable (Winslow et al., 1992; reviewed by Acha-Orbea and MacDonald, 1995).

The Model: Human Self SAGs as Activators of Autoreactive T Cells in Type I Diabetes A model is proposed according to which induction of self SAGs in systemic and professional APCs, outside the pancreas, leads to autoimmunity in genetically susceptible individuals. The model implies two steps, the first is systemic, the second organ-specific. The initial event is a systemic, polyclonal activation of a Vb-restricted T cell subset, triggered by the expression of an endogenous retroviral SAG in professional MHC class $II^{+}$APCs. In a second step, autoreactive T cells within the subset of SAG-activated T lymphocytes initiate organ-specific tissue destruction. The evidence presented here, however, does not rule out that the release of the $IDDMK_{1,2}22$ RNA sequences in vivo and the SAG function associated with IDDM in these patients are the consequence rather than the cause of the inflammation.

The expression of self SAGs can in principle be modulated by two variables: physiological endogenous stimuli or environmental stimuli. A possible physiological stimulus might be steroid hormones. HERV-K10 expression is steroid-inducible in vitro and this is possibly the result of hormone response elements (HRE) present in its LTR (Ono et al., 1987). $IDDMK_{1,2}22$ and HERV-K10 share the same putative HRE in their respective LTRs (Ono et al., 1987), (FIG. 3). Steroid inducibility of $IDDMK_{1,2}22$ could therefore also occur in vivo, in analogy to the well documented example of the transcriptional control by steroid hormones of the MMTV promoter (reviewed by Acha-Orbea and Mac Donald, 1995). Infectious agents are of major importance when considering environmental factors. Examples include the cellular SAGs that are expressed by herpesvirus-infected monocytes and B-lymphocytes (Dobrescu et al., 1995; Sutkowski et al., 1996). In both cases, HERVs have not been excluded as a potential source of the SAG-activity. It is thus conceivable that SAGs are being selectively expressed in response to ubiquitous pathogens such as herpesviridae (reviewed by Roizman, 1996). In fact, HERVs are induced by a variety of environmental stresses, and some of them behave as hepatic acute-phase genes (reviewed by Wilkinson et al., 1994).

The experimental evidence presented suggests that the RT-activity, the IDDMK$_{1,2}$22 RNA sequences and in consequence the SAG may derive from leukocytes rather than from the pancreatic b-cells. This may indicate that expression of the retroviral SAG is induced preferentially in systemically circulating professional MHC class II$^+$ APCs. The highest rate of IDDM coincides with puberty (10–14 years) in both sexes (Bruno et al., 1993). Infections with ubiquitous viruses (reviewed by Roizman, 1996) may act synergistically with an increase in the circulating levels of steroids to enhance expression of the SAG in professional APCs. Autoreactive T cells can be readily demonstrated in the mature repertoire of healthy individuals (Pette et al., 1990). However, in order to able to migrate to the target tissue these T cells have to be activated (reviewed by Steinman, 199.5). These considerations lead us to the hypothesis that among the Vb7$^+$-T cells activated by IDDMK$_{1,2}$22-SAG, some are autoreactive and migrate to the target tissue were b-cell specific death ensues. Once b-cells die, cellular antigens are liberated and the immune response perpetuated through determinant spreading (reviewed by McDevitt, 1996).

The Concept of IDDMK$_{1,2}$22-sag as Autoiune Gene

Known genes conferring susceptibility to autoimmune diseases are host-derived, stably inherited Mendelian traits and contribute in a cumulative fashion to the familial clustering of the disease without causing disease per se (reviewed by Todd, 1996). IDDMK$_{1,2}$22 should be viewed as mobile genetic element with the potential to move within the host genome due to multiple mechahisms, including retrotransposition, homologous recombination, gene conversion and capture, resulting in multiple copies of individual HERVs (reviewed by Preston and Dougherty, 1996; Wain-Hobson, 1996). This renders family studies dealing with searches for HERV-disease association difficult. It should be noted, however, that there is little or no plus/minus genetic polymorphism in different humans at the HERV-K loci and as yet no evidence for mobility. Interestingly, an IDDMK$_{1,2}$22-related HLA-DQ-LTR is associated with susceptibility to IDDM, possibly due to cosegregation with the HLA (FIG. 3C), (Badenhoop et al., 1996). In addition, infectious transmission cannot be excluded, as is the case for two closely related virus groups containing endogenous and exogenous variants: MMTV and JSRV (FIGS. 4A and 4B), (reviewed by Acha-Orbea and McDonald, 1995; York et al., 1992).

In summary, this candidate autoimmune-gene has distinctly different features from classical, disease-associated susceptibility genes. It has the potential of being transmitted as either an inherited trait or as an infectious agent. Moreover, this gene has no apparent essential function for the host but it may have instead an inducible and intriguing potential to directly cause disease whenever expressed in genetically susceptible individuals.

Example 6

Development of an Animal Model to Document and Study the Sag Effect in Vivo

Several mouse cell lines, in particular a B lymphocytes line (A20) and a monocyte line (WEHI-3) were stably transfected with the IDDM Sag cDNA (corresponding to the minimal region encoding a.a. 1 to 153 of the env protein of IDDM1,2,22, as described above). The B cell lines express mouse MHC class II molecules constitutively. In the case of monocyte lines, the transfectants are induced to express mouse MHC class I: molecules by treatment with mouse interferon gamma (100–1000 units of mouse interferon (Genzyme) per ml for 48 hrs).

These MHC class II positive Sag transfectants were capable of stimulating (in vitro) human T lymphocytes of the Vβ7 specificity, and not Vβ8 or Vβ12 as negative controls. This demonstrates that the IDDM Sag can function when expressed on MHC class II positive mouse cells. These Sag-expressing, MHC class II positive, mouse transfectants are used to immunise mice against the Sag protein and to generate anti Sag monoclonal antibodies, using as control the homologous untransfected cell lines.

This Sag effect lead to the stimulation of Vβ7-specific T lymphocytes of both the CD4 and the CD8 type. This observation indicates that the IDDM Sag functions in T cell activation in a manner that is independent of the co-receptors CD4 and CD8. This situation is different from what is observed in the case of the mouse MMTV Sag, where only CD4 T lymphocytes are stimulated.

The same MHC class II positive mouse stable Sag transfectants (A 20, B lymphocytes and WEHI-3, monocytes), expressing the minimal functional region of IDDM Sag defined above (and corresponding to a.a. 1 to 153 of the env protein of IDDM1,2,22) specifically stimulated mouse T lymphocytes of the Vβ4 and the Vβ10 specificity. (These are the most highly related mouse Vb sequences, from a structural point of view, to human Vβ7).

Again, both CD4 and CD8 mouse T lymphocytes were activated, indicating a Sag mediated activation that is independent of the CD4 and CDϵ co-receptors.

More importantly, injection of the same stable Sag transfectants into mice (either in the bind foot path or in the tail vein) lead to in vivo activation of T lymphocytes, again with the same Vβ specificity observed upon in vitro mouse T cell activation by the IDDM Sag. T cell activation and Vβ specificity in response to the injection of Sag transfectants was monitored by analysis of T lymphocytes in draining lymph nodes and in the spleen.

The ability to induce Vβ-specific T lymphocyte activation in vivo in mice following injection of MHC class II positive transfectants expressing IDDM Sag indicates that the biological effect of IDDM Sag can now be monitored in an in vivo animal model. This allows the testing in vivo, not only of a Sag biological effect, but also of potential inhibitors of the effect of Sag, such as anti-Sag antibodies, including monoclonal anti-Sag antibodies, and small molecular weight inhibitors of Sag (first identified as inhibitors of Sag in in vitro cell based assays). Finally, this in vivo model of the biological effect of Sag allows to test the effect of prior immunisation of animals with the Sag protein (or derivatives thereof) on the biological effect of Sag in vivo. This model provides a test of the possibility of a protective vaccination against IDDM Sag in vivo.

Transgenic mice carrying the IDDM Sag gene have been obtained. The Sag gene is under the control of a tetracycline operator element (consisting of a heptameric repeat of the Tn motive linked to a minimal promoter). These transgenic mice have been crossed with two other transgenic mice carrying the tetracycline transactivator gene (TTA) under the control of the CMV promoter. One transgenic (CMV-TTA) induces the tet transactivator upon withdrawal of tetracycline, while the other (CMV-RTTA) induces the tet transactivator in the presence of tetracycline. These double transgenic mice permit the deliberate, selective and controlled expression of Sag in vivo, allowing the subsequent study of immunopathological consequences of Sag expression.

Exactly the same steps can be followed (=Sag-expressing mouse cells and Sag expression in vivo) to establish animal models of the effect of other Sags encoded by other HERVs in the context of other autoimmune diseases, such as multiple sclerosis or rheumatoid arthritis.

Experimental Procedures

Patients

The the islets and spleens from patients with acute onset- and chronic IDDM and non diabetic organ donors were provided by the Pittsburgh Transplant Institute (Conrad et al., 1994).

The plasma and genomic DNA from patients and controls for the epidemiological study were isolated by the Diabetes Register in Turin, Italy (Bruno et al., 1993). The samples were collected within 1 month after the clinical diagnosis from patients, aged from 0–29 years (Bruno et al., 1993).

RT Assays

RT assays were performed as described (Pyra et al., 1994).

Isolation of Full Length Retroviral Genomes

A description of the criteria used to identify unknown retroviral 5' R-U5s and 3' R-poly(As) has been published (Weissmahr et al., 1997).

I. Primers sequences for the 3' moiety of the putative retroviral genomes; abbreviations are according to Eur. J. Biochem. (1985). 150, 1–5.

A. RT region

RT 1a 5' YAAATggMgWAYgYTAACAgACT3' (SEQ ID NO:8)

RT 1b 5' YAAATggMgWAYgYTAACTgACT3' (SEQ ID NO:9)

RT 2a-nested 5° CgTCTAgAgCCYTCTCCggCYATgATCCCg3' (SEQ ID NO:10)

RT 2b-nested 5° CgTCTAgAgCCYTCTCCggCYATgATCCCA3' (SEQ ID NO:11)

B. 3' U3-R-Poly(As): all primers have an identical 5'-anchor:

5' TgCgCCAgCAATgTATCCATg3'(SEQ ID NO:12)+ sequence-specific part

#1K1,2-1 5' gggTggCAgTgCATCATAggT3 ' (SEQ ID NO:13)

#4K1,2-4 5' gggAgAgggTCAgCAgCAgACA3' (SEQ ID NO:14)

#K1,2-10 5' gACAgCAAgCCAgTgATAAgCA3' (SEQ ID NO:15)

#K1,2-16 5' ggAACAgggACTCTCTgCA3' (SEQ ID NO:16)

#K1,2-17 5' gggAAgggTAAggAAgTgTg3'(SEQ ID NO:17)

#K1,2-22 5' ggTgTTTCTCCTgAgggAg3' (SEQ ID NO:18)

#K1,2-26 5' gAAgAATggCCAACAgAAgCT3' (SEQ ID NO:19)

#K1,2-27 5' gggAAACAAggAgTgTgAgT3' (SEQ ID NO:20)

Common, Secondary Anchor Primer:

3' U3-R-poly(As)common

5' CATgTATATgCggCCgCTgCgCCAgCAATgTATCCATgg3' (SEQ ID NO:21)

II. Primer Sequences for the 5' Moiety of the Genome:

A. RT-region

RT 1 5' TATCTTTCgTTTCTgCAgCAC3' (SEQ ID NO:22)

RT 2 5' TAACTggTTgAAgAgCTCgACC3' (SEQ ID NO:23)

B.5'-R-U5

R-U5-1 5' ATACTAAggggACTCAgAggC3' (SEQ ID NO:24)

R-U5-2 5' CAgAggCTggTgggATCCTCCATATgC3' (SEQ ID NO:25).

The PCR conditions were as follows: 1×94° C. 2 min; 45° C. 5 min; 68° C. 30 min; 10×94° C. 15 sec; 45° C. 30 sec+1° C./cycle; 68° C. 3 min 30 sec; 25×: 94° C. 15 sec; 55° C. 30 sec; 68° C. 3 min 30 sec+20 sec/cycle. Primers were used at 300 nM final concentration, dNTPs at 200 mM, with 52 U/ml of Taq-Pwo polymerase-mix (Boehringer Mannheim). One vol % of first-round PCR was subjected to a nested PCR. Size selected and purified amplification products were blunted, EcoRI adapted and subcloned into EcoRI-digested 1ZAPII-arms. After two rounds of hybridisation 20 individual clones were rescued as plasmids. Eleven clones were selected for further analysis based on a conserved restriction pattern. An equivalent procedure was followed for the 5' moiety of the genome. Sequencing was performed on an automatic sequencer (ABI, Perkin Elmer) using subgenomic clones.

Epidemiological study. RNA-PCR. Three ml of blood was collected in EDTA tubes (Vacutainer) and further processed within 6 hours. Samples were subjected twice to centrifugation, for $4\times10^3$ G, 10 min at 4° C. Total RNA was extracted from 560 ml of plasma (QIAamp; Qiagen). Four vol % of total RNA was used for a single tube RT-PCR using thermostable AMV, Taq and Pwo (Boehringer Mannheim). Reactions contained at a final concentration: di-Na salts of dNTPs at 0.2 mM; DTT at 5 mM; 10 U recombinant RNAsin (Promega); 1.5 mM $MgCl_2$; R-poly(A) primer 5' TTT TTg AgT CCC CTT AgT ATT TAT T 3' (SEQ ID NO:26); U3 primer 5' Agg TAT TgT CCA Agg TTT CTC C 3' (SEQ ID NO:27), both at 0.3 mM. RT was performed at 50° C. for 30 min directly followed by 94° C. 2 min; 94° C. 30 sec, 68° C. 30 sec, −1.3° C. each cycle, 68° C. 45 sec for a total of 10 cycles; 94° C. 30 sec, 55° C. 30 sec; 68° C. 45 sec for a total of 25 cycles. The amplified material (487 bp) was subjected to agarose gel electrophoresis followed by alkaline transfer and hybridisation with probes generated from the IDDMK$_{1,2}$22 U3-R-region. Genomic PCR. 100 ng of genomic DNA was subjected to PCR. Reactions contained at a final concentration: dNTPs at 200 mM; 1.5 mM $MgCl_2$; 2.6 U of Taq-Pwo (Boehringer Mannheim); U3-primer 5' Agg TAT TgT CCA Agg TTT CTC C 3' (SEQ ID NO:27); R-primers either 5' CTT TAC AAA gCA gTA TTg CTg C 3' (SEQ ID NO:28) 5' gTA AAg gAT CAA gTg CTg TgC 3' (SEQ ID NO:29), at 300 nM. The amplified products were 300 and 395 bp in size, respectively. The cycling profile war' as follows: 94° C. 2 min; 94° C. 15 sec, 68° C. 30 sec, −1.3° C. each cycle, 72° C. 45 sec for a total of 10 cycles; 94° C. 15 sec, 55° C. 30 sec, 72° C. 45 sec for a total of 25 cycles.

Sequence Alignment and Phylogenetic Trees

Sequences were aligned with CLUSTAL W (Thompson et al., 1994). Alignments were checked and manually co-rected with the SEA VIEW multiple sequence alignment editor (Galtier et al., 1996). Phylogenetic trees were commuted from multiple alignments using the "neighbour joining" method (Saitou and Nei, 1987).

Expression

Constructs. pPOL-ENV-U3: a SacI-NotI fragment derived from 11 $IDDMK_{1,2}22$ clones was ligated with 1) a BamHI-SacI adapter containing a consensus SD and 2) with a NotI-XbaI adapter and 3) was subcloned into BamHI-XbaI digested plDR2-arms, selected for by two rounds of screening and plasmids rescued. At least five independent clones were used for transfections. pPOL: pPOL-ENV-U3 was digested with KpnI-NotI, blunted and relegated. pPOL-ENV/TR: a stimulatory clone was digested with XbaI and religated. pCI-ENV/TR: 1 ng of pPOL-ENV-U3 was amplified with the primers 5' gAC TAA gCT TAA gAA CCC ATC AgA gAT gC 3' (SEQ ID NO:30) and 5' AgA CTg gAT CCg TTA AgT CgC TAT CgA CAg C 3' (SEQ ID NO:31). The amplified products were subcloned into pCI-neo (Promega).

Cells and cell lines. Monocytic cell lines: THP1, U937. B-lymphoblastoid cell lines; Raji, BOLETH, SCHU and WT 51. T cells of molecularly MHC-typed blood donors were generated by positive selection with anti-CD3 coated immunomagnetic beads (Milan-Analytika).

Transfections. Transient transfectants were used for functional assays 48 hours after transfection; stable transfectants were selected for 2 weeks in progressive concentration of Hygromycin B to a final concentration of 250 mg/ml for lymphoblastoid lines, and 50 mg/ml for monocytic cell lines.

Functional assays. Transfectants were treated with Mitomycin C (Calbiochem) at 100 mg/ml per $10^7$ cells for 1 hour at 37° C. and washed extensively. Proliferation assays. $10^5$ CD3-beads-selected, MHC compatible T cells or Ficoll-Paque-isolated allogeneic PBL were cultured with transfectants at stimulator: responder ratios of 1:1; 1:3 and 1:10 for 48 and 72 hours in 96 round-bottom,wells at 37° C. $^3$H-Thymidine was then added at 1 mCi/well and incorporation measured after 18 hours incubation at 37° C. FACS analysis and antibodies used were as described; after 3 days of specific stimulation, at T: non-T ratios of 1:1 for syngeneic, and 10:3 for allogeneic stimulations, the T cells were further expanded in 20 U/ml recombinant IL-2 for 6 days before flow cytometric analysis (Conrad et al., 1994).

References

Acha-Orbea, H., Shakow, A. N., Scarpellino, L., Kolb, E., MUller, V., Vessaz-Shaw, A., Fuchs, R., Blöchlinger, K., Rollini, P., Billotte, J., Sarafidou, M., MacDonald, H. R., and Diggelmann, H. (1991). Clonal deletion of Vb14-bearing T cells in mice transgenic for mouse mammary tumor virus. Nature 350, 207–211.

Acha-Orbea, H., and MacDonald, H. R. (1995). Superantigens of mouse mammary tumor virus. Annu. Rev. Immunol. 13, 459–486.

Badenhoop, K., Tönjes, R. R., Rau., H., Donner, H., Rieker, W., Braun, J., Herwig, J., Mytilineos, J., Kurth, R., and Usadel, K. H. (1996). Endogenous retroviral Long Terminal Repeats of the HLA-DQ region are associated with susceptibility to Insulin-dependent diabetes mellitus. Human. Immunol. 50, 103–110.

Brocke, S., Gaur, A., Piercy, C., Gautam, A., Gijbels, K., Fathman, C. G., and Steinman, L. (1993). Induction of relapsing paralysis in experimental autoimmune encephalomyelitis by bacterial superantigen. Nature 365, 642–644.

Bruno, G., Merletti, F., Vuolo, A., Pisu, E., Giorio, M., and Pagano, G. F. (1993). Sex differences in incidence of IDDM in age-group 15–29 yr. Diabetes Care 16, 133–136.

Choi, Y., Kotzin, B., Herron, L., Callahan, J., Marrack, P., and Kappler, J. (1989). Interaction of staphylococcus aureus toxin "superantigens" with human T cells. Science 86, 8941–8945.

A Choi, Y., Kappler, J. W., and Marrack, P. (1991). A superantigen encoded in the open reading frame of the 3' long terminal repeat of mouse mammary tumor virus. Nature 350, 203–207.

Cole, B. C., and Griffiths, M. M. (1993). Triggering and exacerbation of autoimmune arthritis by the mycoplasma arthritidis superantigen MAM. Arthritis Rheum. 36, 994–1002.

Conrad, B., Weidmann, E., Trucco, G., Rudert, W. A., Behboo, R., Ricordi, C., Rodriquez-Rilo, H., Finegold, D., and Trucco, M. (1994). Evidence for superantigen involvement in insulin-dependent diabetes mellitus aetiology. Nature 371, 351–355.

Dobrescu, D., Ursea, B., Pope, M., Asch, A. S., and Posnett, D. N. (1995). Enhanced HIV-1 replication in Vβ12 T cells due to human cytomegolovirus in monocytes:evidence for a putative herpesvirus superantigen. Cell 82, 753–763.

Fleischer, B., and Schrezenmeier, H. (1988). T cell stimulation by Staphylococcal Entetotoxins. J. Exp. Med. 167, 1697–1707.

Galtier, N., Gouy, M., and Gautier, C. (1996). SeaView and Phylo-win, two graphic tools for sequence alignment and molecular phylogeny. Comput. Applic. Biosci., In Press.

Heidmann, O., and Heidmann, T. (1991). Retrotransposition of a mouse IAP sequence tagged with an indicator gene. Cell 64, 159–170.

Held, W., Waanders, G. A., Shakov, A. N., Scarpellino, L., Acha-Orbea, H., and MacDonald, H. R. (1993). Superantigen-induced immune stimulation amplifies mouse mammary tumor virus infection and allows virus transmission. Cell 74, 529–540.

Howell, M. D., Diveley, J. P., Lundeen, K. A., Esty, A., Winters, S. T., Carlo, D. J., and Brostoff, S. W. (1991). Limited T-cell b-chain heterogeneity among interleukin 2 receptor-positive synovial T cells suggests a role for superantigen in rheumatoid arthritis. Proc. Natl. Acad. Sci. USA 88, 10921–10925.

Karvonen, M., Tuomilehto, J., Libman; I., LaPorte, R. (1993). A review of the recent epidemiological data on the worldwide incidence of type 1 (insulin-dependent) diabetes mellitus. Diabetologia 36, 883–892.

Lo, D., Reilly, C. R., Scott, B., Liblau, R., McDevitt, H. C., and Burkly, L. C. (1993). Antigen-presenting cells in adoptively transferred and spontaheous autoimmune diabetes. Eur. J. Immunol. 23, 1693–1698.

Mackay, C. R. (1993). Homing of naive, memory and effector lymphocytes. Curr. Op. Immunol. 5, 423–427.

Mach, B., Steimle, V., Martinez-Soria, E., and Reith, W. (1996). Regulation of MHC class II genes: lessons from disease. Annu. Rev. Immunol. 14, 301–331.

McClure, M. A., Johnson, M. S., and Doolittle, R. F. (1988). Sequence comparisons of retroviral proteins: relative rates of change and general phylogeny. Proc. Natl. Acad. Sci. USA 85, 2469–2473.

Medstrand, P., and Blomberg, J. (1993). Characterization of novel reverse transcriptase encoding human endogenous retroviral sequences similar to type A and type B retroviruses:differential transcription in normal human tissues. J. Virol. 67, 6778–6787.

Oldstone, M. B. A. (1990). Molecular mimicry and autoimmune disease. Cell 50, 819–820.

Ono, M. (1986a). Molecular cloning and Long Terminal Repeat sequences of human endogenous retrovirus genes related to types A and B retrovirus genes. J. Virol. 58, 937–944.

Ono, M., Yasunaga, T., Miyata, T., and Ushikubo, H. (1986b). Nucleotide sequence of human endogenous retrovirus genome related to mouse mammary tumor virus genome. J. Virol. 60, 589–598.

Ono, M., Kawakami, M., and Ushikubo, H. (1987). Stimulation of expression of the human endogenous retrovirus genome by female steroid hormones in human breast cancer cell line T47D. J. Virol. 61, 2059–2062.

Paliard, X., West, S. G., Lafferty, J. A., Clements, J. R., Kappler, J. W., Marrack, P., and Korzin, B. L. (1991). Evidence for the effects of a superantigen in rheumatoid arthritis. Science 253, 325–329.

Perron, H. et al (1997). P.N.A.S. 94, 7583–7588.

Pette, M., Fujiita, K., Wilkinson, D., Altmann, D. M., Trowsdale, J., Giegrich, G., Hinkkanen, A., Epplen, J. T., Kappos, L., and Weckerle, H. (1990). Myelin autoreactivity in multiple sclerosis: recognition of myelin basic protein in the context of HLA-DR2 products by T lymphocytes of multiple sclerosis patients and healthy donors. Proc. Natl. Acad. Sci. USA 87, 7968–7972.

Preston, B. D., and Dougherty, J. P. (1996). Mechanisms of retroviral mutation. Trends Microbiol. 4, 16–21.

Pyra, H., Böni, J., and Schüpbach, J. (1994). Ultrasensitive retrovirus detection by a reverse transcriptase assay based on product enhancement. Proc. Natl. Acad. Sci. USA 91,1 544–1548.

Roizman, B. (1996). Herpesviridae. In Fields Virology, B. N. Fields et al., eds. (Philadelphia: Lippincott-Raven Pubslishers), pp. 2221–2230.

Saitou, N., and Nei, M. (1987). The neighbor-joining method: a new method for reconstructing phylogenetic trees. Mol. Biol. Evol. 4, 406–425.

Stegall, M. D., Lafferty, K. J., Kam, I., and Gill, R. G. (1996). Evidence of recurrent autoimmunity in human allogeneic islet transplantation. Transplantation 61, 1272–1274.

Steinman, L. (1995). Escape from "horror autotoxicus": pathogenesis and treatment of autoimmune disease. Cell 80, 7–10.

Sutkowski, N., Palkama, T., Ciurli, C., Sekaly, R. P., Thorley-Lawson, D. A., and Huber, B. T. (1996). An Epstein-Barr virus-associated superantigen. J. Exp. Med. 184, 971–980.

Tassabehji, M., Strachan, T., Anderson, M., Campbell, R. D., Collier, S., and Lako, M. (1994). Identification of a novel family of human endogenous retroviruses and characterization of one family member, HERV-K(C4), located in the complement C4 gene cluster. Nucl. Acids. Res. 22, 5211–5217.

Temin, H. M. (1981). Structure,variation and synthesis of retrovirus Long Terminal Repeat. Cell 27, 1–3.

Thompson, J. D., Higgins, D. G., and Gibson, T. J. (1994). CLUSTAL W: improving the sensitivity of progressive multiple sequence alignment through sequence weighting, position specific gap penalties and weight matric choice. Nucl. Acids. Res. 22, 4673–4680.

Tisch R., and McDevitt, H. (1996). Insulin-dependent diabetes mellitus. Cell. 85, 291–297.

Tydén, G., Finn, P. R., Sundkvist, G., and Bolinder, J. (1996). Recurrence of autoimmune diabetes mellitus in recipients of cadaveric pancreatic grafts. N. Engl. J. Med. 335, 860–863.

Tönjes, R. R., Lower, R., Boller, K., Denner, K., Hasenmaier, B., Kirsch, H., König, H., Korbmacher, C., Limbach, C., Lugert, R., Phelps, R. C., Scherer, J., Thelen, K., Löwer, J., and Kurth, R. (1996). HERV-K: tne biologically most active human endogenous re-rovirus family. J. AIDS. Hum. Retrovirol. 13, 261–267.

Vyse, T. J., and Todd, J. A. (1996). Genetic analysis of autoimmune diseases. Cell 85, 311–318.

Wahle, E., and Keller, W. (1996). The biochemistry of polyadenylation. TIBS 21, 247–250.

Wain-Hobson, S. (1996). Running the gamut of retroviral variation. Trends Microbiol. 4, 135–141.

Weissmahr, R. N., Böni, J., and Schüpbach, J. (1997). Reverse Transcriptase activity in chicken embryo fibroblast culture supernatants is associated with particles containing endogenous avian retrovirus EAV-O RNA. J. Virol. 71, 3005–3012.

Whitcomb, J. M., and Hughes, S. H. (1992). Retroviral reverse transcription and integration: progress and problems. Annu. Rev. Cell. Biol. 8, 275–306.

White, J., Herman, A., Pullen, A. M., Kubo, R., Kappler, J. W., and Marrack, P. (1989). The Vb-specific superantigen staphylococcal enterotoxin B: stimulation of mature T cells and clonal deletion in neonatal mice. Cell 56, 27–35.

Wilkinson, D. A., et al. (1994). Endogenous human retroviruses. In The Retroviridae, J. A. Levy, ed. (New York: plenum Press), pp. 465–535.

Winslow, G. M., Scherer, M. T., Kappler, J. W., and Marrack, P. (1992). Detection and biochemical characterization of the mouse mammary tumor virus 7 superantigen (Mls-$1^a$). Cell 71, 719–730.

Wucherpfennig, K. W., and Strominger, J. L. (1995a). Selective binding of self peptides to disease-associated Major Histocompatibility Complex (MHC) molecules: a mechanism for MHC-linked susceptibility to human autoimmune diseases. J. Exp. Med. 181, 1597–1601.

Wucherpfennig, K. W, and Strominger, J. L. (1995b). Molecular mimicry in T cell-mediated autoimmunity: viral peptides activate human T cell clones specific for myelin basic protein. Cell 80, 695–705.

Xiong, Y., and Eickbusch, T. (1990). Origin and evolution of retroelements based upon their reverse transcripta se sequences. EMBO J. 9, 3353–3362.

York, D. F., Vigne, R., Verwoerd, D. W., and Guerat, G. (1992). Nucleotide sequence of the Jaagsiekte retrovirus, an exogenous and endogenous type D and B retrovirus of sheep and goats. J. Virol. 66, 4930–4939.

What is claimed is:

1. An isolated polypeptide comprising the amino acid sequence of SEQ ID NO:36.

2. An isolated polypeptide comprising the amino acid sequence of SEQ ID NO:40.

3. An isolated polypeptide comprising the amino acid sequence of SEQ ID NO:41.

4. A composition comprising the polypeptide as in any one of claims 1, 2, and 3 and a pharmaceutically-acceptable carrier.

* * * * *